US011667941B2

(12) United States Patent
Stemple et al.

(10) Patent No.: US 11,667,941 B2
(45) Date of Patent: Jun. 6, 2023

(54) COMPOSITIONS AND METHODS FOR TEMPLATE-FREE GEOMETRIC ENZYMATIC NUCLEIC ACID SYNTHESIS

(71) Applicant: CAMENA BIOSCIENCE LIMITED, Essex (GB)

(72) Inventors: Derek L. Stemple, Newton, MA (US); Andrew G. Fraser, Toronto (CA); Sylwia Mankowska, Essex (GB); Neil Bell, Essex (GB)

(73) Assignee: CAMENA BIOSCIENCE LIMITED, Essex (GB)

( * ) Notice: Subject to any disclaimer, the term of this patent is extended or adjusted under 35 U.S.C. 154(b) by 0 days.

(21) Appl. No.: 16/961,465

(22) PCT Filed: Jan. 14, 2019

(86) PCT No.: PCT/US2019/013441
§ 371 (c)(1),
(2) Date: Jul. 10, 2020

(87) PCT Pub. No.: WO2019/140353
PCT Pub. Date: Jul. 18, 2019

(65) Prior Publication Data
US 2021/0087600 A1 Mar. 25, 2021

Related U.S. Application Data

(60) Provisional application No. 62/617,148, filed on Jan. 12, 2018.

(51) Int. Cl.
*C12P 19/34* (2006.01)
*C12N 15/115* (2010.01)
(52) U.S. Cl.
CPC ............ *C12P 19/34* (2013.01); *C12N 15/115* (2013.01); *C12N 2310/16* (2013.01)
(58) Field of Classification Search
CPC combination set(s) only.
See application file for complete search history.

(56) References Cited

U.S. PATENT DOCUMENTS

| | | | |
|---|---|---|---|
| 5,114,839 A | 5/1992 | Blocker | |
| 5,602,000 A * | 2/1997 | Hyman | C12Q 1/686 435/6.12 |
| 6,479,262 B1 | 11/2002 | Delagrave | |
| 6,521,427 B1 | 2/2003 | Evans | |
| 6,635,453 B2 | 10/2003 | Delagrave et al. | |
| 6,670,127 B2 | 12/2003 | Evans | |
| 9,068,209 B2 | 6/2015 | Coope et al. | |
| 2004/0091920 A1 | 5/2004 | Tsuji et al. | |
| 2011/0104785 A1 * | 5/2011 | Vaidyanathan | C12Q 1/6806 435/280 |
| 2012/0190728 A1 * | 7/2012 | Bennett | A61P 11/00 514/44 A |
| 2014/0363851 A1 * | 12/2014 | Efcavitch | C12N 9/1264 435/91.5 |
| 2019/0169665 A1 | 6/2019 | Pedersen et al. | |

FOREIGN PATENT DOCUMENTS

| | | | | |
|---|---|---|---|---|
| EP | 2711370 A1 | 3/2014 | | |
| WO | WO-9517413 A1 | 6/1995 | | |
| WO | WO-9914318 A1 * | 3/1999 | .......... | B01J 19/0046 |
| WO | WO-0029616 A1 | 5/2000 | | |
| WO | WO-0049142 A1 | 8/2000 | | |
| WO | WO-0188173 A2 * | 11/2001 | ............. | C07H 21/00 |
| WO | WO-2011056866 A2 | 5/2011 | | |
| WO | WO-2012078312 A2 | 6/2012 | | |
| WO | WO-2012101151 A1 | 8/2012 | | |
| WO | WO-2013012674 A1 | 1/2013 | | |
| WO | WO-2013036810 A1 | 3/2013 | | |
| WO | WO-2015195257 A1 | 12/2015 | | |
| WO | WO-2018152323 A1 | 8/2018 | | |
| WO | WO-2019073072 A1 | 4/2019 | | |
| WO | WO-2019140353 A1 | 7/2019 | | |

OTHER PUBLICATIONS

Kelly, G. (1983) Ph.D Thesis, Purdue University. Part I only. (Year: 1983).*
Beskin A. D. et al. "On the mechanism of the modular primer effect", Nucleic Acids Research, vol. 23, No. 15, pp. 2881-2885 (Jan. 1995).
Davies, D. R., et al., "Three-Dimensional Structure of the Tn5 Synaptic Complex Transposition Intermediate," Science, vol. 289, No. 5476, pp. 77-85 (Jul. 2000).
England, T. E., "Dinucleoside pyrophosphate are substrates for T4-induced RNA ligase," Proc Natl Acad Sci USA 74, 4839-4842 (Nov. 1977).
Hao, J., et al., "A mild and reliable method to label enveloped virus with quantum dots by copper-free click chemistry," Anal Chem 84, 8364-8370 (2012).
Kelly, G., Ph.D. Thesis, Purdue University. Part I only, 122 pages (May 1983).
Kotler L.E. et al."DNA sequencing: modular primers assembled from a library of hexamers or pentamers", Proceedings of the National Academy of Sciences of the United States of America, May 1993, vol. 90, No. 9, pp. 4241-4245.
Levin, J. D., "Homogeneous Escherichia coli endonuclease IV. Characterization of an enzyme that recognizes oxidative damage in DNA," J Biol Chem 263, 8066-8071 (1988).
Lindahl, T., B., "DNA N-glycosidases: properties of uracil-DNA glycosidase from *Escherichia coli*," J Biol Chem 252, 3286-3294 (1977).
Mathews, A. S. et al., Photo-cleavable nucleotides for primer free enzyme mediated DNA synthesis, Organic & Biomolecular Chemistry, vol. 14, No. 35, pp. 8278-8288 (Jan. 2016).
Okuda, M., et al., "Use of Baby Spinach and Broccoli for imaging of structured cellular RNAs," Nucleic Acids Res 45, 1404-1415 (2017).
Paige, J. S. et al., "RNA mimics of green fluorescent protein," Science 333, 642-646 (Jul. 2011).

(Continued)

*Primary Examiner* — Samuel C Woolwine
*Assistant Examiner* — Catherine Konopka
(74) *Attorney, Agent, or Firm* — Cooley LLP; Ivor R. Elrifi; Matthew Pavao

(57) ABSTRACT

Disclosed are compositions and methods for template-free nucleic acid synthesis.

19 Claims, 29 Drawing Sheets

Specification includes a Sequence Listing.

(56) References Cited

OTHER PUBLICATIONS

Robson, C. N., et al., "Isolation of cDNA clones encoding a human apurinic/apyrimidinic endonuclease that corrects DNA repair and mutagenesis defects in *E. coli* xth (exonuclease III) mutants," Nucleic Acids Res 19, 5519-5523 (1991).

Torchia, C., et al., "Archaeal RNA ligase is a homodimeric protein that catalyzes intramolecular ligation of single-stranded RNA and DNA," Nucleic Acids Res 36, 6218-6227 (2008).

* cited by examiner

Example anchor primers for 3' and 5' extension

FIG. 2A

SEQ ID NO: 40
CT[CT]$_N$CTCTCTCTCTCTCTCTCTCTCTCCTTTCTCTGAGTCTGTAG-3'
SEQ ID NO: 41 GGGAAGGAAAGAGACTCAGACATC-5'

MlyI

5' attachment to bead

FIG. 2B

SEQ ID NO: 42 5'-CTTAAGACTCGATATCCCTGCAGGCTCTCTCTCTCTCTCTCTCT[CT]$_N$CT
SEQ ID NO: 43 3'-GAATTCTGAGCTATAGGGACGTCC

EcoRI MlyI EcoRV   SbfI

3' attachment to bead

FIG. 2C

CT[CT]$_N$CTCTCTCTCTCTCTCTCTCTCTCTCTCTCTCTCTU-3'
SEQ ID NO: 44

5' attachment to bead

FIG. 2D

SEQ ID NO: 45 A/CTCTCTCTCTCTCTCTCTCTCTCTCTCTCT[CT]$_N$CT

3' attachment to bead

>L29345.1 Aequorea victoria green-fluorescent protein (GFP) mRNA, complete cds
TACACACGAATAAAAGATAACAAAGATAGAGTAAAGGAGAAGAACTTTCACTGGAGTTGTCCCAATTCT
TGTTGAATTAGATGGCGATGTTAATGGGCAAAAATTCTCTGTCAGTGGAGAGGGTGAAGGTGATGCAA
CATACGGAAAACTTACCCTTAAATTTATTTGCACTACTGGGAAGCTACCTGTTCCATGGCCAACACTTG
TCACTACTTTCTCTTATGGTGTTCAATGCTTTTCAAGATACCCAGATCATATGAAACAGCATGACTTTT
CAAGAGTGCCATGCCCGAAGGTTATGTACAGGAACGCACTATATTTCAAGATGACGGGAACTACAAG
ACACGTGCTGAAGTCAAGTTTGAAGGTGATACCCTTGTTAATAGAATCGAGTTAAAAGGTATTGATTTT
AAAGAAGATGGAAACATTCTTGGACACAAATTGGAATACAACTATAACTCACACAATGTATACATCATG
GCAGACAAACAAAAGAATGGAATCAAAGTTAACTTCAAAATTAGACACAACATTGAAGATGGAAGC
GTTCAATTAGCAGACCATTATCAACAAAATACTCCAATTGGCGATGGCCCTGTCCTTTTACCAGACAA
CCATTACCTGTCAACACAACTGCTGGGATTACACATGGCATGGATGAACTCTACAAATAAAATGTCCAGACT
TGAGTTTGTAACAGCTGCTGGGATTACACATGGCATGGATGAACTCTACAAATAAAATGTCCAGACT
CCAATTGACACTAAAGTGTCCGAACAATTACTAAATTTATAGATTCATTAAATTTATGAATAATTATGATGTATTAATAGGGGTATTT
TCTTATTTAAATAGGCTACTGGAGTGTAT

SEQ ID NO: 46

FIG. 3A

| | Plate Set "a" (SEQ ID NOs: 47-68) | | Plate Set "b" (SEQ ID NOs: 69-90) |
|---|---|---|---|
| 1aA1 | TACACACGAATAAAAGATAAC | 1bA1 | AAAGATGAGTAAAGGAGAAGA |
| 1aA2 | ACTTTCACTGGAGTTGTCCC | 1bA2 | AATTCTTGTTGAATTAGATGG |
| 1aA3 | CGATGTTAATGGGCAAAAATT | 1bA3 | CTCTGTCAGTGGAGAGGGTGA |
| 1aA4 | AGGTGATGCAACATACGGAAA | 1bA4 | ACTTACCCTTAAATTTATTTG |
| 1aA5 | CACTACTGGGAAGCTACCTGT | 1bA5 | TCATGGCCAACACTTGTCAC |
| 1aA6 | TACTTTCTCTTATGGTGTTCA | 1bA6 | ATGCTTTTCAAGATACCCAGA |
| 1aA7 | TCATATGAAACAGCATGACTT | 1bA7 | TTTCAAGAGTGCCATGCCCGA |
| 1aA8 | AGGTTATGTACAGGAAAGAAC | 1bA8 | TATATTTTACAAGATGACGG |
| 1aA9 | GAACTACAAGACACGTGCTGA | 1bA9 | AGTCAAGTTTGAAGGTGATAC |
| 1aA10 | CCTTGTTAATAGAATCGAGTT | 1bA10 | AAAAGGTATTGATTTTAAAGA |
| 1aA11 | AGATGGAAACATTCTTGGACA | 1bA11 | CAAAATGGAATACAACTATAA |
| 1aA12 | CTCACACAATGTATACATCAT | 1bA12 | GGCAGACAAACAAAAGAATGG |
| 1aB1 | AATCAAAGTTAACTTCAAAAT | 1bB1 | TAGACACAACATTGAAGATGG |
| 1aB2 | AAGGTTCAATTAGCAGACCA | 1bB2 | TTATCAACAAAATACTCCAAT |
| 1aB3 | TGGCGATGGCCCTGTCCTTTT | 1bB3 | ACCAGACAACCATTACCTGTC |
| 1aB4 | CACACAATCTGCCCTTTCCAA | 1bB4 | AGATCCAACGAAAAGAGAGA |
| 1aB5 | TCACATGATCCTTCTTGAGTT | 1bB5 | TGTAACAGCTGCTGGGATTAC |
| 1aB6 | ACATGGCATGGATGAACTATA | 1bB6 | CAAATAAATGTCCAGACTTCC |
| 1aB7 | AATTGACACTAAAGTGTCCGA | 1bB7 | ACAATTACTAAATTCTCAGGG |
| 1aB8 | TTCCTGGTTAAATTCAGGGTG | 1bB8 | AGACTTTATTTATATATTTAT |
| 1aB9 | AGATTCATTAAATTTATGA | 1bB9 | ATAATTTATTATGATGTATTAA |
| 1aB10 | TAGGGGTATTTTCTTATTTAA | 1bB10 | ATAGGCTACTGGAGTGTAT |

FIG. 3B

Plate layout and pipetting moves

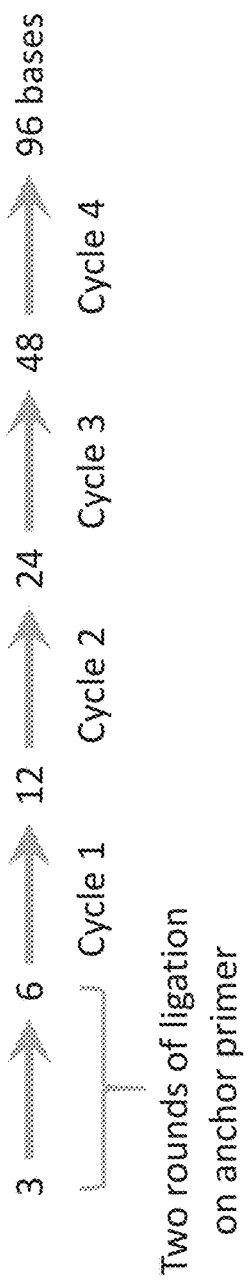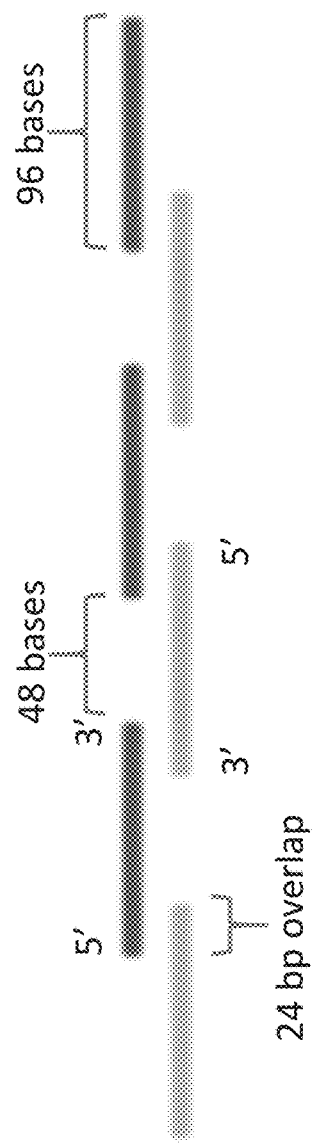
FIG. 10

- 5', 3' co-synthesis with sixteen overlapping fragments, generated from 5-mers, with 24 bp of overlap covers 2200 bases of *de novo* sequence
- Annealing, NA synthesis primed from 3' ends at overlaps, followed by ligation and generates a final product

SEQUENCE LISTING

<160> NUMBER OF SEQ ID NOS: 104

<210> SEQ ID NO 1
<211> LENGTH: 210
<212> TYPE: DNA
<213> ORGANISM: Aequorea victoria

<400> SEQUENCE: 1

```
tacacacgaa taaagataa caaagatgag taaaggagaa gaacttttca ctggagttgt      60
cccaattctt gttgaattag atggcgatgt taatgggcaa aaattctctg tcagtggaga    120
gggtgaaggt gatgcaacat acggaaaact taccctttaaa tttatttgca ctactgggaa   180
gctacctgtt ccatggccaa cacttgtcac                                     210
```

<210> SEQ ID NO 2
<211> LENGTH: 21
<212> TYPE: DNA
<213> ORGANISM: Artificial Sequence
<220> FEATURE:
<223> OTHER INFORMATION: N-mer

<400> SEQUENCE: 2

```
tacacacgaa taaagataa c                                                21
```

<210> SEQ ID NO 3
<211> LENGTH: 21
<212> TYPE: DNA
<213> ORGANISM: Artificial Sequence
<220> FEATURE:
<223> OTHER INFORMATION: N-mer

<400> SEQUENCE: 3

```
acttttcact ggagttgtcc c                                               21
```

<210> SEQ ID NO 4
<211> LENGTH: 21
<212> TYPE: DNA
<213> ORGANISM: Artificial Sequence
<220> FEATURE:
<223> OTHER INFORMATION: N-mer

<400> SEQUENCE: 4

```
cgatgttaat gggcaaaaat t                                               21
```

<210> SEQ ID NO 5
<211> LENGTH: 21
<212> TYPE: DNA
<213> ORGANISM: Artificial Sequence
<220> FEATURE:
<223> OTHER INFORMATION: N-mer

<400> SEQUENCE: 5

```
aggtgatgca acatacggaa a                                               21
```

<210> SEQ ID NO 6
<211> LENGTH: 21
<212> TYPE: DNA
<213> ORGANISM: Artificial Sequence
<220> FEATURE:
<223> OTHER INFORMATION: N-mer

<400> SEQUENCE: 6

```
aaagatgagt aaaggagaag a                                               21
```

<210> SEQ ID NO 7
<211> LENGTH: 21
<212> TYPE: DNA
<213> ORGANISM: Artificial Sequence
<220> FEATURE:
<223> OTHER INFORMATION: N-mer

<400> SEQUENCE: 7
aattcttgtt gaattagatg g     21

<210> SEQ ID NO 8
<211> LENGTH: 21
<212> TYPE: DNA
<213> ORGANISM: Artificial Sequence
<220> FEATURE:
<223> OTHER INFORMATION: N-mer

<400> SEQUENCE: 8
ctctgtcagt ggagagggtg a     21

<210> SEQ ID NO 9
<211> LENGTH: 21
<212> TYPE: DNA
<213> ORGANISM: Artificial Sequence
<220> FEATURE:
<223> OTHER INFORMATION: N-mer

<400> SEQUENCE: 9 acttacccett aaatttattt g     21

<210> SEQ ID NO 10
<211> LENGTH: 18
<212> TYPE: DNA
<213> ORGANISM: Artificial Sequence
<220> FEATURE:
<223> OTHER INFORMATION: T7 promoter sequence

<400> SEQUENCE: 10
ctatagtgag tcgtatta     18

<210> SEQ ID NO 11
<211> LENGTH: 39
<212> TYPE: DNA
<213> ORGANISM: Artificial Sequence
<220> FEATURE:
<223> OTHER INFORMATION: Anchor primer

<400> SEQUENCE: 11
ctatagtgag tcgtattacc gtagtgctgc gtcgagtgt     39

<210> SEQ ID NO 12
<211> LENGTH: 41
<212> TYPE: DNA
<213> ORGANISM: Artificial Sequence
<220> FEATURE:
<223> OTHER INFORMATION: Anchor primer
<220> FEATURE:
<221> NAME/KEY: misc_feature
<222> LOCATION: (1)..(1)
<223> OTHER INFORMATION: ribonucleotide
<220> FEATURE:
<221> NAME/KEY: misc_feature
<222> LOCATION: (2)..(41)
<223> OTHER INFORMATION: deoxyribonucleotide

<400> SEQUENCE: 12
uccattgtga gtcttatttc cgtagtgctg cgtcgagtgt c     41

<210> SEQ ID NO 13
<211> LENGTH: 12
<212> TYPE: DNA
<213> ORGANISM: Artificial Sequence
<220> FEATURE:
<223> OTHER INFORMATION: N-mer

```
<220> FEATURE:
<221> NAME/KEY: misc_feature
<222> LOCATION: (1)..(11)
<223> OTHER INFORMATION: deoxyribonucleotide
<220> FEATURE:
<221> NAME/KEY: misc_feature
<222> LOCATION: (12)..(12)
<223> OTHER INFORMATION: ribonucleotide

<400> SEQUENCE: 13
ccgtccttca cc                                                              12

<210> SEQ ID NO 14
<211> LENGTH: 12
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(11)
<223> OTHER INFORMATION: deoxyribonucleotide
<220> FEATURE:
<221> NAME/KEY: misc_feature
<222> LOCATION: (12)..(12)
<223> OTHER INFORMATION: ribonucleotide

<400> SEQUENCE: 14
gaactactgg ac                                                              12

<210> SEQ ID NO 15
<211> LENGTH: 12
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(11)
<223> OTHER INFORMATION: deoxyribonucleotide
<220> FEATURE:
<221> NAME/KEY: misc_feature
<222> LOCATION: (12)..(12)
<223> OTHER INFORMATION: ribonucleotide

<400> SEQUENCE: 15
ctcaacagta gc                                                              12

<210> SEQ ID NO 16
<211> LENGTH: 15
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(11)
<223> OTHER INFORMATION: deoxyribonucleotide
<220> FEATURE:
<221> NAME/KEY: misc_feature
<222> LOCATION: (12)..(12)
<223> OTHER INFORMATION: ribonucleotide

<400> SEQUENCE: 16
ggagctcaca ctcta                                                           15

<210> SEQ ID NO 17
<211> LENGTH: 35
<212> TYPE: DNA
<213> ORGANISM: Artificial Sequence
```

```
<220> FEATURE:
<223> OTHER INFORMATION: Anchor primer

<400> SEQUENCE: 17
tggaattctc gggtgccaag gatgttttt ttttt                              35

<210> SEQ ID NO 18
<211> LENGTH: 30
<212> TYPE: DNA
<213> ORGANISM: Artificial Sequence
<220> FEATURE:
<223> OTHER INFORMATION: Anchor primer
<220> FEATURE:
<221> NAME/KEY: misc_feature
<222> LOCATION: (1)..(29)
<223> OTHER INFORMATION: deoxyribonucleotide
<220> FEATURE:
<221> NAME/KEY: misc_feature
<222> LOCATION: (30)..(30)
<223> OTHER INFORMATION: ribonucleotide

<400> SEQUENCE: 18
tttttttttt gtagtgctgc gtgctcttca                                   30

<210> SEQ ID NO 19
<211> LENGTH: 12
<212> TYPE: RNA
<213> ORGANISM: Artificial Sequence
<220> FEATURE:
<223> OTHER INFORMATION: N-mer

<400> SEQUENCE: 19
ggugaaggac gg                                                      12

<210> SEQ ID NO 20
<211> LENGTH: 19
<212> TYPE: DNA
<213> ORGANISM: Artificial Sequence
<220> FEATURE:
<223> OTHER INFORMATION: Short reverse complementary oligonucleotide

<400> SEQUENCE: 20
gaagagcacg cagcactac                                               19

<210> SEQ ID NO 21
<211> LENGTH: 12
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(11)
<223> OTHER INFORMATION: deoxyribonucleotide
<220> FEATURE:
<221> NAME/KEY: misc_feature
<222> LOCATION: (12)..(12)
<223> OTHER INFORMATION: ribonucleotide

<400> SEQUENCE: 21
ccgtccttca cc                                                      12

<210> SEQ ID NO 22
<211> LENGTH: 12
<212> TYPE: RNA
<213> ORGANISM: Artificial Sequence
<220> FEATURE:
<223> OTHER INFORMATION: N-mer
```

<400> SEQUENCE: 22
gagugugagc uc                                                             12

<210> SEQ ID NO 23
<211> LENGTH: 59
<212> TYPE: DNA
<213> ORGANISM: Artificial Sequence
<220> FEATURE:
<223> OTHER INFORMATION: N-mer

<400> SEQUENCE: 23
tacacgacgc tctctgaaga cactcgatcc ctacacgacg ccgtccgttc tacctcttt         59

<210> SEQ ID NO 24
<211> LENGTH: 40
<212> TYPE: DNA
<213> ORGANISM: Artificial Sequence
<220> FEATURE:
<223> OTHER INFORMATION: N-mer

<400> SEQUENCE: 24
gacacatgaa agcttgaatt cacggcatat gagtccatgg                               40

<210> SEQ ID NO 25
<211> LENGTH: 30
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(29)
<223> OTHER INFORMATION: deoxyribonucleotide
<220> FEATURE:
<221> NAME/KEY: misc_feature
<222> LOCATION: (30)..(30)
<223> OTHER INFORMATION: ribonucleotide

<400> SEQUENCE: 25 ttttttttttt cttccgatct gagtccagcg                                         30

<210> SEQ ID NO 26
<211> LENGTH: 26
<212> TYPE: RNA
<213> ORGANISM: Artificial Sequence
<220> FEATURE:
<223> OTHER INFORMATION: N-mer

<400> SEQUENCE: 26
guucagaguu cuacaguccg acgauc                                              26

<210> SEQ ID NO 27
<211> LENGTH: 31
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (23)..(23)
<223> OTHER INFORMATION: fluorescein-labeled base

<400> SEQUENCE: 27
aagtagcgaa ctactggacc cgtccttcac c                                        31

```
<210> SEQ ID NO 28
<211> LENGTH: 31
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (23)..(23)
<223> OTHER INFORMATION: fluorescein-labeled base

<400> SEQUENCE: 28
cagtagcgaa ctactggacc cgtccttcac c                              31

<210> SEQ ID NO 29
<211> LENGTH: 31
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (23)..(23)
<223> OTHER INFORMATION: fluorescein-labeled base

<400> SEQUENCE: 29
gagtagcgaa ctactggacc cgtccttcac c                              31

<210> SEQ ID NO 30
<211> LENGTH: 31
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (23)..(23)
<223> OTHER INFORMATION: fluorescein-labeled base

<400> SEQUENCE: 30
tagtagcgaa ctactggacc cgtccttcac c                              31

<210> SEQ ID NO 31
<211> LENGTH: 18
<212> TYPE: DNA
<213> ORGANISM: Artificial Sequence
<220> FEATURE:
<223> OTHER INFORMATION: N-mer

<400> SEQUENCE: 31
actagttacg gagctcac                                             18

<210> SEQ ID NO 32
<211> LENGTH: 18
<212> TYPE: DNA
<213> ORGANISM: Artificial Sequence
<220> FEATURE:
<223> OTHER INFORMATION: N-mer

<400> SEQUENCE: 32
tgaatgaaat ggtgaagg                                             18

<210> SEQ ID NO 33
<211> LENGTH: 17
<212> TYPE: DNA
<213> ORGANISM: Artificial Sequence
<220> FEATURE:
<223> OTHER INFORMATION: N-mer
```

<400> SEQUENCE: 33
cgctttaggt taagact                                                17

<210> SEQ ID NO 34
<211> LENGTH: 20
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(19)
<223> OTHER INFORMATION: deoxyribonucleotide
<220> FEATURE:
<221> NAME/KEY: misc_feature
<222> LOCATION: (20)..(20)
<223> OTHER INFORMATION: ribonucleotide

<400> SEQUENCE: 34
ggagctcaca ctctactcaa                                             20

<210> SEQ ID NO 35
<211> LENGTH: 20
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(19)
<223> OTHER INFORMATION: deoxyribonucleotide
<220> FEATURE:
<221> NAME/KEY: misc_feature
<222> LOCATION: (20)..(20)
<223> OTHER INFORMATION: ribonucleotide

<400> SEQUENCE: 35
ggagctcaca ctctactcac                                             20

<210> SEQ ID NO 36
<211> LENGTH: 20
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(19)
<223> OTHER INFORMATION: deoxyribonucleotide
<220> FEATURE:
<221> NAME/KEY: misc_feature
<222> LOCATION: (20)..(20)
<223> OTHER INFORMATION: ribonucleotide

<400> SEQUENCE: 36
ggagctcaca ctctactcag                                             20

<210> SEQ ID NO 37
<211> LENGTH: 20
<212> TYPE: DNA
<213> ORGANISM: Artificial Sequence
<220> FEATURE:
<223> OTHER INFORMATION: N-mer
<220> FEATURE:
<221> NAME/KEY: misc_feature
<222> LOCATION: (1)..(19)
<223> OTHER INFORMATION: deoxyribonucleotide
<220> FEATURE:
<221> NAME/KEY: misc_feature
<222> LOCATION: (20)..(20)
<223> OTHER INFORMATION: ribonucleotide

```
<400> SEQUENCE: 37
ggagctcaca ctctactcat                                              20

<210> SEQ ID NO 38
<211> LENGTH: 58
<212> TYPE: DNA
<213> ORGANISM: Artificial Sequence
<220> FEATURE:
<223> OTHER INFORMATION: Anchor primer

<400> SEQUENCE: 38
ccatggactc atatgccgtg aattcaagct ttcatgtgtc ttcatagtcc gtcgtgta    58

<210> SEQ ID NO 39
<211> LENGTH: 20
<212> TYPE: RNA
<213> ORGANISM: Artificial Sequence
<220> FEATURE:
<223> OTHER INFORMATION: N-mer

<400> SEQUENCE: 39
aguucugcag ucugcagaaa                                              20

<210> SEQ ID NO 40
<211> LENGTH: 54
<212> TYPE: DNA
<213> ORGANISM: Artificial Sequence
<220> FEATURE:
<223> OTHER INFORMATION: Anchor primer

<400> SEQUENCE: 40
ctctctctct ctctctctct ctctctctct cccttccttt ctctgagtct gtag        54

<210> SEQ ID NO 41
<211> LENGTH: 24
<212> TYPE: DNA
<213> ORGANISM: Artificial Sequence
<220> FEATURE:
<223> OTHER INFORMATION: Short reverse complementary oligonucleotide

<400> SEQUENCE: 41
gggaaggaaa gagactcaga catc                                         24

<210> SEQ ID NO 42
<211> LENGTH: 52
<212> TYPE: DNA
<213> ORGANISM: Artificial Sequence
<220> FEATURE:
<223> OTHER INFORMATION: Anchor primer

<400> SEQUENCE: 42
cttaagactc gatatccctg caggctctct ctctctctct ctctctctct ct          52

<210> SEQ ID NO 43
<211> LENGTH: 24
<212> TYPE: DNA
<213> ORGANISM: Artificial Sequence
<220> FEATURE:
<223> OTHER INFORMATION: Short reverse complementary oligonucleotide

<400> SEQUENCE: 43
gaattctgag ctatagggac gtcc                                         24
```

-continued

```
<210> SEQ ID NO 44
<211> LENGTH: 55
<212> TYPE: DNA
<213> ORGANISM: Artificial Sequence
<220> FEATURE:
<223> OTHER INFORMATION: Anchor primer
<220> FEATURE:
<221> NAME/KEY: misc_feature
<222> LOCATION: (1)..(54)
<223> OTHER INFORMATION: deoxyribonucleotide
<220> FEATURE:
<221> NAME/KEY: misc_feature
<222> LOCATION: (55)..(55)
<223> OTHER INFORMATION: ribonucleotide

<400> SEQUENCE: 44
ctctctctct ctctctctct ctctctctct ctctctctct ctctu            55

<210> SEQ ID NO 45
<211> LENGTH: 47
<212> TYPE: DNA
<213> ORGANISM: Artificial Sequence
<220> FEATURE:
<223> OTHER INFORMATION: Anchor primer
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or t

<400> SEQUENCE: 45
anctctctct ctctctctcc tctctctctc tctctctctc tctctct           47

<210> SEQ ID NO 46
<211> LENGTH: 922
<212> TYPE: DNA
<213> ORGANISM: Aequorea victoria

<400> SEQUENCE: 46
tacacacgaa taaagataaa caaagatgag taaaggagaa gaacttttca ctggagttgt    60
cccaattctt gttgaattag atggcgatgt taatgggcaa aaattctctg tcagtggaga   120
gggtgaaggt gatgcaacat acggaaaact tacccttaaa tttatttgca ctactgggaa   180
gctacctgtt ccatggccaa cacttgtcac tactttctct tatggtgttc aatgcttttc   240
aagatacccc gatcatatga acagcatga cttttttcaag agtgccatgc ccgaaggtta   300
tgtacaggaa agaactatat tttacaaaga tgacgggaac tacaagacac gtgctgaagt   360
caagtttgaa ggtgataccc ttgttaatag aatcgagtta aaaggtattg attttaaaga   420
agatggaaac attcttggac acaaaatgga atacaactat aactcacata atgtatacat   480
catggcagac aaaccaaaga atggaatcaa agttaacttc aaaattagac acaacattaa   540
agatggaagc gttcaattag cagaccatta tcaacaaaat actccaattg gcgatggccc   600 tgtccttttta ccagacaacc attacctgtc cacacaatct gccctttcca aagatcccaa   660
cgaaaagaga gatcacatga tccttcttga gtttgtaaca gctgctggga ttacacatgg   720
catggatgaa ctatacaaat aaatgtccag acttccaatt gacactaaag tgtccgaaca   780
attactaaat tctcagggtt cctggttaaa ttcaggctga gactttattt atatatttat   840
agattcatta aaatttttatg aataatttat tgatgttatt ataggggct attttcttat   900 taaataggct actggagtgt at                                            922
```

```
<210> SEQ ID NO 47
<211> LENGTH: 21
<212> TYPE: DNA
<213> ORGANISM: Artificial Sequence
<220> FEATURE:
<223> OTHER INFORMATION: N-mer

<400> SEQUENCE: 47
tacacacgaa taaaagataa c                                            21

<210> SEQ ID NO 48
<211> LENGTH: 21
<212> TYPE: DNA
<213> ORGANISM: Artificial Sequence
<220> FEATURE:
<223> OTHER INFORMATION: N-mer

<400> SEQUENCE: 48
acttttcact ggagttgtcc c                                            21

<210> SEQ ID NO 49
<211> LENGTH: 21
<212> TYPE: DNA
<213> ORGANISM: Artificial Sequence
<220> FEATURE:
<223> OTHER INFORMATION: N-mer

<400> SEQUENCE: 49
cgatgttaat gggcaaaaat t                                            21

<210> SEQ ID NO 50
<211> LENGTH: 21
<212> TYPE: DNA
<213> ORGANISM: Artificial Sequence
<220> FEATURE:
<223> OTHER INFORMATION: N-mer

<400> SEQUENCE: 50
aggtgatgca acatacggaa a                                            21

<210> SEQ ID NO 51
<211> LENGTH: 21
<212> TYPE: DNA
<213> ORGANISM: Artificial Sequence
<220> FEATURE:
<223> OTHER INFORMATION: N-mer

<400> SEQUENCE: 51
cactactggg aagctacctg t                                            21

<210> SEQ ID NO 52
<211> LENGTH: 21
<212> TYPE: DNA
<213> ORGANISM: Artificial Sequence
<220> FEATURE:
<223> OTHER INFORMATION: N-mer

<400> SEQUENCE: 52
tactttctct tatggtgttc a                                            21

<210> SEQ ID NO 53
<211> LENGTH: 21
<212> TYPE: DNA
<213> ORGANISM: Artificial Sequence
<220> FEATURE:
<223> OTHER INFORMATION: N-mer
```

```
<400> SEQUENCE: 53
tcatatgaaa cagcatgact t                                              21

<210> SEQ ID NO 54
<211> LENGTH: 21
<212> TYPE: DNA
<213> ORGANISM: Artificial Sequence
<220> FEATURE:
<223> OTHER INFORMATION: N-mer

<400> SEQUENCE: 54
aggttatgta caggaaagaa c                                              21

<210> SEQ ID NO 55
<211> LENGTH: 21
<212> TYPE: DNA
<213> ORGANISM: Artificial Sequence
<220> FEATURE:
<223> OTHER INFORMATION: N-mer

<400> SEQUENCE: 55
gaactacaag acacgtgctg a                                              21

<210> SEQ ID NO 56
<211> LENGTH: 21
<212> TYPE: DNA
<213> ORGANISM: Artificial Sequence
<220> FEATURE:
<223> OTHER INFORMATION: N-mer

<400> SEQUENCE: 56
ccttgttaat agaatcgagt t                                              21

<210> SEQ ID NO 57
<211> LENGTH: 21
<212> TYPE: DNA
<213> ORGANISM: Artificial Sequence
<220> FEATURE:
<223> OTHER INFORMATION: N-mer

<400> SEQUENCE: 57
agatggaaac attcttggac a                                              21

<210> SEQ ID NO 58
<211> LENGTH: 21
<212> TYPE: DNA
<213> ORGANISM: Artificial Sequence
<220> FEATURE:
<223> OTHER INFORMATION: N-mer

<400> SEQUENCE: 58
ctcacataat gtatacatca t                                              21

<210> SEQ ID NO 59
<211> LENGTH: 21
<212> TYPE: DNA
<213> ORGANISM: Artificial Sequence
<220> FEATURE:
<223> OTHER INFORMATION: N-mer

<400> SEQUENCE: 59
aatcaaagtt aacttcaaaa t                                              21
```

<210> SEQ ID NO 60
<211> LENGTH: 21
<212> TYPE: DNA
<213> ORGANISM: Artificial Sequence
<220> FEATURE:
<223> OTHER INFORMATION: N-mer

<400> SEQUENCE: 60
aagcgttcaa ttagcagacc a                                              21

<210> SEQ ID NO 61
<211> LENGTH: 21
<212> TYPE: DNA
<213> ORGANISM: Artificial Sequence
<220> FEATURE:
<223> OTHER INFORMATION: N-mer

<400> SEQUENCE: 61
tggcgatggc cctgtcctttt t                                             21

<210> SEQ ID NO 62
<211> LENGTH: 21
<212> TYPE: DNA
<213> ORGANISM: Artificial Sequence
<220> FEATURE:
<223> OTHER INFORMATION: N-mer

<400> SEQUENCE: 62
cacacaatct gcccttttcca a                                             21

<210> SEQ ID NO 63
<211> LENGTH: 21
<212> TYPE: DNA
<213> ORGANISM: Artificial Sequence
<220> FEATURE:
<223> OTHER INFORMATION: N-mer

<400> SEQUENCE: 63
tcacatgatc cttcttgagt t                                              21

<210> SEQ ID NO 64
<211> LENGTH: 21
<212> TYPE: DNA
<213> ORGANISM: Artificial Sequence
<220> FEATURE:
<223> OTHER INFORMATION: N-mer

<400> SEQUENCE: 64
acatggcatg gatgaactat a                                              21

<210> SEQ ID NO 65
<211> LENGTH: 21
<212> TYPE: DNA
<213> ORGANISM: Artificial Sequence
<220> FEATURE:
<223> OTHER INFORMATION: N-mer

<400> SEQUENCE: 65
aattgacact aaagtgtccg a                                              21

<210> SEQ ID NO 66
<211> LENGTH: 21
<212> TYPE: DNA
<213> ORGANISM: Artificial Sequence
<220> FEATURE:
<223> OTHER INFORMATION: N-mer

```
<400> SEQUENCE: 66
ttcctggtta aattcaggct g                                          21

<210> SEQ ID NO 67
<211> LENGTH: 21
<212> TYPE: DNA
<213> ORGANISM: Artificial Sequence
<220> FEATURE:
<223> OTHER INFORMATION: N-mer

<400> SEQUENCE: 67
agattcatta aaattttatg a                                          21

<210> SEQ ID NO 68
<211> LENGTH: 21
<212> TYPE: DNA
<213> ORGANISM: Artificial Sequence
<220> FEATURE:
<223> OTHER INFORMATION: N-mer

<400> SEQUENCE: 68 tagggctat tttcttatta a                                           21

<210> SEQ ID NO 69
<211> LENGTH: 21
<212> TYPE: DNA
<213> ORGANISM: Artificial Sequence
<220> FEATURE:
<223> OTHER INFORMATION: N-mer

<400> SEQUENCE: 69
aaagatgagt aaaggagaag a                                          21

<210> SEQ ID NO 70
<211> LENGTH: 21
<212> TYPE: DNA
<213> ORGANISM: Artificial Sequence
<220> FEATURE:
<223> OTHER INFORMATION: N-mer

<400> SEQUENCE: 70
aattcttgtt gaattagatg g                                          21

<210> SEQ ID NO 71
<211> LENGTH: 21
<212> TYPE: DNA
<213> ORGANISM: Artificial Sequence
<220> FEATURE:
<223> OTHER INFORMATION: N-mer

<400> SEQUENCE: 71
ctctgtcagt ggagagggtg a                                          21

<210> SEQ ID NO 72
<211> LENGTH: 21
<212> TYPE: DNA
<213> ORGANISM: Artificial Sequence
<220> FEATURE:
<223> OTHER INFORMATION: N-mer

<400> SEQUENCE: 72
acttaccctt aaatttattt g                                          21
```

```
<210> SEQ ID NO 73
<211> LENGTH: 21
<212> TYPE: DNA
<213> ORGANISM: Artificial Sequence
<220> FEATURE:
<223> OTHER INFORMATION: N-mer

<400> SEQUENCE: 73
tccatggcca acacttgtca c                                              21

<210> SEQ ID NO 74
<211> LENGTH: 21
<212> TYPE: DNA
<213> ORGANISM: Artificial Sequence
<220> FEATURE:
<223> OTHER INFORMATION: N-mer

<400> SEQUENCE: 74
atgcttttca agatacccag a                                              21

<210> SEQ ID NO 75
<211> LENGTH: 21
<212> TYPE: DNA
<213> ORGANISM: Artificial Sequence
<220> FEATURE:
<223> OTHER INFORMATION: N-mer

<400> SEQUENCE: 75
tttcaagagt gccatgcccg a                                              21

<210> SEQ ID NO 76
<211> LENGTH: 21
<212> TYPE: DNA
<213> ORGANISM: Artificial Sequence
<220> FEATURE:
<223> OTHER INFORMATION: N-mer

<400> SEQUENCE: 76
tatattttac aaagatgacg g                                              21

<210> SEQ ID NO 77
<211> LENGTH: 21
<212> TYPE: DNA
<213> ORGANISM: Artificial Sequence
<220> FEATURE:
<223> OTHER INFORMATION: N-mer

<400> SEQUENCE: 77
agtcaagttt gaaggtgata c                                              21

<210> SEQ ID NO 78
<211> LENGTH: 21
<212> TYPE: DNA
<213> ORGANISM: Artificial Sequence
<220> FEATURE:
<223> OTHER INFORMATION: N-mer

<400> SEQUENCE: 78
aaaaggtatt gattttaaag a                                              21

<210> SEQ ID NO 79
<211> LENGTH: 21
<212> TYPE: DNA
<213> ORGANISM: Artificial Sequence
<220> FEATURE:
<223> OTHER INFORMATION: N-mer
```

```
<400> SEQUENCE: 79
caaaatggaa tacaactata a                                              21

<210> SEQ ID NO 80
<211> LENGTH: 21
<212> TYPE: DNA
<213> ORGANISM: Artificial Sequence
<220> FEATURE:
<223> OTHER INFORMATION: N-mer

<400> SEQUENCE: 80
ggcagacaaa ccaaagaatg g                                              21

<210> SEQ ID NO 81
<211> LENGTH: 21
<212> TYPE: DNA
<213> ORGANISM: Artificial Sequence
<220> FEATURE:
<223> OTHER INFORMATION: N-mer

<400> SEQUENCE: 81
tagacacaac attaaagatg g                                              21

<210> SEQ ID NO 82
<211> LENGTH: 21
<212> TYPE: DNA
<213> ORGANISM: Artificial Sequence
<220> FEATURE:
<223> OTHER INFORMATION: N-mer

<400> SEQUENCE: 82
ttatcaacaa aatactccaa t                                              21

<210> SEQ ID NO 83
<211> LENGTH: 21
<212> TYPE: DNA
<213> ORGANISM: Artificial Sequence
<220> FEATURE:
<223> OTHER INFORMATION: N-mer

<400> SEQUENCE: 83
accagacaac cattacctgt c                                              21

<210> SEQ ID NO 84
<211> LENGTH: 21
<212> TYPE: DNA
<213> ORGANISM: Artificial Sequence
<220> FEATURE:
<223> OTHER INFORMATION: N-mer

<400> SEQUENCE: 84
agatcccaac gaaaagagag a                                              21

<210> SEQ ID NO 85
<211> LENGTH: 21
<212> TYPE: DNA
<213> ORGANISM: Artificial Sequence
<220> FEATURE:
<223> OTHER INFORMATION: N-mer

<400> SEQUENCE: 85
tgtaacagct gctgggatta c                                              21
```

```
<210> SEQ ID NO 86
<211> LENGTH: 21
<212> TYPE: DNA
<213> ORGANISM: Artificial Sequence
<220> FEATURE:
<223> OTHER INFORMATION: N-mer

<400> SEQUENCE: 86
caaataaatg tccagacttc c                                              21

<210> SEQ ID NO 87
<211> LENGTH: 21
<212> TYPE: DNA
<213> ORGANISM: Artificial Sequence
<220> FEATURE:
<223> OTHER INFORMATION: N-mer

<400> SEQUENCE: 87
acaattacta aattctcagg g                                              21

<210> SEQ ID NO 88
<211> LENGTH: 21
<212> TYPE: DNA
<213> ORGANISM: Artificial Sequence
<220> FEATURE:
<223> OTHER INFORMATION: N-mer

<400> SEQUENCE: 88
agactttatt tatatattta t                                              21

<210> SEQ ID NO 89
<211> LENGTH: 21
<212> TYPE: DNA
<213> ORGANISM: Artificial Sequence
<220> FEATURE:
<223> OTHER INFORMATION: N-mer

<400> SEQUENCE: 89
ataatttatt gatgttatta a                                              21

<210> SEQ ID NO 90
<211> LENGTH: 19
<212> TYPE: DNA
<213> ORGANISM: Artificial Sequence
<220> FEATURE:
<223> OTHER INFORMATION: N-mer

<400> SEQUENCE: 90
ataggctact ggagtgtat                                                 19

<210> SEQ ID NO 91
<211> LENGTH: 16
<212> TYPE: DNA
<213> ORGANISM: Artificial Sequence
<220> FEATURE:
<223> OTHER INFORMATION: Anchor primer

<400> SEQUENCE: 91
gatatcgagt cttaag                                                    16

<210> SEQ ID NO 92
<211> LENGTH: 37
<212> TYPE: DNA
<213> ORGANISM: Artificial Sequence
<220> FEATURE:
<223> OTHER INFORMATION: Ligation product
```

```
<400> SEQUENCE: 92
gatatcgagt cttaagtaca cacgaataaa agataac                              37

<210> SEQ ID NO 93
<211> LENGTH: 37
<212> TYPE: DNA
<213> ORGANISM: Artificial Sequence
<220> FEATURE:
<223> OTHER INFORMATION: Ligation product

<400> SEQUENCE: 93
gatatcgagt cttaagactt ttcactggag ttgtccc                              37

<210> SEQ ID NO 94
<211> LENGTH: 37
<212> TYPE: DNA
<213> ORGANISM: Artificial Sequence
<220> FEATURE:
<223> OTHER INFORMATION: Ligation product

<400> SEQUENCE: 94
gatatcgagt cttaagcgat gttaatgggc aaaaatt                              37

<210> SEQ ID NO 95
<211> LENGTH: 37
<212> TYPE: DNA
<213> ORGANISM: Artificial Sequence
<220> FEATURE:
<223> OTHER INFORMATION: Ligation product

<400> SEQUENCE: 95
gatatcgagt cttaagaggt gatgcaacat acggaaa                              37

<210> SEQ ID NO 96
<211> LENGTH: 16
<212> TYPE: DNA
<213> ORGANISM: Artificial Sequence
<220> FEATURE:
<223> OTHER INFORMATION: Short reverse complementary oligonucleotide

<400> SEQUENCE: 96
ctatagctca gaattc                                                    16

<210> SEQ ID NO 97
<211> LENGTH: 42
<212> TYPE: DNA
<213> ORGANISM: Artificial Sequence
<220> FEATURE:
<223> OTHER INFORMATION: Released ligation product

<400> SEQUENCE: 97
acttttcact ggagttgtcc caattcttgt tgaattagat gg                        42

<210> SEQ ID NO 98
<211> LENGTH: 41
<212> TYPE: DNA
<213> ORGANISM: Artificial Sequence
<220> FEATURE:
<223> OTHER INFORMATION: Released ligation product

<400> SEQUENCE: 98
aggtgatgca acatacggaa aacttaccct taaatttatt t                         41
```

-continued

<210> SEQ ID NO 99
<211> LENGTH: 100
<212> TYPE: DNA
<213> ORGANISM: Artificial Sequence
<220> FEATURE:
<223> OTHER INFORMATION: Ligation product

<400> SEQUENCE: 99
gatatcgagt cttaagtaca cacgaataaa agataacaaa gatgagtaaa ggagaagaac    60
ttttcactgg agttgtccca attcttgttg aattagatgg    100

<210> SEQ ID NO 100
<211> LENGTH: 99
<212> TYPE: DNA
<213> ORGANISM: Artificial Sequence
<220> FEATURE:
<223> OTHER INFORMATION: Ligation product

<400> SEQUENCE: 100
gatatcgagt cttaagcgat gttaatgggc aaaaattctc tgtcagtgga gagggtgaag    60
gtgatgcaac atacggaaaa cttacccctta aatttattt    99

<210> SEQ ID NO 101
<211> LENGTH: 83
<212> TYPE: DNA
<213> ORGANISM: Artificial Sequence
<220> FEATURE:
<223> OTHER INFORMATION: Released ligation product

<400> SEQUENCE: 101
cgatgttaat gggcaaaaat tctctgtcag tggagagggt gaaggtgatg caacatacgg    60
aaaacttacc cttaaatttta ttt    83

<210> SEQ ID NO 102
<211> LENGTH: 153
<212> TYPE: DNA
<213> ORGANISM: Artificial Sequence
<220> FEATURE:
<223> OTHER INFORMATION: Ligation product

<400> SEQUENCE: 102
gatatcgagt cttaagtaca cacgaataaa agataacaaa gatgagtaaa ggagaagaac    60
ttttcactgg agttgtccca attcttgttg aattagatgg cgatgttaat gggcaaaaat    120
tctctgtcag tggagagggt gaaggtgatg caa    153

<210> SEQ ID NO 103
<211> LENGTH: 167
<212> TYPE: DNA
<213> ORGANISM: Artificial Sequence
<220> FEATURE:
<223> OTHER INFORMATION: Released ligation product

<400> SEQUENCE: 103
tacacacgaa taaaagataa caaagatgag taaaggagaa gaacttttca ctggagttgt    60
cccaattctt gttgaattag atggcgatgt taatgggcaa aaattctctg tcagtggaga    120
gggtgaaggt gatgcaacat acggaaaact tacccttaaa tttattt    167

<210> SEQ ID NO 104
<211> LENGTH: 22
<212> TYPE: DNA
<213> ORGANISM: Artificial Sequence -continued

```
<220> FEATURE:
<223> OTHER INFORMATION: DNA spacer sequence

<400> SEQUENCE: 104
ccatggactc atatgccgtg aa                                              22
```

COMPOSITIONS AND METHODS FOR TEMPLATE-FREE GEOMETRIC ENZYMATIC NUCLEIC ACID SYNTHESIS

RELATED APPLICATIONS

This application is a U.S. National Phase Application, filed under 35 U.S.C. § 371, of International Application No. PCT/US2019/013441, filed on Jan. 14, 2019, which claims the benefit of provisional application U.S. Ser. No. 62/617,148 filed Jan. 12, 2018, the contents of each of which are herein incorporated by reference in their entireties.

INCORPORATION OF SEQUENCE LISTING

The contents of the text file named "DNWR-003_001WO.txt," which was created on Jan. 11, 2019 and is 23.0 KB in size, are hereby incorporated by reference in their entirety.

FIELD OF THE DISCLOSURE

The present disclosure provides compositions and methods for template-free geometric enzymatic nucleic acid synthesis of arbitrarily programmed sequence.

BACKGROUND

Over the last decade there has been an increase in demand for synthetic DNA molecules, which are used in a range of molecular biology applications. This increase has, in part, been driven by advances in DNA sequencing technology. However, while there have been significant developments in DNA sequencing technology, DNA synthesis technology has not progressed at a comparable pace and consequently the state of the art technology does not satisfy the current market needs. The present disclosure provides compositions and methods for template-free geometric enzymatic DNA synthesis that provide a solution to the unmet need in the art for the production of long, error-free, inexpensive DNA sequences having the superior accuracy and speed of synthesis demonstrated by the compositions and methods of the present disclosure.

SUMMARY

The present disclosure provides a composition comprising a nucleic acid (NA) sequence capable of participating in geometric synthesis or parallel synthesis reactions, wherein the nucleic acid comprises an arbitrary length. In some aspects of the compositions of the disclosure, including those comprising a plurality of NA sequences, each NA sequence of the plurality of NA sequences comprises or consists of a 3-nucleotide oligonucleotide (a 3-mer), a 4-nucleotide oligonucleotide (a 4-mer), or a 5-nucleotide oligonucleotide (a 5-mer). In some aspects, each NA sequence of the plurality of NA sequences comprises or consists of a 3-mer and wherein the plurality of NA sequences comprises 64 unique NA sequences. In some aspects, each NA sequence of the plurality of NA sequences comprises or consists of a 4-mer and wherein the plurality of NA sequences comprises 256 unique NA sequences. In some aspects, each NA sequence of the plurality of NA sequences comprises or consists of a 5-mer and wherein the plurality of NA sequences comprises 1024 unique NA sequences. In some aspects, the plurality of NA sequences comprises or consists of each unique 3-mer NA sequence, each unique 4-mer NA sequence and each unique 5-mer NA sequence, and the plurality of NA sequences comprises 1344 unique NA sequences.

In some aspects of the compositions of the disclosure, each NA sequence of the plurality of NA sequences comprises a monophosphate at a 3' end or at a 5' end of the NA sequence. In some aspects, each NA sequence of the plurality of NA sequences comprises a monophosphate at a 3' end and at a 5' end of the NA sequence.

In some aspects of the compositions of the disclosure, each NA sequence of the plurality of NA sequences is 5' adenylated.

In some aspects of the compositions of the disclosure, each NA sequence of the plurality of NA sequences comprises a hydroxyl group at a 3' end or at a 5' end of the NA sequence. In some aspects, each NA sequence of the plurality of NA sequences comprises a hydroxyl group at a 3' end and at a 5' end of the NA sequence.

In some aspects of the compositions of the disclosure, each NA sequence of the plurality of NA sequences comprises a photo-convertible blocking group at a 3' end or at a 5' end of the NA sequence. In some aspects, each NA sequence of the plurality of NA sequences comprises a photo-convertible blocking group at a 3' end and at a 5' end of the NA sequence.

In some aspects of the compositions of the disclosure, each NA sequence of the plurality of NA sequences comprises an O-2-nitrobenzyl blocking at a 3' end or at a 5' end of the NA sequence. In some aspects, each NA sequence of the plurality of NA sequences comprises an O-2-nitrobenzyl blocking at a 3' end and at a 5' end of the NA sequence.

In some aspects of the compositions of the disclosure, each NA sequence of the plurality of NA sequences comprises a triphosphate at a 5' end of the NA sequence.

The disclosure provides a composition comprising a nucleic acid sequence comprising an anchor primer sequence, wherein the anchor primer sequence comprises a nucleic acid sequence comprising a spacer and a moiety and wherein the spacer and the moiety attach the anchor primer sequence to a solid support at a first end, and a release element, wherein the release element comprises at least one nucleic acid sequence that facilitates release of a distal sequence at a second end, wherein the distal sequence is located 3' of the release element. In some aspects, the moiety is positioned at a 5' end of the anchor primer sequence or at a 5' end of the nucleic acid sequence. In some aspects, the moiety is positioned at a 3' end of the anchor primer sequence or at a 3' end of the nucleic acid sequence. In some aspects, the moiety allows direct covalent attachment of the anchor primer sequence to the solid support. In some aspects, the moiety allows indirect or non-covalent attachment of the anchor primer sequence to the solid support. In some aspects, the moiety comprises an azide. In some aspects, the moiety comprises an alkyne. In some aspects, the moiety comprises a dibenzocyclooctyne (DBCO). In some aspects, the moiety comprises a biotin. In some aspects, the spacer comprises a polyethylene glycol (PEG). In some aspects, the release element or the distal sequence comprises a deoxyuridine. In some aspects, the release element or the distal sequence comprises a penultimate deoxyinosine at a 5' end of the release element, the distal sequence or the nucleic acid sequence. In some aspects, the release element or the distal sequence comprises an abasic deoxyribose. In some aspects, the release element or the distal sequence comprises a Type II S endonuclease site, an offset cutter endonuclease site, or a restriction endonuclease site. In some aspects, the release element or the distal sequence comprises a restriction endonuclease site. In some aspects, the release element or the distal sequence comprises a MlyI restriction endonuclease site. In some aspects, the release element or the distal sequence comprises a sequence capable be being cleaved by a single-stranded specific Cas9 endonuclease.

In some aspects of the compositions of the disclosure, the anchor primer sequence or the nucleic acid sequence comprising the anchor primer sequence has minimal secondary structure. In some aspects, the anchor primer sequence comprises a long homopolymeric tract or a simple bipolymeric tract. In some aspects, the e anchor primer sequence comprises a long bi-polymeric tract comprising a form $[CT]_N$.

In some aspects of the compositions of the disclosure, the composition comprises a plurality of nucleic acid sequences comprising an anchor primer sequence or a plurality of anchor primer sequences, wherein at least one nucleic acid sequence of the plurality of nucleic acid sequences or at least one anchor primer sequence of the plurality of anchor primer sequences comprises a NA sequence or an N-mer of the disclosure. In some aspects, each nucleic acid sequence of the plurality of nucleic acid sequences or each anchor primer sequence of the plurality of anchor primer sequences comprises a NA sequence or an N-mer of the composition. In some aspects, the anchor primer sequence of the at least one nucleotide sequence or of each nucleotide of the plurality of nucleic acid sequences comprising an anchor primer sequence has been extended to comprise the NA sequence or an N-mer of the disclosure. In some aspects, the at least one anchor primer sequence or each anchor primer sequence of the plurality of anchor primer sequences has been extended to comprise the NA sequence or an N-mer of the disclosure. In some aspects, the composition comprises a plurality of 64, 256, 1024 or 1344 unique nucleic acid sequences. In some aspects, the composition comprises a plurality of 64, 256, 1024 or 1344 unique nucleic acid sequences. In some aspects, each unique nucleic acid sequence comprises a monophosphate at a 3' end or at a 5' end. In some aspects, the each unique nucleic acid sequence comprises a hydroxyl group at a 3' end or at a 5' end.

The disclosure provides a composition comprising a solid support for the attachment of an anchor primer sequence or a plurality of anchor primer sequences. In some aspects, the solid support comprises a plurality of monodispersed beads. In some aspects, each of the plurality of monodispersed beads comprise polyacrylamide. In some aspects, each of the plurality of monodispersed beads comprise agarose. In some aspects, each of the plurality of monodispersed beads comprise polystyrene. In some aspects, each of the plurality of monodispersed beads comprise ferromagnetic particles. In some aspects, the solid support comprises a well or chamber. In some aspects, the solid support comprises a plurality of wells or chambers. In some aspects, the plurality of wells comprises a multi-well plate. In some aspects, the solid support comprises a glass. In some aspects, the solid support comprises a glass slide. In some aspects, the solid support comprises a quartz. In some aspects, the solid support comprises a quartz slide. In some aspects, the solid support comprises a polystyrene. In some aspects, the solid support comprises a polystyrene slide. In some aspects, the solid support comprises a coating and wherein the coating prevents non-specific binding of unwanted proteins, unwanted nucleic acids or other unwanted biomolecules. In some aspects, the coating comprises polyethylene glycol (PEG). In some aspects, the coating comprises triethylene glycol (TEG).

The disclosure provides a composition comprising an enzyme, one or more reaction components and specific N-mer substrates, wherein each N-mer substrate is capable of one and only one unit extension from either a 3' end or 5' end of an anchor primer in a geometric NA synthesis reaction. In some aspects, the one or more reaction components comprise potassium acetate, tris-acetate, magnesium acetate or bovine serum albumin. In some aspects, the one or more reaction components comprise polyethylene glycol 8000, hexamine cobalt chloride or adenosine triphosphate. In some aspects, the enzyme is selected from the group consisting of a ribozyme, a T4 RNA ligase, a T4 DNA ligase, a calf intestinal alkaline phosphatase, a shrimp alkaline phosphatase, a Klenow large fragment (3'-5' exonuclease), a lambda exonuclease (5'-3' exonuclease), a polynucleotide kinase, a terminal deoxynucleotidyl transferase (TdT), a DNA polymerase theta, an endonuclease V, an uracil DNA glycosylase, an endonuclease VIII, a 5' deadenylase or a transposase. In some aspects, the enzyme is a ribozyme. In some aspects, the transposase is a piggyBac transposase, a sleeping beauty transposase, or a Tn10 transposase. In some aspects, the enzyme comprises a mutation or a sequence variation having a desired new or a selectively eliminated activity.

The disclosure provides a composition comprising any nucleic acid sequence derived from 3' extension geometric synthesis, 5' extension geometric synthesis, 3' extension parallel synthesis or 5'3' co-synthesis.

The disclosure provides a composition, wherein each NA sequence of arbitrary length capable of participating in geometric synthesis or parallel synthesis reactions comprises DNA, RNA or a combination thereof. In some aspects, the NA sequence comprises a 5' terminal base that is a DNA base and a 3' terminal base that is an RNA base. In some aspects, either or both the 5' and 3' terminal nucleotides of each NA sequence possesses a reversible dimethoxytrityl-phosphate group. In some aspects, each NA sequence possesses an arbitrary number of DNA or RNA nucleotides in an arbitrary order.

The disclosure provides a vector comprising a composition of the disclosure. In some aspects, the vector further comprises a 5' inverted terminal repeat (ITR) and a 3' ITR. In some aspects, from 5' to 3', the vector comprises the 5' ITR, a least one N-mer sequence, and the 3' ITR. In some aspects, the vector further comprises a selectable marker. In some aspects, the selectable marker comprise a sequence encoding an antibiotic resistance gene. In some aspects, the sequence encoding an antibiotic resistance gene comprises a sequence encoding an ampicillin resistance gene.

The disclosure provides a composition comprising a vector of the disclosure.

The disclosure provides a method comprising: a) contacting at least one first plurality of solid supports and at least one first plurality of anchor primers, under conditions that allow for the attachment of a 3' terminus of at least one anchor primer of the at least one first plurality of anchor primers to at least one solid support of the at least one first plurality of solid supports to produce at least one first anchor primer-substrate complex; b) contacting the at least one first anchor primer-substrate complex and at least one first plurality of N-mers under conditions that append a 3' terminus of at least one N-mer of the at least one first plurality of N-mers to a 5' terminus of the at least one first anchor primer-substrate to produce at least one first extended anchor primer-substrate complex; c) contacting the at least one first extended anchor primer-substrate complex and at least one second plurality of N-mers under conditions that append a 3' terminus of at least one N-Mer of the at least one second plurality of N-mers to a 5' terminus of the at least one first extended anchor primer-substrate complex to produce at least one first donor complex; d) contacting at least one second plurality of solid supports and at least one second plurality of anchor primers, under conditions that allow for the attachment of a 3' terminus of at least one anchor primer of the at least one second plurality of anchor primers to at least one solid support of the at least one second plurality of solid supports to produce at least one second anchor primer-substrate complex; e) contacting the at least one second anchor primer-substrate complex and at least one third plurality of N-mers under conditions that append a 3' terminus of at least one N-mer of the at least one third plurality of N-mers to a 5' terminus of the at least one second anchor primer-substrate to produce at least one second extended anchor primer-substrate complex; f) contacting the at least one second extended anchor primer-substrate complex and at least one fourth plurality of N-mers under conditions that append a 3' terminus of at least one N-mer of the at least one fourth plurality of N-mers to a 5' terminus of the at least one second extended anchor primer-substrate complex to produce at least one first target complex; g) releasing at least one composition comprising the at least one N-mer of the at least one first plurality of N-mers and the at least one N-mer of the at least one second plurality of N-mers from the at least one first donor complex to produce at least one released intermediate complex; and h) contacting the at least one first target complex and the at least one released intermediate complex under conditions that append a 3' terminus of the at least one released intermediate complex to a 5' terminus of the at least one target complex to produce at least one first extended target complex.

In some aspects of the methods of the disclosure, appending comprises enzymatic ligation under conditions that allow for ligase activity. In some aspects, appending comprises ligation that is not enzymatic. In some aspects, the enzymatic ligation comprises T4 RNA ligase activity.

In some aspects of the methods of the disclosure, the method further comprises, after the production of the at least one first anchor primer-substrate complex, removing at least one unattached anchor primer.

In some aspects of the methods of the disclosure, the method further comprises, prior to removing the at least one unattached anchor primer, de-adenylating the at least one first anchor primer-substrate complex.

In some aspects of the methods of the disclosure, the method further comprises, after the production of the at least one second anchor primer-substrate complex, removing unattached anchor primers.

In some aspects of the methods of the disclosure, the method further comprises, prior to removing the at least one unattached anchor primer, de-adenylating the at least one second anchor primer-substrate complex.

In some aspects of the methods of the disclosure, removing the at least one unattached anchor primer comprises an exonuclease activity. In some aspects, the exonuclease comprises a 5' to 3' specific exonuclease. In some aspects, the 5' to 3' exonuclease cannot digest nucleic acid molecules comprising a 5' OH group.

In some aspects of the methods of the disclosure, the method further comprises, after production of the at least one first extended anchor primer-substrate complex, removing at least one un-appended N-mer.

In some aspects of the methods of the disclosure, the method further comprises, prior to removing the at least one un-appended N-mer, de-adenylating the at least one first extended anchor primer-substrate complex.

In some aspects of the methods of the disclosure, the method further comprises, after production of the at least one first donor complex, removing at least one un-appended N-mer.

In some aspects of the methods of the disclosure, the method further comprises, prior to removing the at least one un-appended N-mer, de-adenylating the at least one first donor complex.

In some aspects of the methods of the disclosure, the method further comprises, after production of the at least one second extended anchor primer-substrate complex, removing at least one un-appended N-mer.

In some aspects of the methods of the disclosure, the method further comprises, prior to removing the at least one un-appended N-mer, de-adenylating the at least one second extended anchor primer-substrate complex.

In some aspects of the methods of the disclosure, the method further comprises, after production of the at least one first target complex, removing at least one un-appended N-mer.

In some aspects of the methods of the disclosure, the method further comprises, prior to removing the at least one un-appended N-mer, de-adenylating the at least one first target complex.

In some aspects of the methods of the disclosure, the method further comprises, after production of the at least one first extended target complex, removing at least one un-appended N-mer.

In some aspects of the methods of the disclosure, the method further comprises, prior to removing the at least one un-appended N-mer, de-adenylating the at least one first extended target complex.

In some aspects of the methods of the disclosure, removing the at least one un-appended N-mer comprises an exonuclease activity. In some aspects, the exonuclease comprises a 5' to 3' specific exonuclease. In some aspects, the 5' to 3' exonuclease cannot digest nucleic acid molecules comprising a 5' OH group. In some aspects, the 5' to 3' exonuclease comprises a lambda exonuclease, a XRN-1 exonuclease or a combination thereof.

In some aspects of the methods of the disclosure, de-adenylating comprises an enzymatic activity. In some aspects, the enzymatic activity comprises a deadenylase activity. In some aspects, the deadenylase comprises a *S. cerevisiae* 5' deadenylase.

In some aspects of the methods of the disclosure, de-adenylating comprises a non-enzymatic activity.

In some aspects of the methods of the disclosure, the at least one first plurality of N-mers, the at least one second plurality of N-mers, the at least one third plurality of N-mers, the at least one fourth plurality of N-mers or any combination thereof comprise(s) at least one N-mer comprising an OH group at the 3' terminus and the 5' terminus of the N-mer.

In some aspects of the methods of the disclosure, the method further comprises, after production of the at least one first extended anchor primer-substrate complex and before contacting the at least one first extended anchor primer-substrate complex with at least one second plurality of N-mers, appending a $PO_4$ group to the 5' end of at least one N-mer of the at least one first plurality of N-mers.

In some aspects of the methods of the disclosure, the method further comprises, after producing the at least one second extended anchor primer-substrate complex and before contacting the at least one second extended anchor primer-substrate complex and at least one fourth plurality of N-mers, appending a $PO_4$ group to the 5' end of at least one N-mer of the at least one third plurality of N-mers.

In some aspects of the methods of the disclosure, the method further comprises, prior to contacting the at least one first target complex and the at least one released intermediate complex, appending a $PO_4$ group to the 5' end of at least one N-mer of the at least one fourth plurality of N-mers.

In some aspects of the methods of the disclosure, appending a $PO_4$ group comprises enzymatic phosphorylation. In some aspects, the enzymatic phosphorylation comprises T4 polynucleotide kinase activity.

In some aspects of the methods of the disclosure, appending a $PO_4$ group comprises non-enzymatic phosphorylation.

In some aspects of the methods of the disclosure, releasing the at least one composition occurs under conditions that preserve the OH group at the 3' terminus and the OH group at the 5' terminus of the at least one N-mer.

In some aspects of the methods of the disclosure, the at least one first plurality of N-mers, the at least one second plurality of N-mers, the at least one third plurality of N-mers, the at least one fourth plurality of N-mers or any combination thereof comprise(s) at least one N-mer comprising an OH group at the 3' terminus and a $PO_4$ group at the 5' terminus of the N-mer.

In some aspects of the methods of the disclosure, the $PO_4$ group is operably-linked to a protecting group. In some aspects, the protecting group comprises 4,4'-dimethoxytrityl phosphate.

In some aspects of the methods of the disclosure, the method further comprises, after production of the at least one first extended anchor primer-substrate complex and before the production of the at least one first donor complex, removing the protecting group from the at least one first extended anchor primer-substrate complex.

In some aspects of the methods of the disclosure, the method further comprises, after production of the at least one second extended anchor primer-substrate complex and before the production of the at least one first target complex, removing the protecting group from the at least one second extended anchor primer-substrate complex.

In some aspects of the methods of the disclosure, the method further comprises, before production of the at least one first extended target complex, removing the protecting group from the at least one first target complex.

In some aspects of the methods of the disclosure, releasing the at least one composition occurs under conditions that preserve the OH group at the 3' terminus and the $PO_4$ group at the 5' terminus of the N-mer.

In some aspects of the methods of the disclosure, the method further comprises, after production of the at least one first extended anchor primer-substrate complex and before the production of the at least one first donor complex, adenylating the 5' terminus of the at least one first extended anchor primer-substrate complex.

In some aspects of the methods of the disclosure, the method further comprises, after production of the at least one second extended anchor primer-substrate complex and before the production of the at least one first target complex, adenylating the 5' terminus of the at least one second extended anchor primer-substrate complex.

In some aspects of the methods of the disclosure, the method further comprises, before production of the at least one first extended target complex, adenylating the 5' terminus of the at least one first target complex.

In some aspects of the methods of the disclosure, adenylating comprises enzymatic activity. In some aspects, enzymatic activity comprises an Mth RNA ligase activity.

In some aspects of the methods of the disclosure, adenylation comprises non-enzymatic activity.

The disclosure provides a method comprising: a) contacting at least one first plurality of solid supports and at least one first plurality of anchor primers, under conditions that allow for the attachment of a 5' terminus of at least one anchor primer of the at least one first plurality of anchor primers to at least one solid support of the at least one first plurality of solid supports to produce at least one first anchor primer-substrate complex; b) contacting the at least one first anchor primer-substrate complex and at least one first plurality of N-mers under conditions that append a 5' terminus of at least one N-mer of the at least one first plurality of N-mers to a 3' terminus of the at least one first anchor primer-substrate to produce at least one first extended anchor primer-substrate complex; c) contacting the at least one first extended anchor primer-substrate complex and at least one second plurality of N-mers under conditions that append a 5' terminus of at least one N-mer of the at least one second plurality of N-mers to a 3' terminus of the at least one first extended anchor primer-substrate complex to produce at least one first donor complex; d) contacting at least one second plurality of solid supports and at least one second plurality of anchor primers, under conditions that allow for the attachment of a 5' terminus of at least one anchor primer of the at least one second plurality of anchor primers to at least one solid support of the at least one second plurality of solid supports to produce at least one second anchor primer-substrate complex; e) contacting the at least one second anchor primer-substrate complex and at least one third plurality of N-mers under conditions that append a 5' terminus of at least one N-mer of the at least one third plurality of N-mers to a 3' terminus of the at least one second anchor primer-substrate to produce at least one second extended anchor primer-substrate complex; f) contacting the at least one second extended anchor primer-substrate complex and at least one fourth plurality of N-mers under conditions that append a 5' terminus of at least one N-mer of the at least one fourth plurality of N-mers to a 3' terminus of the at least one second extended anchor primer-substrate complex to produce at least one first target complex; g) releasing at least one composition comprising the at least one N-mer of the at least one first plurality of N-mers and the at least one N-mer of the at least one second plurality of N-mers from the at least one first donor complex to produce at least one released intermediate complex h) contacting the at least one first target complex and the at least one released intermediate complex under conditions that append a 5' terminus of the at least one released intermediate complex to a 3' terminus of the at least one target complex to produce at least one first extended target complex.

In some aspects of the methods of the disclosure, appending comprises enzymatic ligation under conditions that allow for ligase activity. In some aspects, enzymatic ligation comprises a T4 RNA ligase activity.

In some aspects of the methods of the disclosure, appending comprises ligation that is not enzymatic.

In some aspects of the methods of the disclosure, the method comprises, after the production of the at least one first anchor primer-substrate complex, removing at least one unattached anchor primer.

In some aspects of the methods of the disclosure, the method further comprises, after the production of the at least one second anchor primer-substrate complex, removing at least one unattached anchor primer.

In some aspects of the methods of the disclosure, removing the at least one unattached anchor primer comprises an exonuclease activity. In some aspects, the exonuclease comprises a 3' to 5' specific exonuclease. In some aspects, the 3' to 5' exonuclease cannot digest nucleic acid molecules comprising a 3' $PO_4$ group.

In some aspects of the methods of the disclosure, the method further comprises, after production of the at least one first extended anchor primer-substrate complex, removing at least one un-appended N-mer.

In some aspects of the methods of the disclosure, the method further comprises, after production of the at least one donor complex, removing at least one un-appended N-mer.

In some aspects of the methods of the disclosure, the method further comprises, after production of the at least one second extended anchor primer-substrate complex, removing at least one un-appended N-mer.

In some aspects of the methods of the disclosure, the method further comprises, after production of the at least one target complex, removing at least one un-appended N-mer.

In some aspects of the methods of the disclosure, the method further comprises, after production of the at least one first extended target complex, removing at least one un-appended N-mer.

In some aspects of the methods of the disclosure, removing the at least one un-appended N-mer comprises an exonuclease activity. In some aspects, the exonuclease comprises a 3' to 5' specific exonuclease. In some aspects, the 3' to 5' exonuclease cannot digest nucleic acid molecules comprising a 3' $PO_4$ group. In some aspects, the 3' to 5' exonuclease comprises a Klenow polymerase.

In some aspects of the methods of the disclosure, the at least one first plurality of N-mers, the at least one second plurality of N-mers, the at least one third plurality of N-mers, the at least one fourth plurality of N-mers or any combination thereof comprise(s) at least one N-mer comprising a $PO_4$ group at the 3' terminus and the 5' terminus of the N-mer.

In some aspects of the methods of the disclosure, the method further comprises, after production of the at least one first extended anchor primer-substrate complex and before the production of the at least one first donor complex, removing the $PO_4$ group at the 3' terminus of the at least one first extended anchor primer-substrate complex.

In some aspects of the methods of the disclosure, the method further comprises, after production of the at least one second extended anchor primer-substrate complex and before the production of the at least one first target complex, removing the $PO_4$ group at the 3' terminus of the at least one first extended anchor primer-substrate complex.

In some aspects of the methods of the disclosure, the method further comprises, before production of the at least one first extended target complex, removing the $PO_4$ group at the 3' terminus of the at least one first target complex.

In some aspects of the methods of the disclosure, removing the $PO_4$ group comprises enzymatic phosphatase activity. In some aspects, the enzymatic phosphatase activity comprises calf intestinal alkaline phosphatase (CIP) activity, shrimp alkaline phosphatase (SAP) activity or any combination thereof.

In some aspects of the methods of the disclosure, removing the $PO_4$ group comprises non-enzymatic phosphatase activity.

The disclosure provides a method comprising, a) providing a first composition comprising a first plurality of anchor primers, wherein a 5' terminus of at least one anchor primer is operably-linked to at least one solid substrate and wherein the at least one anchor primer comprises a reversible blocking group at a 3' terminus to form a first blocked anchor primer-substrate complex and a second composition comprising at least a second plurality of anchor primers, wherein a 5' terminus of at least one anchor primer is operably-linked to at least one solid substrate and wherein the at least one anchor primer comprises a reversible blocking group at a 3' terminus to form a second blocked anchor primer-substrate complex, b) removing the reversible blocking group from either the first blocked anchor-primer substrate complex or the second anchor-primer substrate complex to produce at least one unblocked anchor primer-substrate complex; c) contacting the unblocked anchor primer-substrate complex and at least one first plurality of N-mers, each N-mer comprising a reversible blocking group at a 3' terminus of the N-mer, under conditions that append a 5' terminus of at least one N-mer of the at least one first plurality to a 3' terminus of the at least one unblocked anchor primer-substrate complex to form at least one blocked extended anchor primer-substrate complex; d) removing the reversible blocking group from the at least one blocked extended anchor primer-substrate complex to produce at least one unblocked extended anchor primer-substrate complexes; and e) contacting the unblocked extended anchor primer-substrate complex and at least one second plurality of N-mers, each N-mer comprising a reversible blocking group at a 3' terminus of the N-mer, under conditions that append a 5' terminus of at least one N-mer of the at least one first plurality to a 3' terminus of the at least one unblocked extended anchor primer-substrate complex to form at least one blocked donor complex.

In some aspects of the methods of the disclosure, a portion of the anchor primers of the first plurality of anchor primers are operably linked to at least one solid substrate.

In some aspects of the methods of the disclosure, a portion of the anchor primers of the second plurality of anchor primers are operably linked to at least one solid substrate.

In some aspects of the methods of the disclosure, each anchor primer of the first plurality of anchor primers is operably linked to at least one solid substrate.

In some aspects of the methods of the disclosure, each anchor primer of the second plurality of anchor primers is operably linked to at least one solid substrate.

In some aspects of the methods of the disclosure, each anchor primer of the first plurality of anchor primers is operably linked to a first solid substrate. In some aspects, each anchor primer of the second plurality of anchor primers is operably linked to a second solid substrate. In some aspects, the first substrate and the second substrate are the same. In some aspects, the first substrate and the second substrate are not the same.

In some aspects of the methods of the disclosure, the at least first plurality of anchor primers or the at least second plurality of anchor primers is arranged in an array. In some aspects, the at least first plurality of anchor primers is arranged in a first array and the at least second plurality of anchor primers is arranged in a second array. In some aspects, the first array and the second array are the same. In some aspects, the first array and the second array are not the same.

In some aspects of the methods of the disclosure, the reversible blocking group is a photo-liable blocking group. In some aspects, removing comprises exposing the photo-liable blocking group to light with a wavelength sufficient to induce removal of the photo-liable blocking group.

The disclosure provides a method comprising: a) contacting at least one first plurality of solid supports and at least one first plurality of anchor primers, under conditions that allow for the attachment of a terminus of at least one anchor primer of the at least one first plurality of anchor primers to at least one solid support of the at least one first plurality of solid supports to produce at least one first anchor primer-substrate complex; b) contacting the at least one first anchor primer-substrate complex and at least one first plurality of N-mers under conditions that append at least one N-mers of the at least one first plurality of N-mers to at least one first anchor primer-substrate, wherein at least one N-mer of the at least one first plurality of N-mers comprises a sequence encoding a 5' inverted terminal repeat (ITR) and a sequence encoding a 3' inverted terminal repeat (ITR) that are reverse oriented with respect to each other, to produce at least one first extended anchor primer-substrate complex; c) contacting the at least one first extended anchor primer-substrate complex and at least one second plurality of N-mers under conditions that append at least one N-mer of the at least one second plurality of N-mers to the at least one first extended anchor primer-substrate complex, wherein at least one N-mer of the at least one second plurality of N-mers comprises a sequence encoding a 5' inverted terminal repeat (ITR) and a sequence encoding a 3' inverted terminal repeat (ITR) that are reverse oriented with respect to each other, to produce at least one first elongated complex; d) excising from the at least one first elongated complex a nucleic acid sequence positioned between the 3' reverse-oriented ITR of the at least one N-mer of the at least one first plurality of N-mers and the 5' reverse-oriented ITR of the at least one N-mer of the at least one second plurality of N-mers to produce at least one first donor complex; e) contacting at least one second plurality of solid supports and at least one second plurality of anchor primers, under conditions that allow for the attachment of a terminus of at least one anchor primer of the at least one second plurality of anchor primers to at least one solid support of the at least one second plurality of solid supports to produce at least one second anchor primer-substrate complex; f) contacting the at least one second anchor primer-substrate complex and at least one third plurality of N-mers under conditions that append at least one N-mer of the at least one third plurality of N-mers to at least one second anchor primer-substrate, wherein at least one N-mer of the at least one third plurality of N-mers comprises a sequence encoding a 5' inverted terminal repeat (ITR) and a sequence encoding a 3' inverted terminal repeat (ITR) that are reverse oriented with respect to each other, to produce at least one second extended anchor primer-substrate complex; g) contacting the at least one second extended anchor primer-substrate complex and at least one fourth plurality of N-mers under conditions that append at least one N-mer of that at least one fourth plurality of N-mers to the at least one second extended anchor primer-substrate complex, wherein at least one N-mer of the at least one fourth plurality of N-mers comprises a sequence encoding a 5' inverted terminal repeat (ITR) and a sequence encoding a 3' inverted terminal repeat (ITR) that are reverse oriented with respect to each other, to produce at least one second elongated complex; h) releasing a composition comprising the 5' reverse oriented ITR, the at least one N-mer of the at least one first plurality of N-mers, the at least one second plurality of N-mers, and a 3' reverse oriented ITR of the at least one first donor complex to produce at least one released intermediate complex; i) contacting the at least one first target complex and the at least one released intermediate complex under conditions that append the at least one released intermediate complex to the at least one first target complex to produce at least one first extended target complex; and j) excising from the at least one first extended target complex a nucleic acid sequence between the at least one N-mer of the at least one fourth plurality of N-mers and the at least one N-mer of the at least one first plurality of N-mers located to produce at least one first excised extended target complex.

In some aspects of the methods of the disclosure, the sequence encoding the 5' ITR and sequence encoding the 3'ITR of the at least one N-mer are derived from a precisely excising transposable element.

In some aspects of the methods of the disclosure, the releasing comprises an enzymatic activity. In some aspects, the releasing comprises a break in a sequence of one or more of a 3' ITR, a 3' terminus, a 5' terminus, or a 5' ITR. In some aspects, the releasing produces a 5' or a 3' overhang.

In some aspects of the methods of the disclosure, the releasing comprises a non-enzymatic activity.

In some aspects of the methods of the disclosure, the appending comprises an enzymatic activity. In some aspects, the appending comprises a ligation.

In some aspects of the methods of the disclosure, the appending comprises a non-enzymatic activity.

In some aspects of the methods of the disclosure, at least one anchor primer comprises a composition of the disclosure.

The disclosure provides a method comprising: a) providing a template complex that comprises at least one template nucleic acid molecule, wherein a first terminus of the template nucleic acid molecule is operably-linked to a solid support, wherein the first terminus comprises a first primer binding region and, wherein a second terminus of the template nucleic acid molecule comprises a second primer binding region; b) contacting the template complex and at least one first amplification primer, wherein the at least one first amplification primer comprises a nucleic acid sequence that is complementary to the second primer binding region under conditions sufficient for the hybridization of the at least one first amplification primer to the second primer binding region; c) extending the at least one first amplification primer to produce at least one first replicated nucleic acid molecule; d) contacting the at least one first replicated nucleic acid molecule and at least one substrate bound primer complex, wherein the at least one substrate bound primer complex comprises at least one second amplification primer operably-linked to a solid support, wherein the at least one second amplification primer comprises a nucleic acid sequence complementary to the first primer binding region under conditions sufficient for the hybridization of that least one second amplification primer to the at least one first replicated nucleic acid molecule; and e) extending the at least one second amplification primer to produce at least one first replicated duplex.

In some aspects of the methods of the disclosure, at least one solid support comprises a composition of the disclosure.

The disclosure provides a method comprising: (a) contacting a plurality of nucleic acid sequences under conditions suitable for at least a first sequence to form first duplex with a second sequence and the first sequence to form a second duplex with a third sequence, wherein each sequence comprising a first region of complementarity and a second region of complementarity, wherein the first region of complementarity comprises a portion of the sequence that can form a first duplex in the presence of second sequence, wherein the second region of complementarity comprises a portion of sequence that can form a second duplex with a third sequence, wherein the second sequence and the third sequence are distinct; and (b) inducing synthesis from a 3' terminus of at least one sequence of the first duplex or the second duplex under conditions suitable for nucleic acid polymerization to form at least 1 extended sequence.

In some aspects of the methods of the disclosure, the plurality of nucleic acid sequences comprises sense sequences and antisense sequences. In some aspects, the plurality of nucleic acid sequences comprises at least 2 sense sequences or at least 2 antisense sequences. In some aspects, the plurality of nucleic acid sequences comprises at least 2 sense sequences or at least 2 antisense sequences. In some aspects, the method forms at least 2 extended sense sequences or at least 2 extended antisense sequences. In some aspects, the method further comprises appending the at least 2 extended sense sequences or at least 2 extended antisense sequences to form a unified sense strand or a unified antisense strand. In some aspects, the appending comprises an enzymatic activity. In some aspects, the appending comprises a ligation or a ligase activity. In some aspects, the appending comprises a non-enzymatic activity.

In some aspects of the methods of the disclosure, at least one sequence of the plurality of nucleic acid sequences comprises an N-mer. In some aspects, the N-mer is a 3-mer or a 5-mer. In some aspects, at least one sequence of the plurality of nucleic acid sequences is produced according to the method of the disclosure. In some aspects, a portion of the sequences of the plurality of nucleic acid sequences is produced according to the method of the disclosure. In some aspects, each sequences of the plurality of nucleic acid sequences is produced according to the method of the disclosure.

The disclosure provides a nucleic acid sequence produced according to the method of the disclosure.

The disclosure provides a vector comprising a nucleic acid sequence of the disclosure, including those produced according to the method of the disclosure.

The disclosure provides a composition comprising a nucleic acid sequence of the disclosure, including those produced according to the method of the disclosure.

The disclosure provides a composition comprising the vector of the disclosure.

The disclosure provides a cell comprising a nucleic acid sequence of the disclosure, including those produced according to the method of the disclosure.

The disclosure provides a cell comprising the vector of the disclosure.

The disclosure provides a cell comprising the composition of the disclosure.

The disclosure provides a composition comprising a cell of the disclosure.

BRIEF DESCRIPTION OF THE DRAWINGS

FIG. 2A, FIG. 2B, FIG. 2C and FIG. 2D are diagrams showing four different possible anchor primer sequences. FIG. 2A for 3' extension, and FIG. 2B for 5' extension, are examples of low-complexity sequences possessing a Type II S restriction enzyme site, MlyI. FIG. 2C for 3' extension is a low-complexity sequence possessing a dexoyuridine (U) for release using a combination of Uracil DNA glycosylase and DNA glycosylase-lyase Endonuclease VIII. Finally, FIG. 2D shows the combination of deoxyadenosine (A) and deoxyinosine (I) at the 5' end of a low-complexity anchor primer sequence, is a target of Endonuclease V for release of synthetic NA product.

FIG. 3A and FIG. 3B highlight a fragment of GFP cDNA, used in the present disclosure to demonstrate the 3' geometric synthesis method. FIG. 3A shows a FASTA representation of the complete cDNA sequence for green fluorescent protein (GFP) (NCBI accession number L29345). The demonstration fragment comprises the first eight 21-mer sequences. These are highlighted in a range of colors. FIG. 3B shows the distribution of 21-mer sequences into two plate sets for assembly using the 3' geometric synthesis method. The first eight 21-mers are highlighted in the colors corresponding to the FASTA file representation.

Firstly, column transfers (the initial column highlighted in red) take place over 4 cycles (after the initial addition of two N-mers to each well). In the first cycle column 16 well contents serve as donors for column 15, column 14 for column 13 and so on. In the second cycle, wells of column 15 serve as donors for column, etc. On cycle 4, column 9 wells serve as donors for column 1. In the second phase, all of the transfers occur within column 1. Firstly, for Cycle 5, well P1(highlighted in green) serves as donor for well O1, well N1 for well M1 and so on. Ultimately well I1 is the donor for well A1 to yield a final product. If the starting N-mers were all 3-mers the final product would be 1536 bases long. Likewise with 5-mers the final product would be 2560 bases long.

FIG. 10. Size of N-mer can be varied. In 4 cycles 3-mers will generate 96 bases, 4-mers→128 bases and 5-mers→160 bases. Number and length of fragments as well as the size of overlap can be varied. In this example with 6 fragments, 96 bases each and 24 bp overlap, the resulting product would be 456 bp long, 160 base fragments and 24 bp overlap would yield an 840 bp product.

Figure 11:
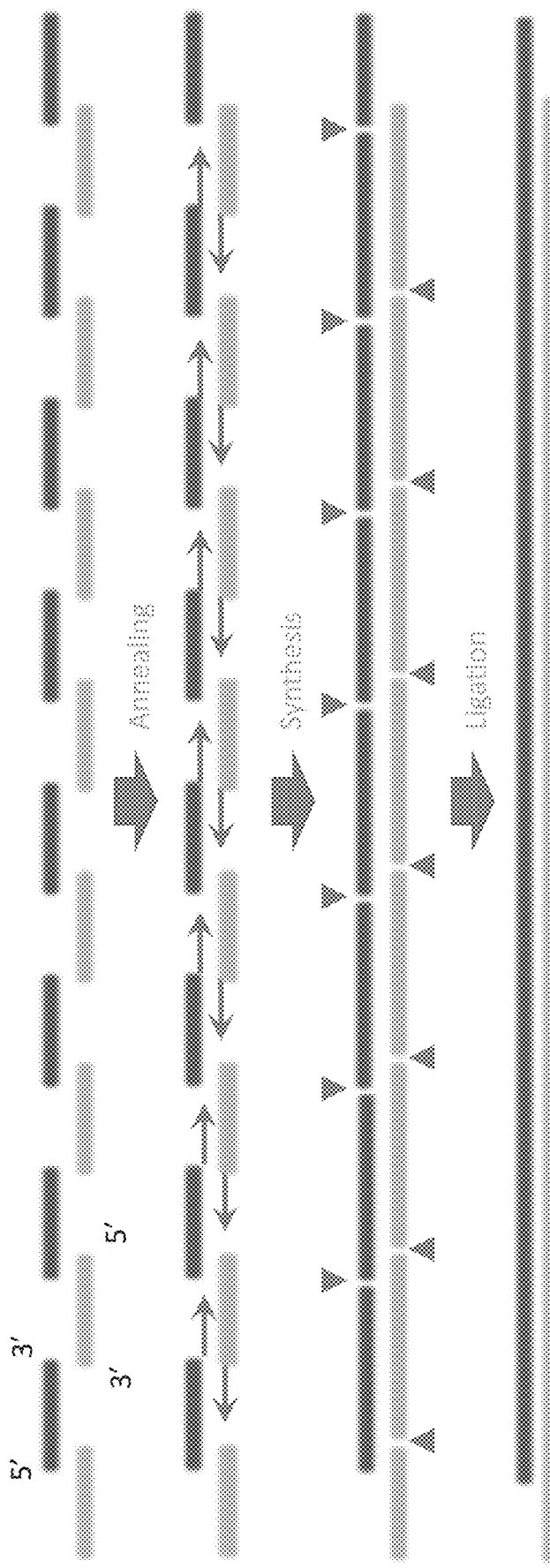

FIG. 11 depicts accelerated long, fast NA synthesis using a mixed 3', 5' co-synthesis with DNA polymerase filling and ligation. In this example, an annealing reaction is carried out with 16 partially overlapping complementary fragments. In a subsequent polymerase reaction, each overlapping 3' end is extended. Finally, in a ligase reaction the breaks between fragments are resolved.

Figure 12:
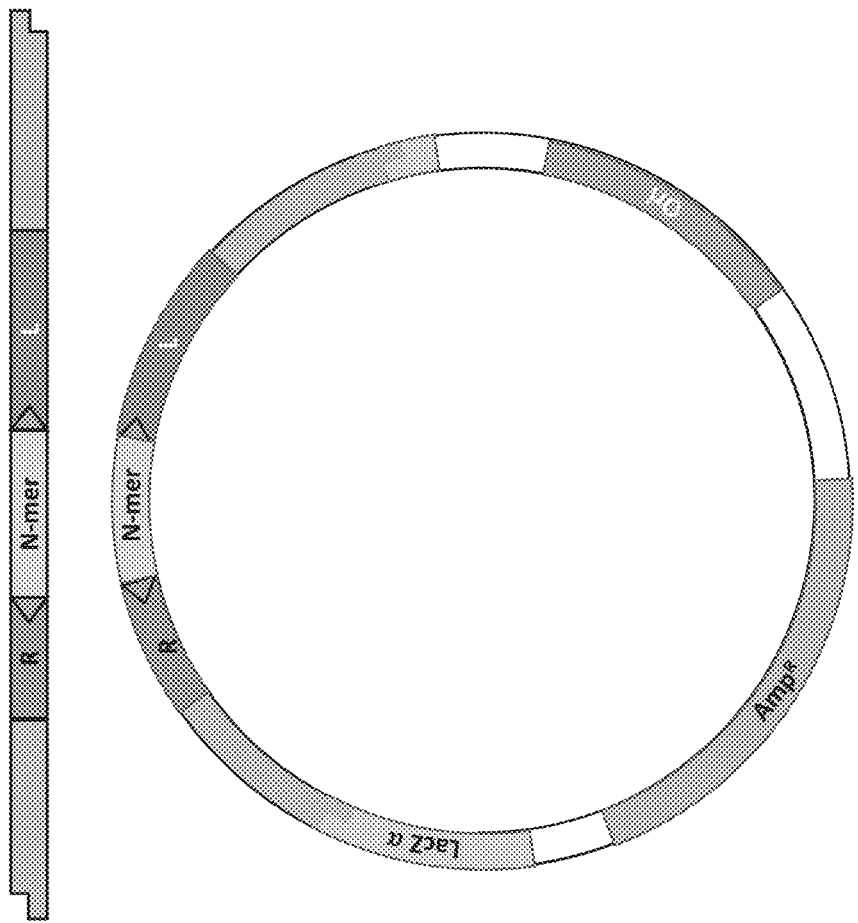

FIG. 12 is a generic plasmid map for transposase mediated geometric synthesis. The plasmid carries a modified transposable element. Instead of the normal orientation of the left (green with purple triangle) and right (red with purple triangle) inverted terminal repeat (ITR) sequences, here the ITRs are reverse oriented with the N-mer sequence between them. Sequence to the left and to the right of the ITRs (grey) is present to fulfill a requirement for a minimal transposable element size plus an appropriate restriction endonuclease site. In addition to the transposable element and N-mer sequences the construct also has a backbone plasmid, such as pUC19 carrying a LacZ alpha gene with a multiple cloning site, an origin of replication and a selectable marker such as an ampicillin resistance gene.

Figure 13:
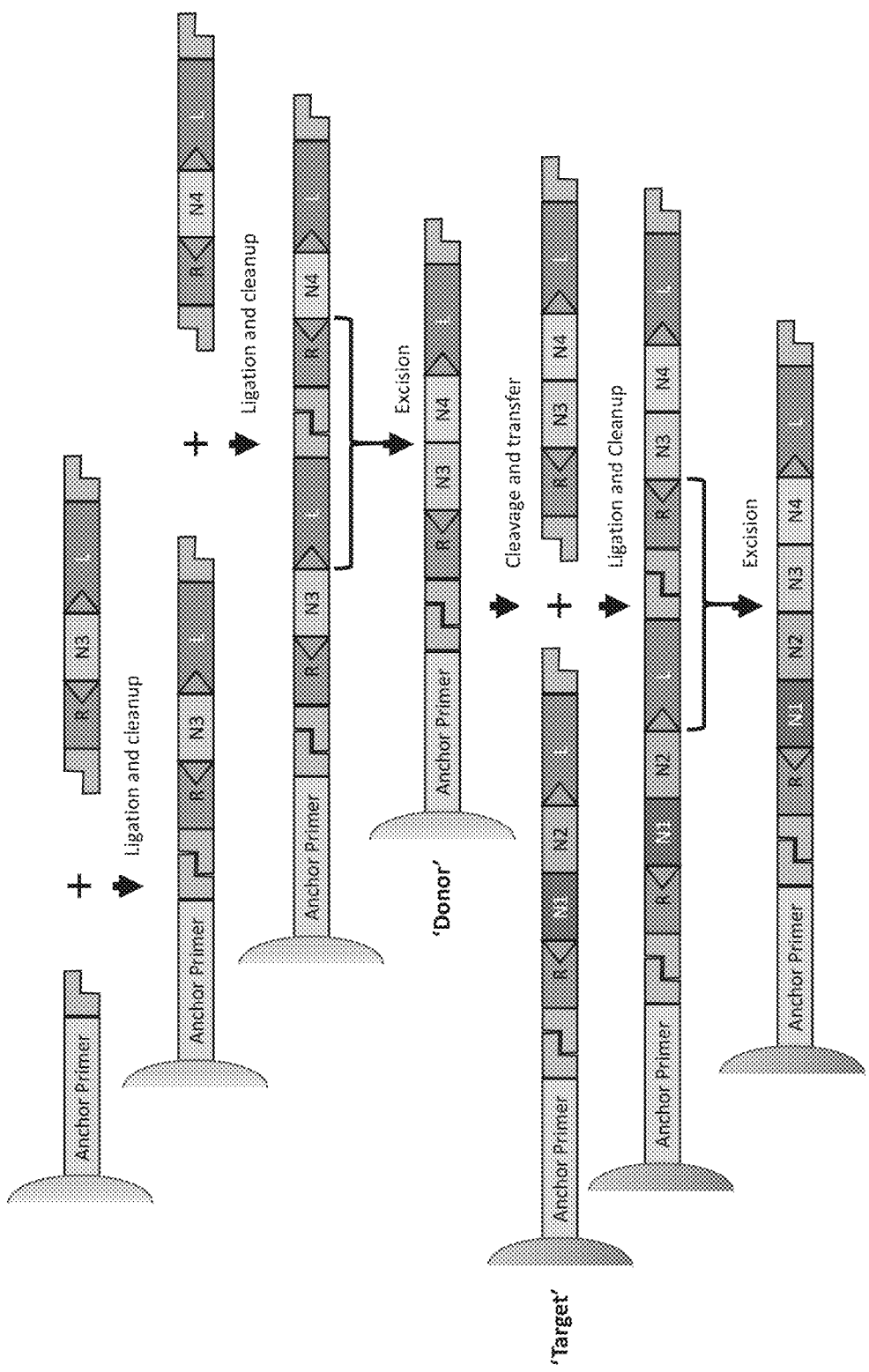

FIG. 13 depicts double stranded DNA geometric synthesis mediated by ligation and the activity of precisely excising transposases. 1) Ligation of an N-mer carrying inverse transposable element onto anchor primers is followed by reaction cleanup. 2) A second N-mer carrying inverse transposable element is then ligated to the extending NA chain on the solid support followed by cleanup. 3) Treatment of the extending NA chain with transposase leads to the excision of the intervening sequence between the two N-mer sequences. 3) The ligated, excised NA chain can be released from the beads by a RE reaction and can then serve as a 'donor' for a subsequent ligation reaction. 4) Cycles of cleavage and transfer, ligation and cleanup, followed by excision using appropriate 'donors' and 'targets' will lead eventually to the desired NA sequence.

Figure 14:
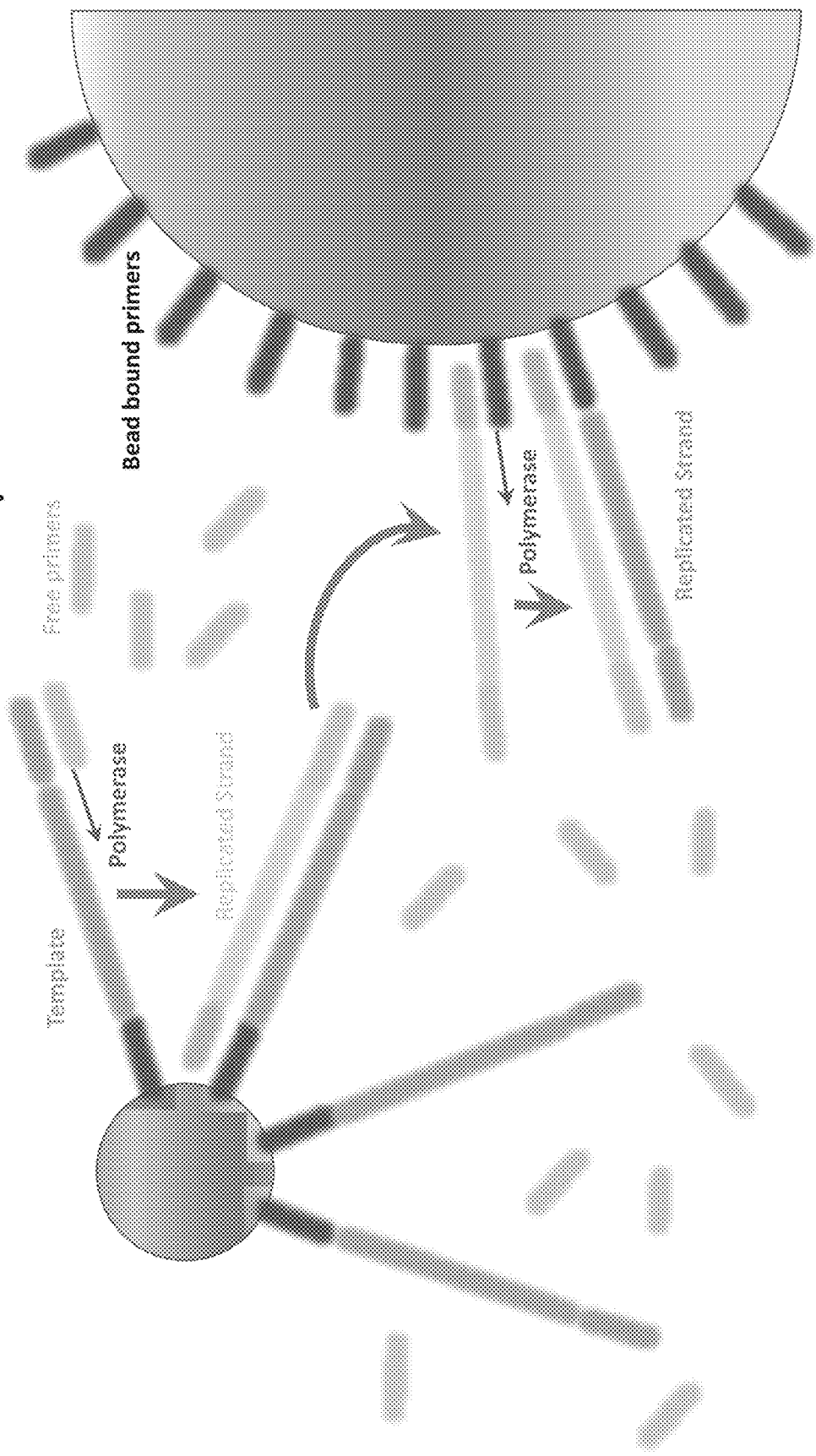

FIG. 14 depicts compositions and methods for the amplification of NAs by surface to surface transfer amplification. In this example, the template (dark pink with a dark green end and a black end) is brought into the reaction on a bead (small blue circle) (donor surface). The template NA molecules (dark pink) bear unique sequences at the proximal end (near the bead, depicted in black) and distal end (away from the bead, depicted in dark green). In the case of a geometric synthesis reaction, the distal unique sequence (dark green) may be ligated onto the template sequence. These sequences are used as targets for primers: black primers attached to the beads (small blue circle and large blue semi-circle), which in the case of geometric synthesis would essentially be the anchor primers, and light green primers that are free in solution. In the amplification reaction, which can be mediated by either PCR or RPA, a polymerase (purple arrow) synthesizing from a template bound free primer (light green) will make a reverse complement copy (light pink with a light green end and a grey end) of the template NA. The replicated strand (copy) released, for example, during the melt phase of a PCR cycle, can then hybridize to acceptor-surface (large blue semi-circle) (acceptor surface) bound primers. The copy strands then serve as templates for new generation of original NA molecules mediated by polymerase synthesizing from surface-bound primers (black).

Figure 15:
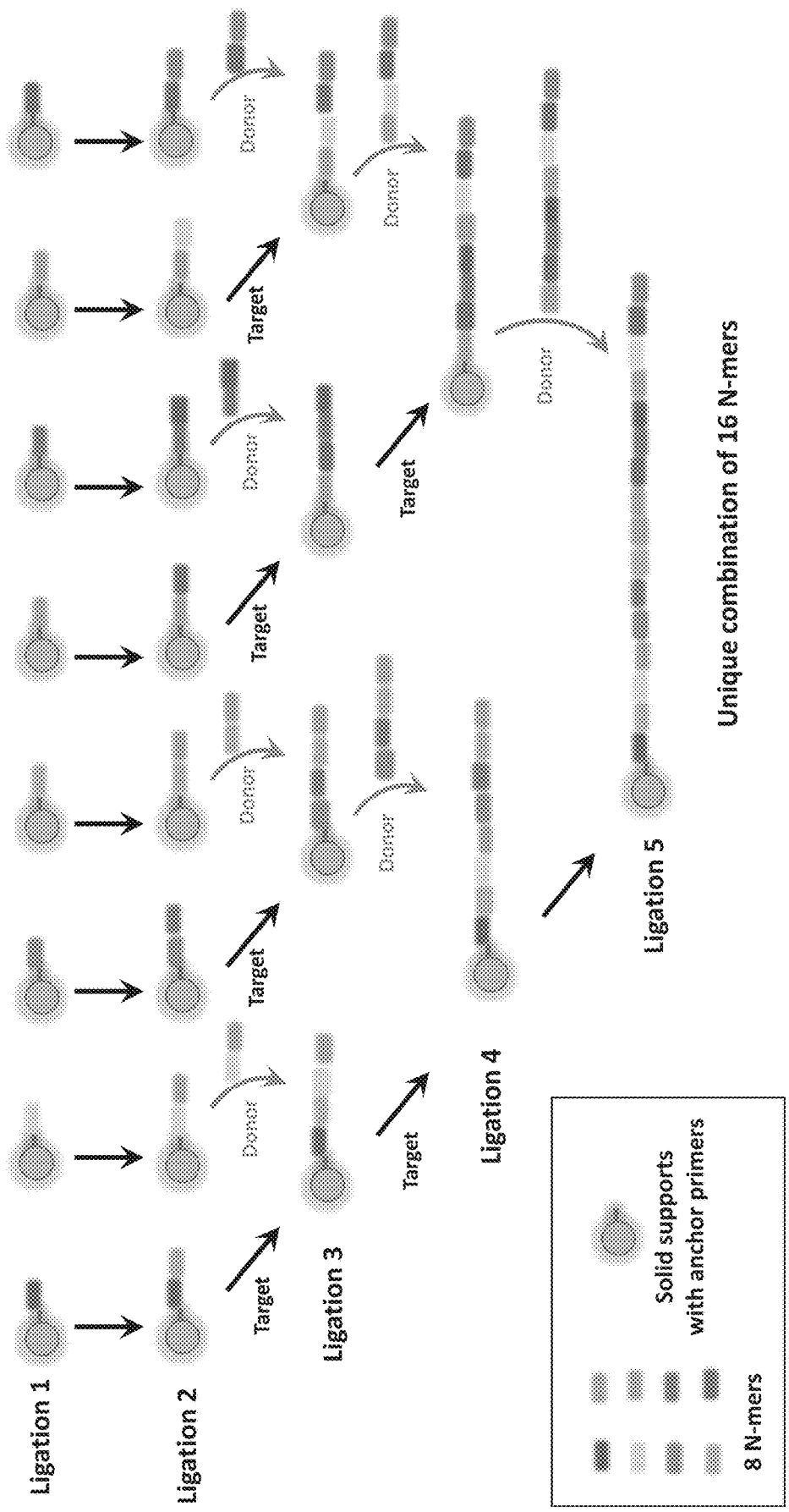

FIG. 15 is a schematic overview of geometric synthesis. In this example, eight different N-mers and the solid substrate bound anchor primer sequences are the starting materials.

FIG. 16A, FIG. 16B, FIG. 16C and FIG. 16D show a schematic overview of the 5' extension geometric synthesis method of the present disclosure.

Figure 17:
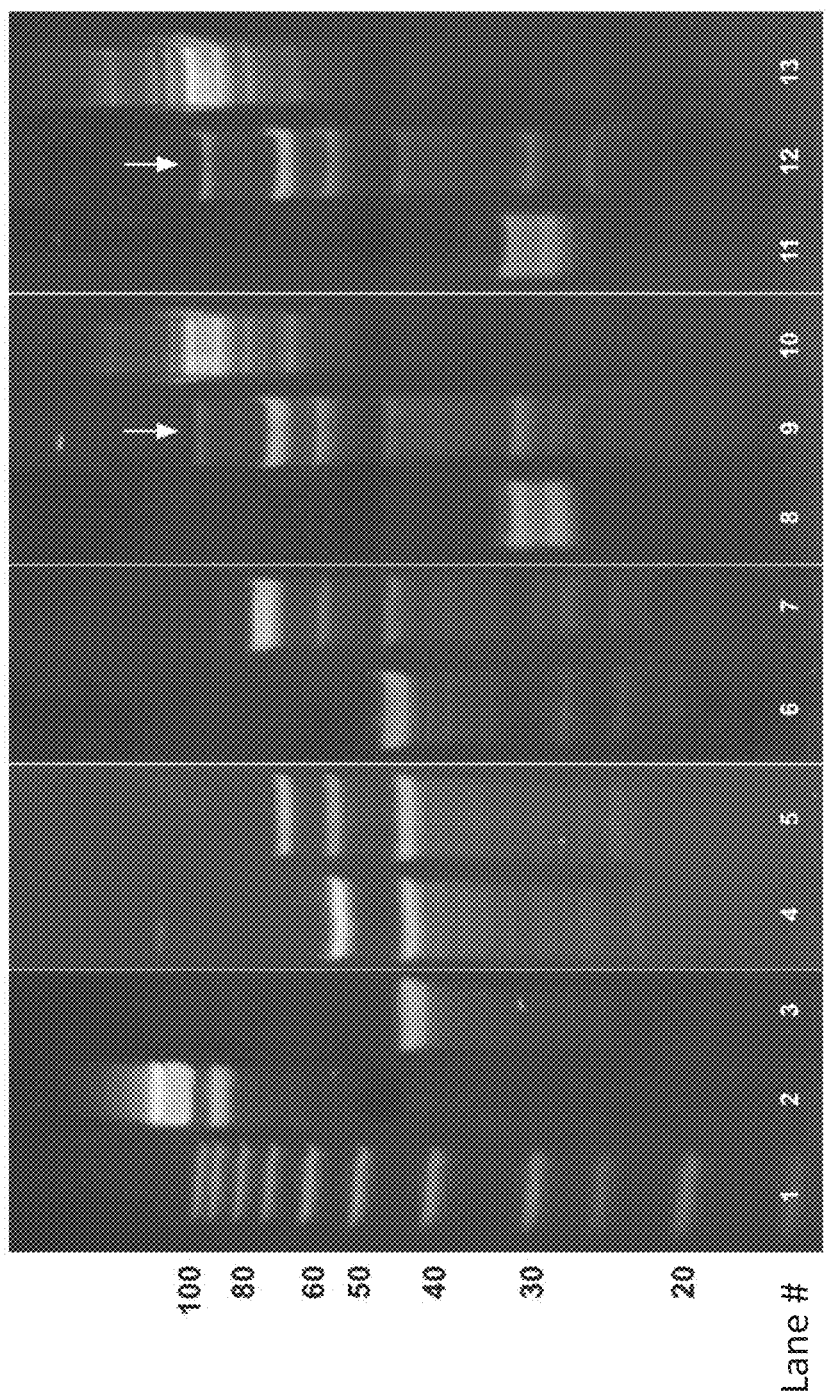

FIG. 17 is an image of a polyacrylamide gel used to analyze the products of the 5' extension geometric synthesis method of the present disclosure.

FIG. 18A, FIG. 18B, FIG. 18C, FIG. 18D, FIG. 18E and FIG. 18F show a schematic overview of the 5' modular linear synthesis method of the present disclosure.

Figure 19:
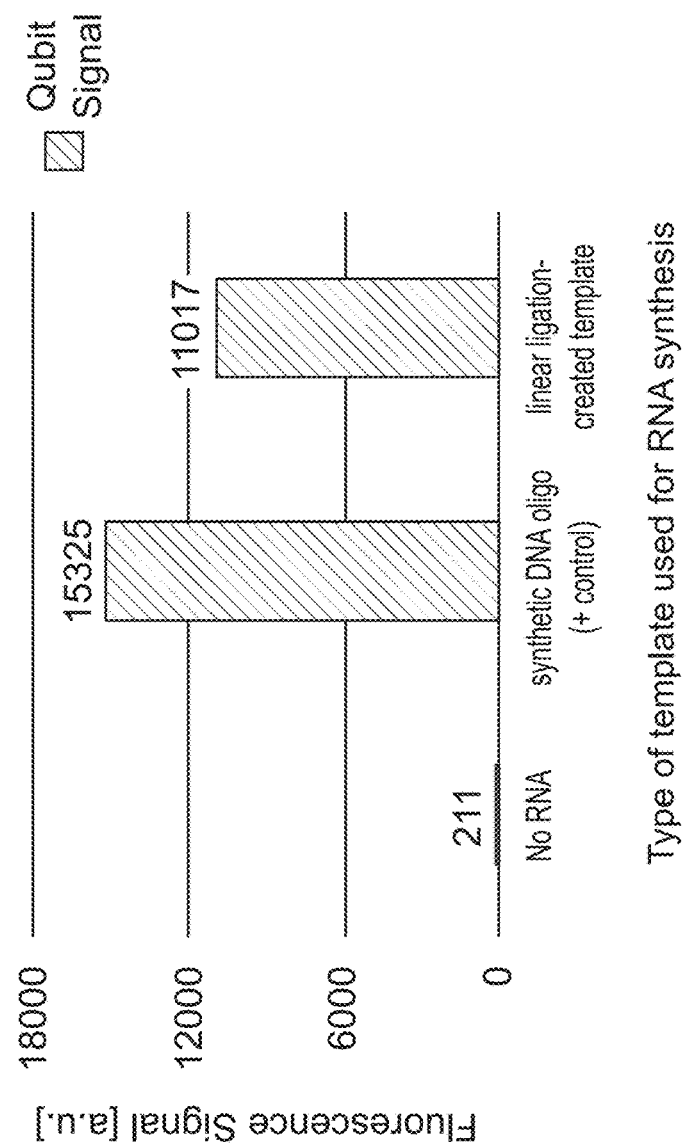

FIG. 19 is a chart and an image demonstrating that a Baby Spinach RNA aptamer synthesized using the methods of the present disclosure is active and enhances the fluorescence of DRHBI.

Figure 20:
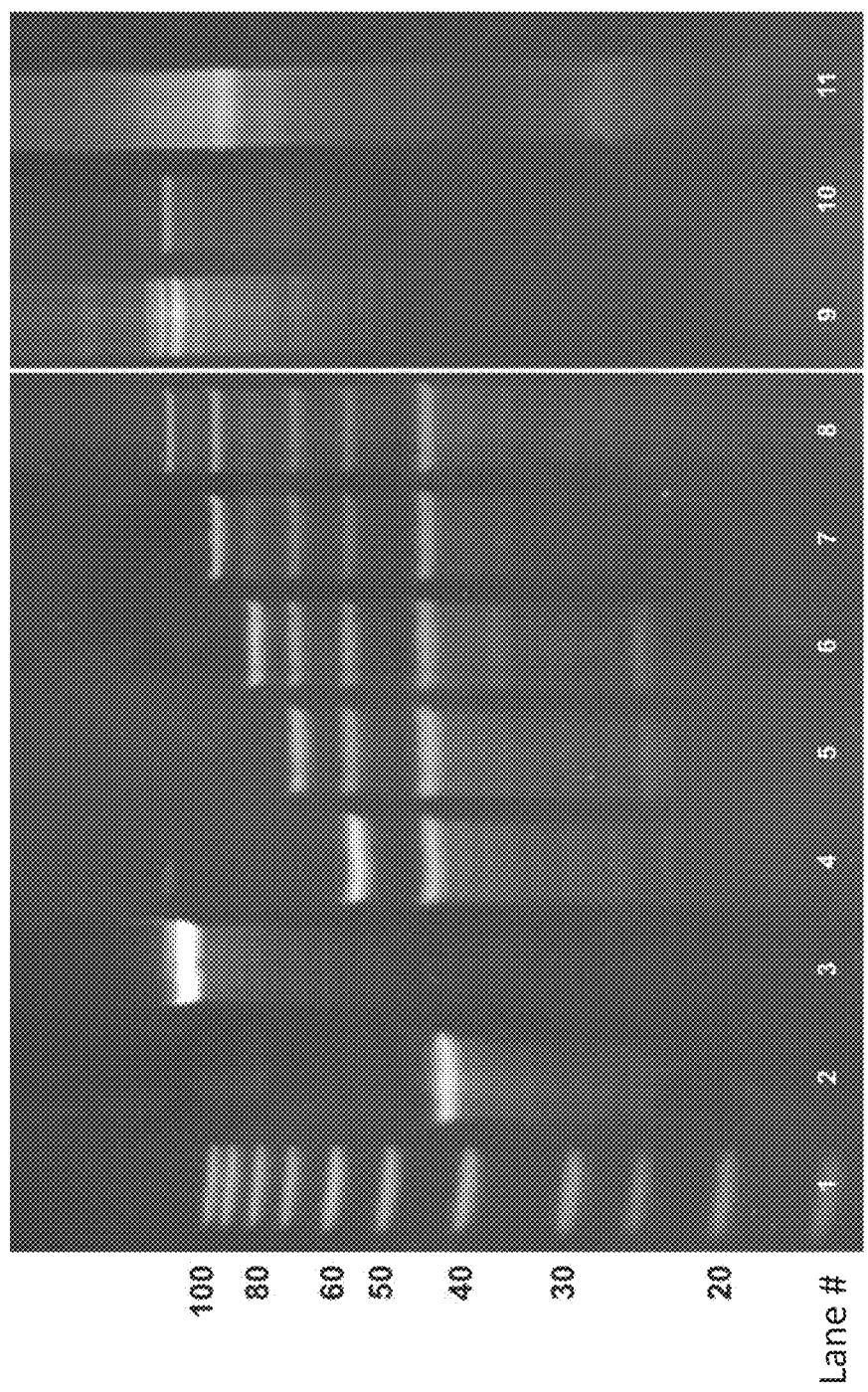

FIG. 20 is an image of a polyacrylamide gel used to analyze the products of the 5' modular linear synthesis method of the present disclosure.

Figure 21:
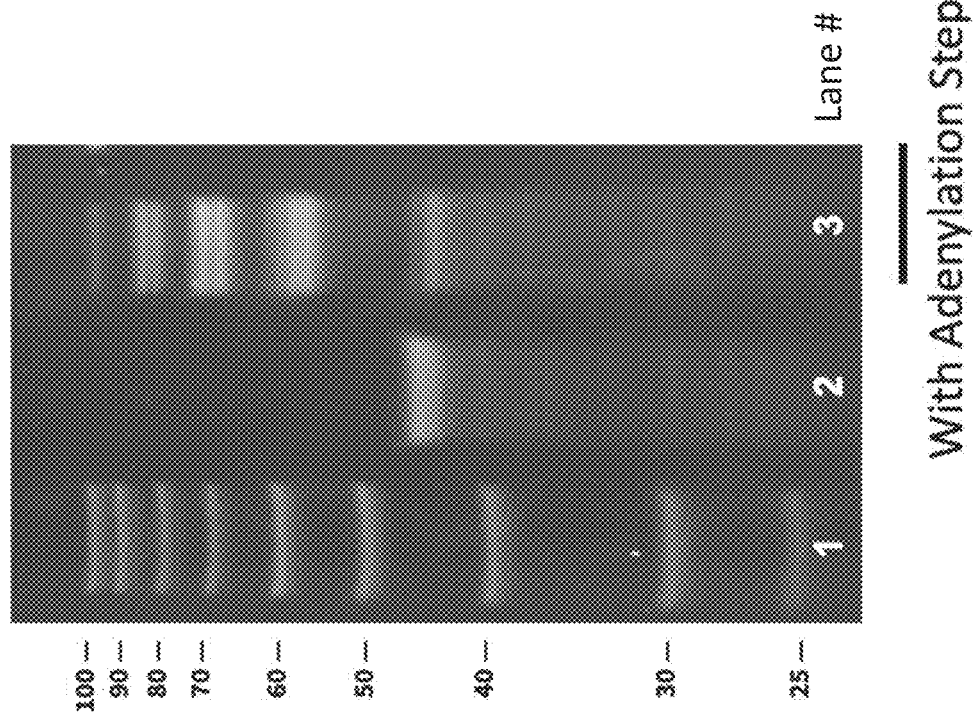

FIG. 21 is an image of a polyacrylamide gel used to analyze the products of the 5' modular linear synthesis method with 5' adenylation.

Figure 22:
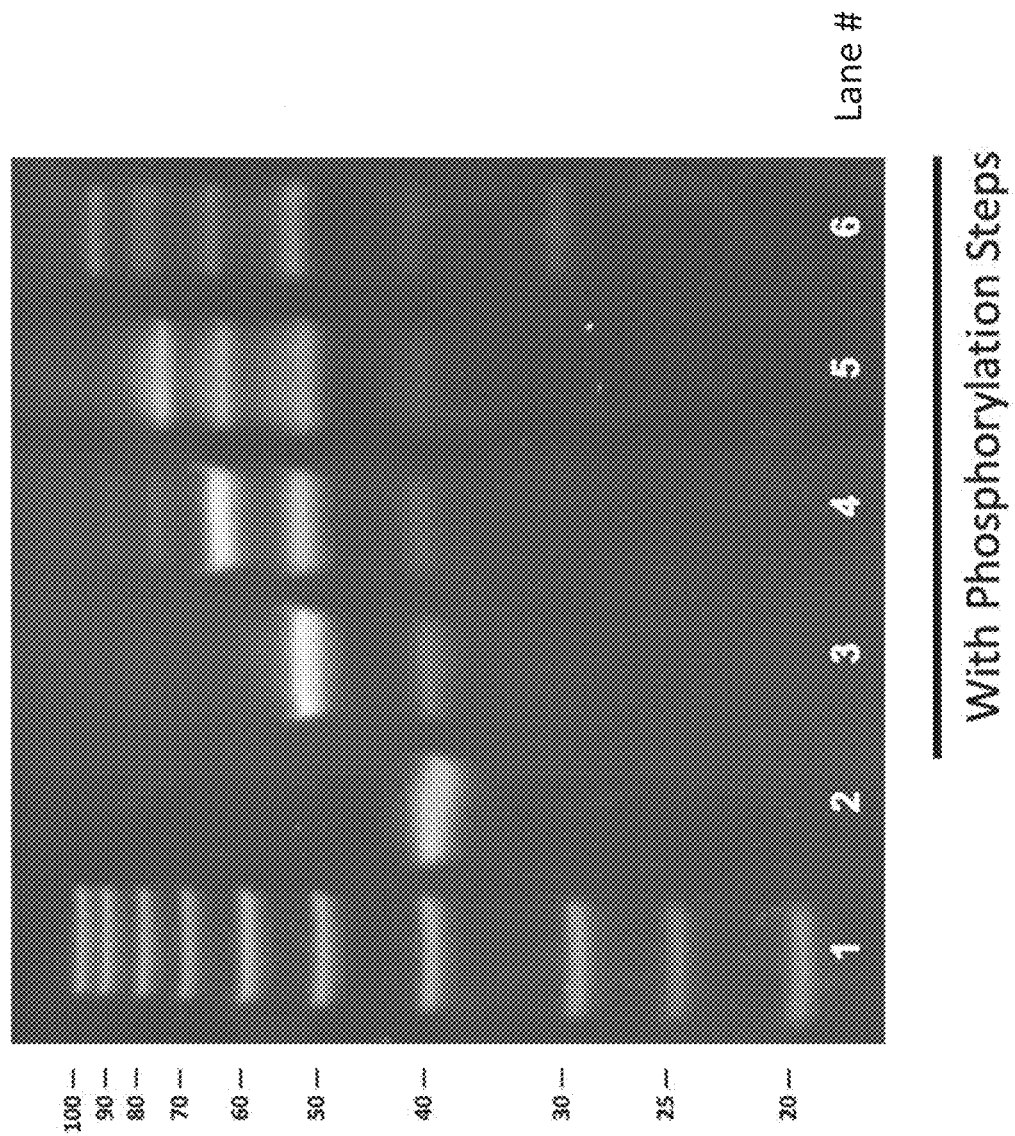

FIG. 22 is an image of a polyacrylamide gel used to analyze the products of the 5' modular linear synthesis method with 5' phosphorylation.

Figure 23:
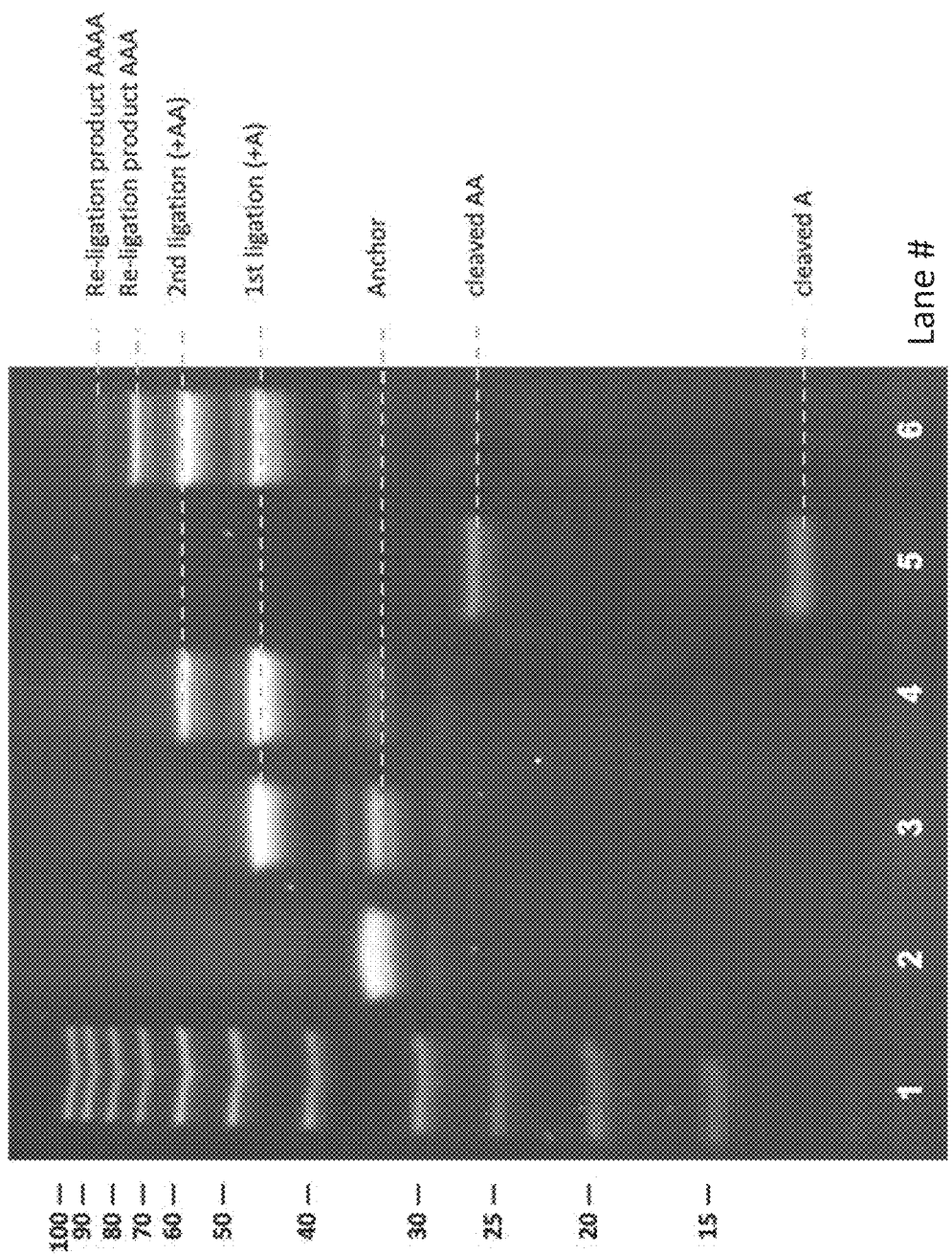

FIG. 23 is an image of a polyacrylamide gel used to analyze the products of the 3' extension geometric synthesis method of the present disclosure.

Figure 24:
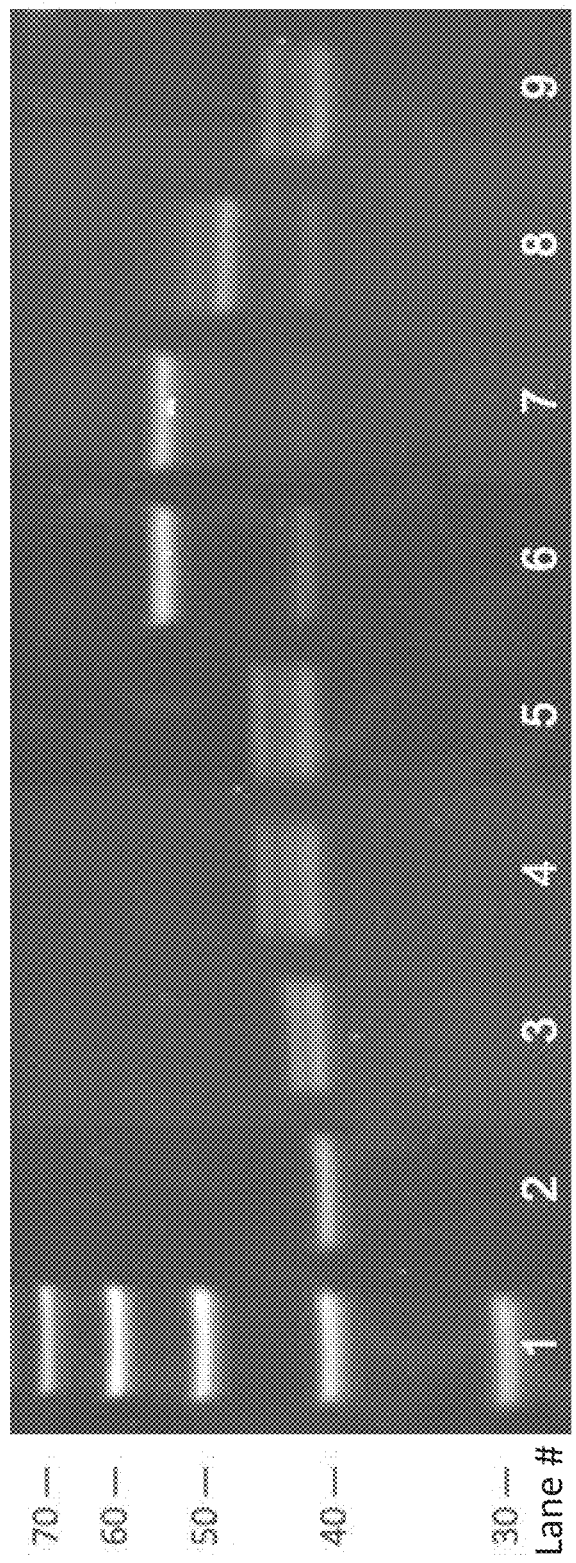

FIG. 24 is an image of a polyacrylamide gel used to analyze the products of various ligation reactions comprising 3-mers, 6-mers and 12-mers of the present disclosure.

Figure 25:
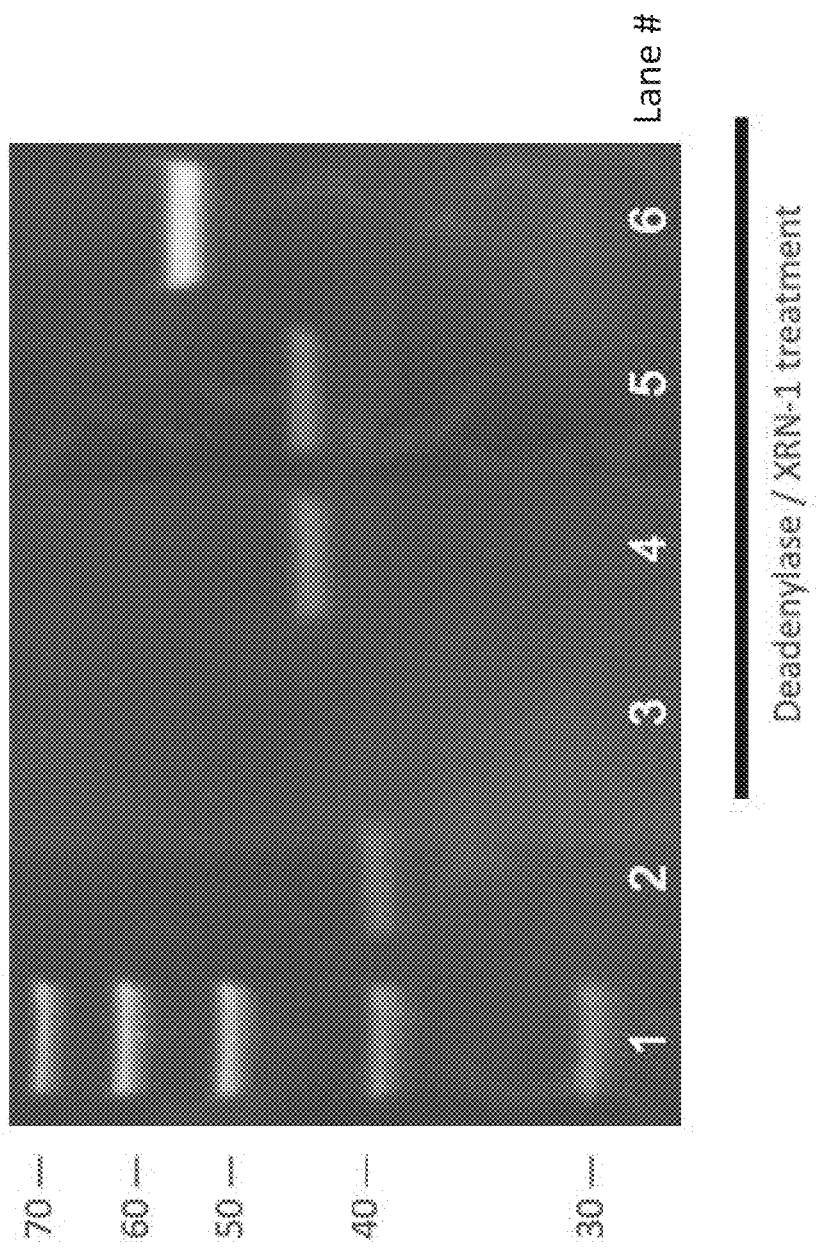

FIG. 25 is an image of a polyacrylamide gel used to analyze the products of XRN-1 digestion reactions following various ligation reactions comprising N-mers of the present disclosure.

Figure 26:
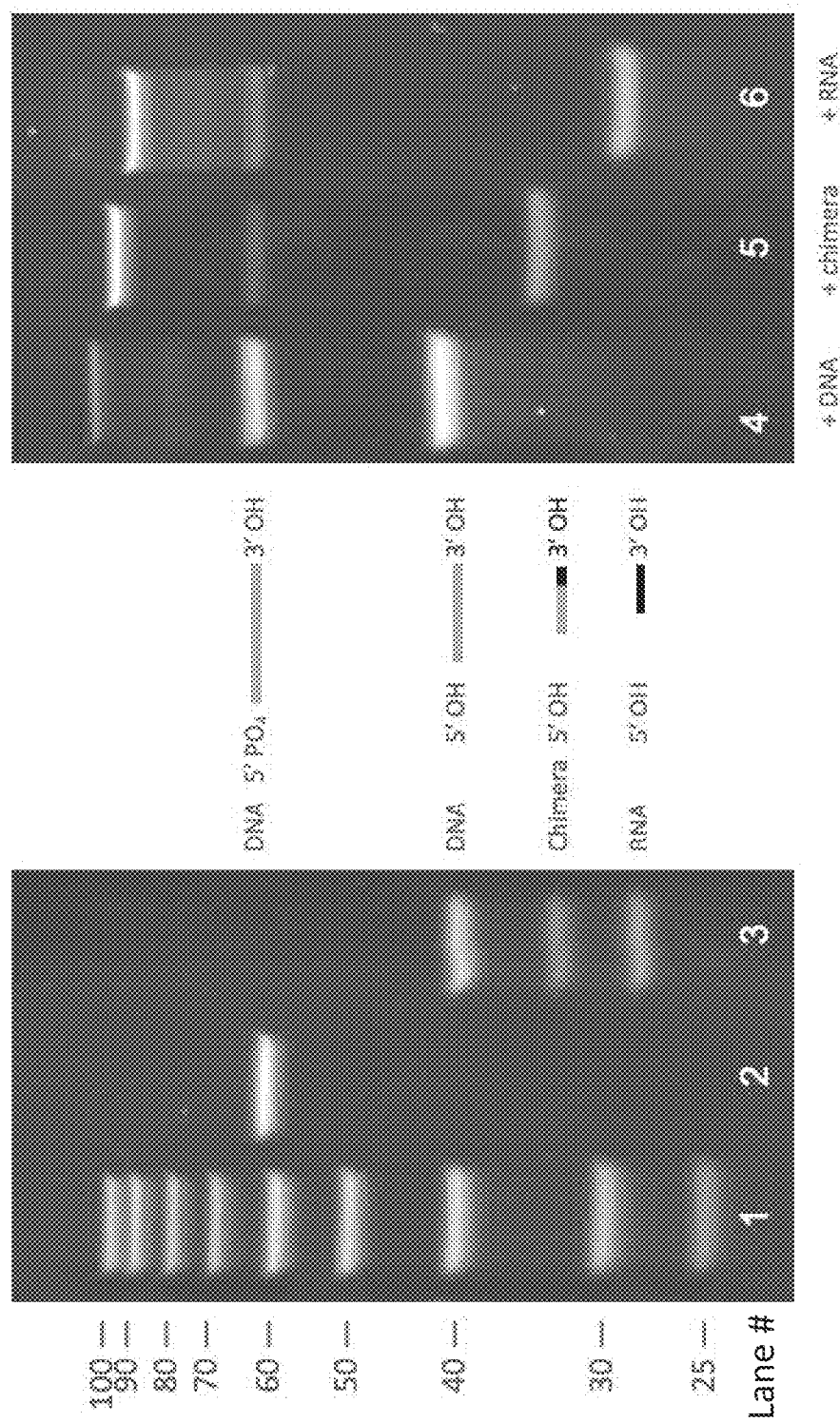

FIG. 26 is an image of a polyacrylamide gel used to analyze the products of various ligation reactions of N-mers comprising DNA, RNA and combinations thereof.

Figure 27:
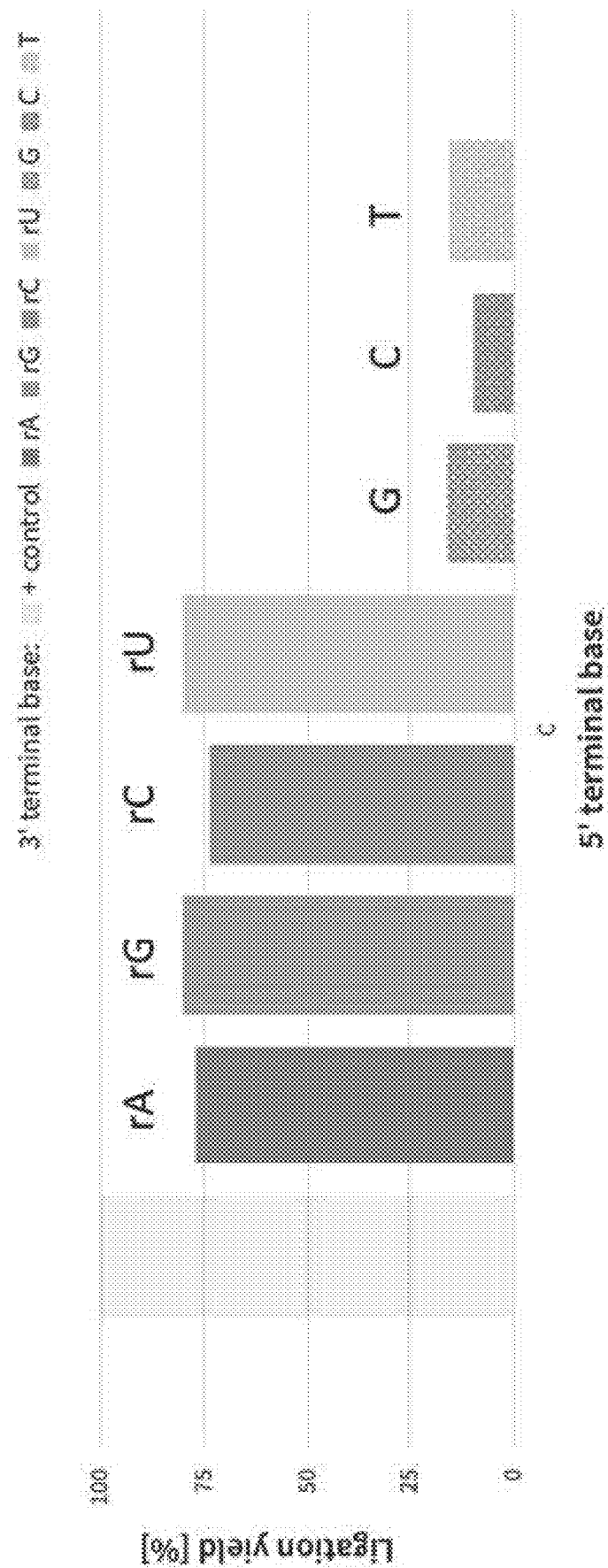

FIG. 27 is a chart showing the ligation efficiency of various N-mers comprising DNA, RNA or a combinations thereof.

Figure 28:
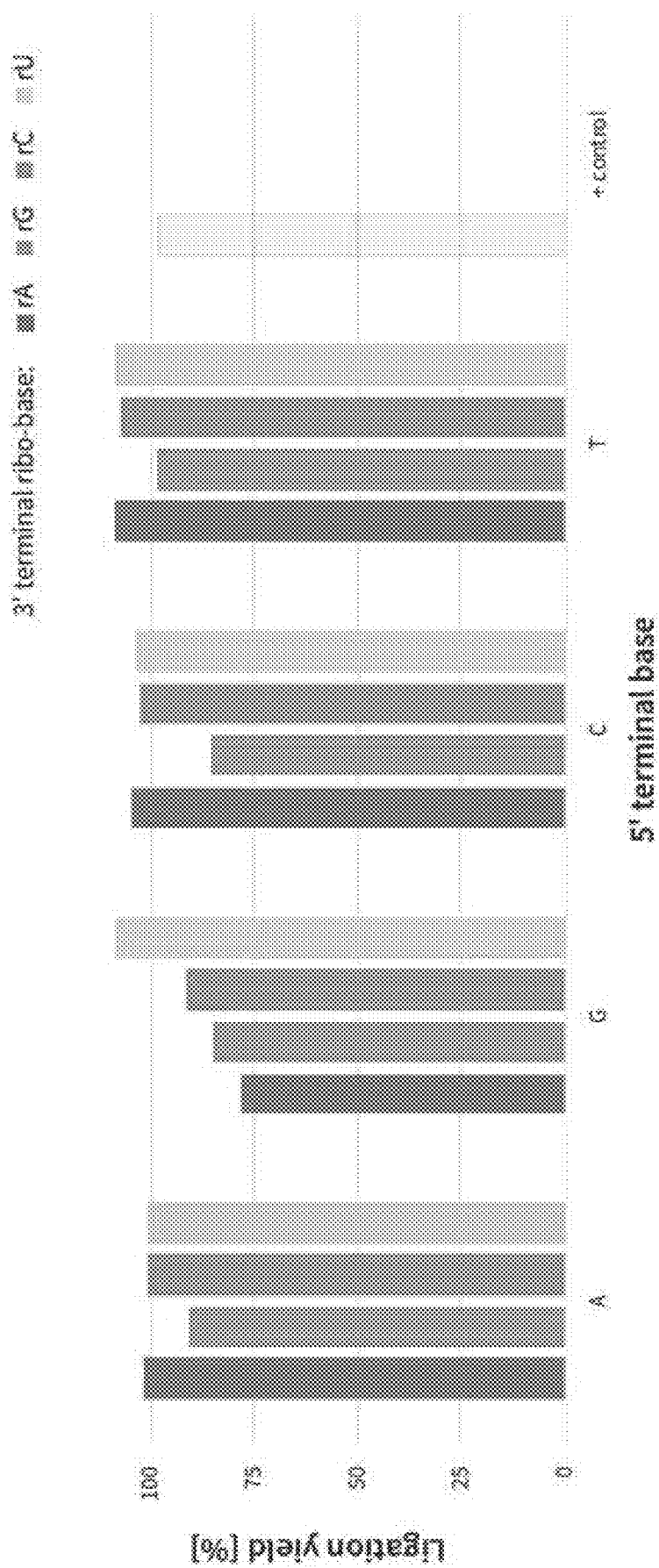

FIG. 28 is a chart showing the ligation efficiency of various ligation reactions in which the 5' ligated nucleotide is a deoxynucleotide and the 3' ligated nucleotide is a ribonucleotide.

Figure 29:
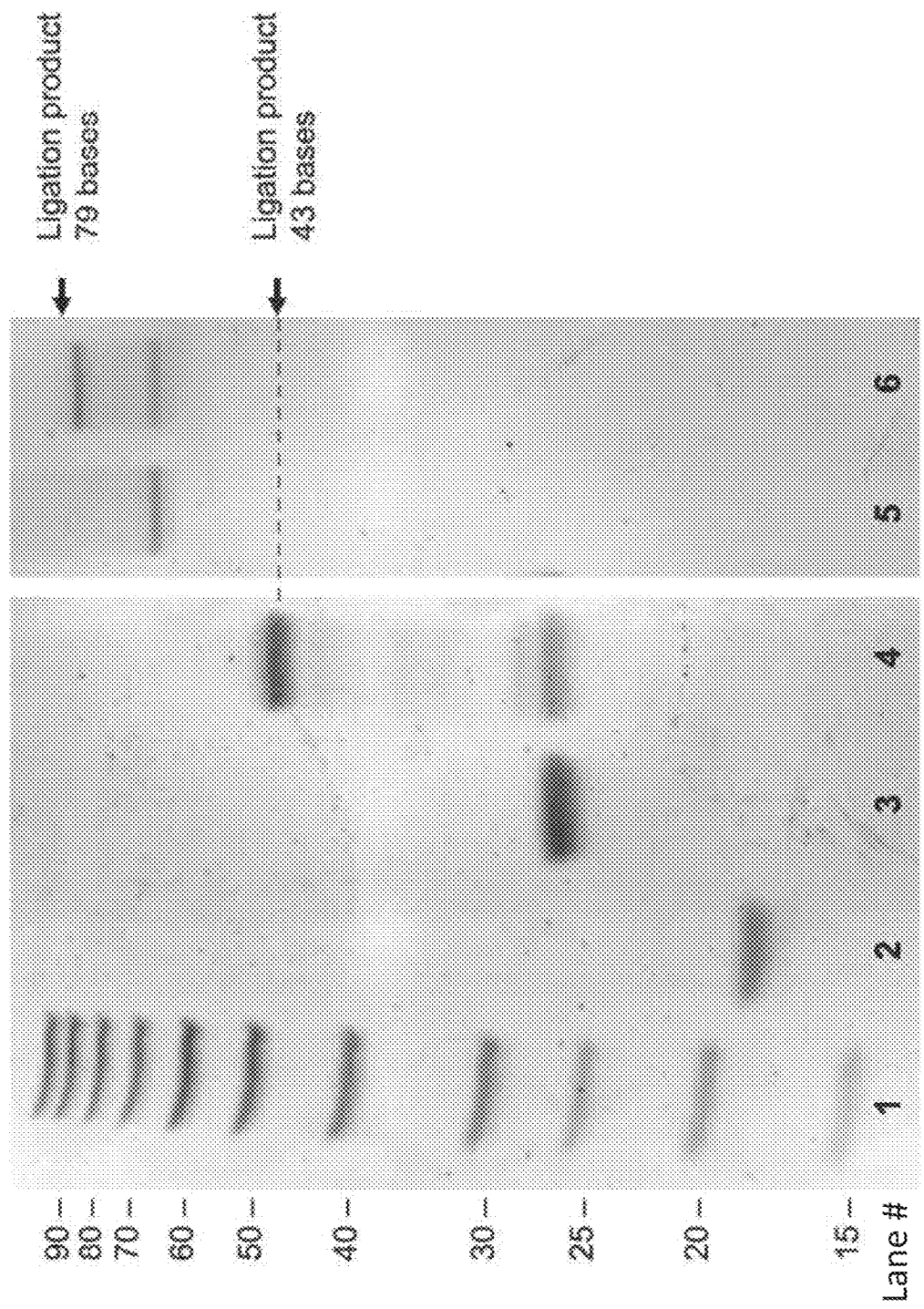

FIG. 29 is an image of a polyacrylamide gel used to analyze the products of ligation reactions comprising anchor primers attached to beads using either Click chemistry or biotin.

DETAILED DESCRIPTION

The present disclosure provides compositions, kits and methods for template-free geometric enzymatic nucleic acid synthesis of an arbitrarily programmed sequence.

The present disclosure provides compositions and methods for the enzymatic, template-independent, synthesis of nucleic acid (NA) polymers using short, error free NA fragments, systematically assembled to form arbitrarily long NA chains. Unique NA sequences can be synthesized by the systematic joining of shorter NA sequences using comprehensive libraries of purified short oligonucleotides and constant primer sequences. Libraries of short, error free NA fragment sequence can vary in size, but comprehensive coverage of all possible sequences is most achievable with 3-mers, having 64 possible sequences, 4-mers, with 256 possible sequences and 5-mers with 1024 possible sequences. Any longer sequence can be assembled by a sequential combination of 3-mers, 4-mers or 5-mers, collectively referred to as N-mers. The present disclosure also provides compositions of plasmid libraries containing all possible 3-mer, 4-mer and 5-mers in the form of enzymatically excisable elements. The present disclosure provides compositions of modified N-mers, assembled sequences, plasmid constructs, reaction conditions, reaction substrates and proprietary short oligo sequences. Additionally, the present disclosure provides several different methods for fast, accurate generation of long arbitrary NA chains as well as surface to surface amplification of NA molecules.

The present disclosure provides compositions comprising N-mers for both 3' and 5' extension in non-templated NA synthesis. These N-mers include all possible 3-mers (64), 4-mers (256) and 5-mers (1024) comprising either RNA or DNA. For 5' non-templated extension, the N-mer oligonucleotides do not require a phosphate group at either the 3' or 5' end. For 3' non-templated extension N-mers may possess a phosphate group at both 3' and 5' ends of each oligonucleotide. Additionally, N-mers may include reversible extension blocking groups, such as photo-labile blocking groups or the 4,4'-dimethoxytrityl phosphate (DMT-PO$_4$) group, at either the 5' end the 3' end or both ends of the N-mer oligonucleotide. Additionally, 5' ends may be activated by 5' adenylation for subsequent ligation with appropriately selective enzymes. 5' adenylation can be performed, for example, by treatment of the N-mer with Mth RNA ligase.

The present disclosure provides compositions comprising N-mers of any possible 3-mer (64), 4-mer (256) and 5-mer (1024) comprising RNA, DNA or a combination thereof. These N-mers may be chimeric NA molecules with a deoxyribose 5' (DNA) terminus and a ribose 3' (RNA) terminus. These N-mers may be wholly or partially comprised of DNA, RNA backbones.

The present disclosure provides compositions comprising assembled modules of N-mers into NA oligonucleotides of arbitrary length and sequence. These oligonucleotides may wholly or partially comprise DNA or RNA.

The present disclosure provides compositions comprising N-mers for 3' extension in non-templated NA synthesis. These N-mers include all possible 3-mers (64), 4-mers (256) and 5-mers (1024) comprising either RNA or DNA. These N-mers possess 5' triphosphate groups which may be a substrate for terminal transferase activity.

The present disclosure provides compositions comprising anchor primer sequences, which are proprietary short oligonucleotide sequences generally attached to a solid support with either the 3' or 5' end distal to the solid support. These oligonucleotide sequences are designed to allow the specific removal of any additional sequence that has been extended from the end of the anchoring primer sequence. Specific removal from the distal end of the anchoring primer sequence may be accomplished in several ways.

The present disclosure provides compositions comprising attachments of anchor primers to solid supports. Attachments may be non-covalently mediated, such as by biotin and avidin interactions or may be covalent links, such as a range of 'click' chemistries. Attachments may include spacer molecules such as polyethylene glycol (PEG) or triethylene glycol (TEG).

In certain aspects of the compositions of the present disclosure, for precise release of synthetic NA, include anchoring primer NAs with appropriately positioned abasic sites, which may be cut with DNA glycosylase-lyase Endonuclease VIII. Additionally, appropriately positioned deoxyuridine (U) sites may be first made abasic through the activity of Uracil DNA glycosylase, then the resulting abasic site may be cut using DNA glycosylase-lyase Endonuclease VIII.

In certain aspects of the compositions of the present disclosure, for precise release of synthetic NA, include anchoring primer NAs with appropriately positioned deoxyinosine (I) sites, which may be cut with Endonuclease V.

In certain aspects of the compositions of the present disclosure, for precise release of synthetic NA, include anchoring primer NAs with appropriately positioned sites for cleavage by a variety of restriction endonucleases (RE). These restriction nuclease sites may be for offset cutting REs, called Type II S restriction endonucleases, such as the enzyme MlyI.

In certain aspects of the compositions of the present disclosure, for precise release of synthetic NA, include anchoring primer NAs with appropriately positioned sites for single stranded specific cutting by Cas9 and appropriate guide RNAs.

The present disclosure provides compositions comprising solid supports. There are several solid supports are effective in the context of geometric synthesis. Specifically, solid supports include microscopic beads, magnetic or non-magnetic, made of polyacrylamide, polystyrene, crosslinked agarose or other similar materials. Solid supports may also include plastic or glass surfaces, such as the surfaces of wells of multi-well plates. Solid supports may be treated to enhance the NA binding properties or permit specific enzymatic activities. Likewise, surfaces may be treated to prevent non-specific or un-wanted binding.

The present disclosure provides compositions comprising DNA or RNA ligases, either ribozyme or protein, such as T4 RNA ligase, including mutant or modified DNA or RNA ligases, which require 5' adenylated N-mer substrates. Ligase are mixed with solid surface bound anchor primers and/or extended NA and N-mers in appropriate reactions solutions to affect the extension of the NA chain by one and only one N-mer unit.

In certain aspects of the compositions of the present disclosure, extension of the synthetic NA chain is mediated by terminal transferase enzymes such as terminal deoxynucleotidyl transferase (TdT), members of the X family of DNA polymerases or DNA polymerase Pol theta.

The present disclosure provides compositions comprising NA sequences derived de novo from a geometric synthesis process. In certain aspects of the present disclosure sequences of NA are generated by combinations of N-mers. These NA sequences can be generated by the geometric 3' method, by the geometric 5' method, by the geometric transposase method or by the geometric 3', 5' co-synthesis method.

The present disclosure provides compositions comprising NA sequences derived de novo from 3' extension parallel synthesis using N-mers. A multiplicity of NA sequences generated in parallel are made by one at a time extension from solid support bound anchor primers.

The present disclosure provides compositions of plasmid sequences that possess N-mer sequences for enzymatic addition of N-mers using transposase elements. Activity of transposases lead to the excision of transposable element specific sequences from the elongating synthetic NA chain, leaving only N-mer additions. The basic plasmid design includes 1) reverse oriented, transposable element derived right and left inverted terminal repeat (ITR) elements positioned on either side of an N-mer sequence, 2) a selectable marker, such as ampicillin resistance, 3) an origin of replication and 4) a multiple cloning site containing a n appropriate set of restriction endonuclease sites. The present disclosure provides compositions for a plurality of plasmid sequence each possessing a unique N-mer sequence as well as transposable element specific sequences and elements for the propagation of the plasmid in bacterial cells.

The present disclosure provides compositions comprising a system for the amplification of intermediate or final products of geometric NA synthesis. Solid supports, for example beads, micro-well plate surfaces or glass slide surfaces are coated with oligonucleotide primers, which are also anchor primers for ongoing synthesis reactions. A template bearing surface and an anchor primer bearing surface are brought together in a common reaction buffer along with free oligonucleotide primers, which are the reverse complementary sequence of the distal end of the template NA. Amplification is carried out by polymerase chain reaction, recombinase-polymerase reaction or a similar NA replication, amplification system.

The present disclosure provides a method of 5' extension geometric synthesis. Initially an appropriate number of samples is set up, for example in multi-well plates. Each sample first contains anchor primers, which bear —$PO_4$ at 5' ends and have been affixed to solid supports. 1) The process begins with ligation of an N-mer species onto anchor primers. The N-mers bear a —OH at each the 3' and 5' ends. 2) After the first ligation, a 5' to 3' specific exonuclease, such as Lambda exonuclease is used to remove un-ligated anchor primers from the solid supports. Lambda cannot digest NAs bearing a 5' —OH. 3) After exonuclease digestion samples are treated with Polynucleotide Kinase (PNK), to produce a —$PO_4$ at each 5' end. 4) A second round of ligation with another N-mer species is carried out as in the first ligation, this is followed by a similar 5' to 3' exonuclease digestion. 5) After first two rounds of ligation and exonuclease treatment samples become either 'targets' or 'donors'. 5a) Target samples receive PNK treatment. 5b) Donor samples are released from solid support, preserving —OH groups both 3' and 5' groups, using described methods such as a restriction enzyme to cut a partially double stranded anchor primer. On subsequent rounds 'donor' samples are ligated to 'target' samples according to 1), 2) and 5).

The present disclosure provides a method of 3' extension geometric synthesis. Initially an appropriate number of samples is set up, for example in multi-well plates. Each sample first contains anchor primers, which bear —OH at 3' ends and have been affixed to solid supports. 1) The process begins with ligation of an N-mer species onto anchor primers. The N-mers bear a —$PO_4$ at each the 3' and 5' ends. 2) After the first ligation, a 3' to 5' specific exonuclease, such as Klenow is used to remove un-ligated anchor primers from the solid supports. Klenow cannot digest NAs bearing a 3' —$PO_4$. 3) After exonuclease digestion samples are treated with phosphatase, such as Calf Intestinal Alkaline Phosphatase (CIP) or Shrimp Alkaline Phosphatase (SAP), to remove 3' —$PO_4$. 4) A second round of ligation with another N-mer species is carried out as in the first ligation, this is followed by a similar 3' to 5' exonuclease digestion. 5) After first two rounds of ligation and exonuclease treatment samples become either 'targets' or 'donors'. 5a) Target samples receive phosphatase treatment. 5b) Donor samples are released from solid support, preserving both 3' and 5' —$PO_4$ groups using described methods such as a restriction enzyme cutting a partially double stranded anchor primer. On subsequent rounds 'donor' samples are ligated to 'target' samples according to 1), 2) and 5).

The present disclosure provides a method of 3' extension parallel synthesis using N-mers. The N-mers described in the present disclosure may also possess reversible blocks on the 3' hydroxyl group, which make the site unavailable for enzymatic incorporation of additional nucleotides, N-mers or longer oligonucleotides. The reversible block may be removed by a variety of methods, including exposure to light or chemical reagents. In parallel synthesis, many different reactions can be specifically controlled allowing arbitrary incorporation of specific N-mers. In a two-dimensional grid, regions are specifically addressed by light focused on grid elements. Exposed areas become activated and are then able to incorporate the available short oligonucleotide sequence. The two-dimensional grid may begin with general attachment of 3' reversibly blocked anchor primer sequences. If the incorporation of a specific N-mer, such as ACG, is required, then the region of the two-dimensional grid where ACG is required is exposed to light, which will reverse the block and allow the ACG N-mer to be incorporated only there. Such a process ensues for all 64 possible 3-mers suitably blocked at the 3' end. Any possible sequence combination can be manifest at any specific location on the grid. The grid may be a chamber with activated regions on a flat glass or similar surface. Additionally, the grid may be a chamber capable of holding an array of beads with attached anchor primers. In either case the reagents of the reactions are delivered by a microfluidic system.

The present disclosure provides a method of double stranded geometric synthesis mediated by transposases. This method relies on a collection of plasmids with reverse oriented left and right terminal repeats derived from a precisely excising transposable element, such as piggyBac. Each plasmid in the collection carries a different N-mer sequence (3-, 4-, and 5-mers). Prior to synthesis reactions each required N-mer sequence is excised from its plasmid backbone by appropriate restriction endonuclease (RE) or similar digestion. As with the 5' and 3' extension geometric synthesis methods, multiple parallel reactions are carried out. Each reaction possesses a solid support carrying a double-stranded anchor primer sequence with a distal RE site compatible with the RE used to excise the N-mer sequence from the plasmids. 1) The process begins with ligation of an N-mer carrying inverse transposable element onto anchor primers followed by reaction cleanup. By placing the normal left-side inverted terminal repeat sequence (ITR) on the right side and the right-side ITR on the left side of the N-mer sequence, the resulting inverse transposable element is not a target transposase activity. 2) A second N-mer carrying inverse transposable element is then ligated to the extending NA chain on the solid support followed by cleanup. 3) Treatment of the extending NA chain with transposase leads to the excision of the intervening sequence between the two N-mer sequences. 3) The ligated, excised NA chain can be released from the beads by a RE reaction and can then serve as a 'donor' for a subsequent ligation reaction. 4) Cycles of cleavage and transfer, ligation and cleanup, followed by excision using appropriate 'donors' and 'targets' will lead eventually to the desired NA sequence.

The present disclosure provides a method of 5' extension and 3' extension geometric co-synthesis. This allows accelerated long, fast NA synthesis using a mixed 3', 5' co-synthesis with DNA polymerase filling and ligation. Initially a set of partially overlapping NA fragments is generated using another method. An annealing reaction is carried out with the partially overlapping complementary fragments. A polymerase reaction extends each of the overlapping 3' end is extended. The final product is generated by a ligase reaction that resolved the breaks between fragments.

The present disclosure provides a method of surface to surface transfer amplification. Amplification begins with template molecules, which are brought into the reaction on a solid support. The template NA molecules bear unique sequences at the proximal and distal ends. In the case of a geometric synthesis reaction, the distal unique sequence may be ligated onto the template sequence. These sequences are used as targets for primers: primers attached to the beads, which in the case of geometric synthesis would essentially be the anchor primers, and opposing primers that are free in solution. In the amplification reaction, which can be mediated by either PCR or RPA, a polymerase synthesizing from a template bound free primer will make a reverse complement copy of the template NA. The replicated strand is released, for example, during the melt phase of a PCR cycle, and can then hybridize to acceptor-surface bound primers. The copy strands then serve as templates for new generation of original NA molecules mediated by polymerase synthesizing from surface-bound primers (black). In surface to surface transfer amplification many surfaces will work. The donor surface could be a small bead and the acceptor a larger bead. If the smaller bead were 20 μm in diameter and the larger bead 150 μm in diameter the degree of amplification would be more than 50-fold. Alternatively, the template may be initially on the surface of a well of a multi-well plate and the acceptor surface could be a bead introduced into the well. Likewise, the donor surface may be a small bead introduced to a large surface well or onto a flat surface of a microscope slide. NAs are both amplified and transferred in the reaction.

Any of the above aspects can be combined with any other aspect.

Unless otherwise defined, all technical and scientific terms used herein have the same meaning as commonly understood by one of ordinary skill in the art to which the present disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

N-mers

In some aspects, the present disclosure provides a composition comprising an N-mer, as described in detail herein. An N-mer can comprise a polynucleotide. An N-mer can comprise at least about 1 nucleotide, or at least about 2 nucleotides, or at least about 3 nucleotides, or at least about 4 nucleotides, or at least about 5 nucleotides, or at least about 6 nucleotides, or at least about 7 nucleotides, or at least about 8 nucleotides, or at least about 9 nucleotides, or at least about 10 nucleotides, or at least about 11 nucleotides, or at least about 12 nucleotides, or at least about 13 nucleotides, or at least about 14 nucleotides, or at least about 15 nucleotides, or at least about 16 nucleotides, or at least about 17 nucleotides, or at least about 18 nucleotides, or at least about 19 nucleotides, or at least about 20 nucleotides, or at least about 21 nucleotides, or at least about 22 nucleotides, or at least about 23 nucleotides, or at least about 24 nucleotides, or at least about 25 nucleotides, or at least about 26 nucleotides, or at least about 27 nucleotides, or at least about 28 nucleotides, or at least about 29 nucleotides, or at least about 30 nucleotides, or at least about 31 nucleotides, or at least about 32 nucleotides, or at least about 33 nucleotides, or at least about 34 nucleotides, or at least about 35 nucleotides, or at least about 40 nucleotides, or at least about 45 nucleotides, or at least about 50 nucleotides, or at least about 60 nucleotides. An N-mer that comprises 1 nucleotides is herein referred to as a 1-mer, an N-mer that comprises 2 nucleotides is herein referred to as a 2-mer, and so on and so forth.

In some aspects, an N-mer can comprise a 3' —$PO_4$ group. In some aspects, an N-mer can comprise a 5' —$PO_4$ group. In some aspects, an N-mer can comprise a 3' —$PO_4$ group and a 5' —$PO_4$ group.

In some aspects, an N-mer can comprise a 3' —OH group. In some aspects, and N-mer can comprise a 5' —OH group. In some aspects, and N-mer can comprise a 3' —OH group and a 5' —OH group.

In some aspects, an N-mer can comprise a 3' triphosphate group. In some aspects, an N-mer can comprise a 5' triphosphate group. In some aspects, an N-mer can comprise a 3' triphosphate group and a 5' triphosphate group.

In some aspects, an N-mer can comprise RNA. In some aspects, an N-mer can comprise DNA. In some aspects, an N-mer can comprise DNA and RNA, referred to herein as a chimeric N-mer. An N-mer can be wholly or partially comprised of DNA or RNA. An N-mer can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% RNA. An N-mer can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% DNA.

In some aspects, an N-mer can be a chimeric N-mer comprising a deoxyribose 5' (DNA) terminus and a ribose 3' (RNA) terminus. In some aspects, an N-mer can be a chimeric N-mer comprising a deoxyribose 3' (DNA) terminus and a ribose 5' (RNA) terminus. In some aspects, an N-mer can be a chimeric N-mer comprising a deoxyribose 5' (DNA) terminus and a deoxyribose 3' (DNA) terminus. In some aspects, an N-mer can be a chimeric N-mer comprising a ribose 5' (RNA) terminus and a ribose 3' (RNA) terminus.

In some aspects, an N-mer can comprise a reversible extension blocking group. A reversible extension blocking group is a chemical group that prevents ligation and/or extension at the terminus of the nucleic acid molecule to which it is attached and that can be removed, for example by exposure to light of a specific wavelength or to a particular chemical. In some aspects, a reversible extension blocking group can be a photo-liable blocking group or a 4,4'-dimethoxytrityl phosphate (DMT-$PO_4$). An N-mer can have a reversible blocking group at the 5' terminus. An N-mer can have a reversible blocking group at the 3' terminus. An N-mer can have a reversible blocking group at both the 5' and the 3' terminus. As used herein, the terms "blocking group" and "protecting group" are used interchangeably. As used herein, the terms "removing the blocking group" and "deprotecting" are used interchangeably.

In some aspects, the 5' end of an N-mer can be activated by 5' adenylation for subsequent ligation with appropriately selective enzymes.

N-mers as described herein can be used in any method of the present disclosure, as described herein.

Libraries of N-mers

In some aspects, the present disclosure provides a composition comprising a library of N-mers. A library of N-mers comprises a plurality of N-mer species such that there is at least one N-mer comprising every possible nucleic acid sequence for the given length of N-mers in the library. For example, in a library of N-mers, wherein the N-mers comprise 3 nucleotides (3-mer), there are 64 possible sequences of 3 nucleotides. Thus a 3-mer library of the present disclosure comprises at least 64 species of 3-mers. In another example, in a library of N-mers, wherein the N-mers comprise 4 nucleotides (4-mer), there are 256 possible sequences of 4 nucleotides. Thus, a 4-mer library of the present disclosure comprises at least 256 species of N-mers. In another example, in a library of N-mers, wherein the N-mers comprise 5 nucleotides (5-mer), there are 1024 possible sequences of 5 nucleotides. Thus, a 5-mer library of the present disclosure comprises at least 1024 species of N-mers. This can be extrapolated to libraries of N-mers with any number of nucleotides in each N-mer: a library of N-mers that comprise x nucleotides (x-mer) comprise at least $4^x$ different species of x-mers.

In some aspects, the present disclosure provides libraries of N-mers comprising all possible 3-mers (64), or 4-mers (256), or 5-mers (1024), or 6-mers (4096), or 7-mers (16,384), or 8-mers (65,536), or 9-mers (262,144), or 10-mers (1,048,576), and so on and so forth, wherein the N-mers in the library comprise DNA, RNA or a combination of RNA and DNA.

In some aspects, in libraries of the present disclosure, each species of N-mer can be present in the same amount. In some aspects, in libraries of the present disclosure, each species of N-mer can be present in different amounts. In some aspects, in libraries of the present disclosure, some species of N-mer are present in the same amount and other species of N-mer are present in different amounts.

Each N-mer in a library of N-mers can comprise any attribute or feature as described herein.

Libraries of N-mers as described herein can be used in any method of the present disclosure, as described herein.

Anchor Primers

In some aspects, the present disclosure provides compositions comprising anchor primer sequences. The terms "anchor primer sequences" and "anchor primers" are used interchangeably herein.

Anchor primer sequences can comprise a polynucleotide. Anchor primer sequences can comprise at least about 1 nucleotide, or at least about 2 nucleotides, or at least about 3 nucleotides, or at least about 4 nucleotides, or at least about 5 nucleotides, or at least about 6 nucleotides, or at least about 7 nucleotides, or at least about 8 nucleotides, or at least about 9 nucleotides, or at least about 10 nucleotides, or at least about 11 nucleotides, or at least about 12 nucleotides, or at least about 13 nucleotides, or at least about 14 nucleotides, or at least about 15 nucleotides, or at least about 16 nucleotides, or at least about 17 nucleotides, or at least about 18 nucleotides, or at least about 19 nucleotides, or at least about 20 nucleotides, or at least about 21 nucleotides, or at least about 22 nucleotides, or at least about 23 nucleotides, or at least about 24 nucleotides, or at least about 25 nucleotides, or at least about 26 nucleotides, or at least about 27 nucleotides, or at least about 28 nucleotides, or at least about 29 nucleotides, or at least about 30 nucleotides, or at least about 31 nucleotides, or at least about 32 nucleotides, or at least about 33 nucleotides, or at least about 34 nucleotides, or at least about 35 nucleotides, or at least about 40 nucleotides, or at least about 45 nucleotides, or at least about 50 nucleotides, or at least about 60 nucleotides, or about 70 nucleotides, or about 80 nucleotides, or about 90 nucleotides, or about 100 nucleotides.

In some aspects, an anchor primer sequence can comprise RNA. In some aspects, an anchor primer sequence can comprise DNA. In some aspects, an anchor primer sequence can comprise DNA and RNA. An anchor primer sequence can be wholly or partially comprised of DNA or RNA. An anchor primer sequence can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% RNA. An anchor primer sequence can be about 1%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95% DNA.

In some aspects, an anchor primer sequence can be double-stranded. An anchor primer sequence can be single-stranded. An anchor primer sequence can be partially double-stranded. An anchor primer sequence can be partially single-stranded.

In some aspects, an anchor primer sequence can comprise a restriction endonuclease site. The terms "restriction endonuclease site" and "restriction site" are used interchangeably herein. In some aspects, an anchor primer sequence can comprise at least about 1 restriction site, or at least about 2 restriction sites, or at least about 3 restriction sites, or at least about 4 restriction sites, or at least about 5 restriction sites, or at least about 6 restriction sites, or at least about 7 restriction sites, or at least about 8 restriction sites, or at least about 9 restriction sites, or at least about 10 restriction sites.

In some aspects, an anchor primer sequence can comprise an EcoRI restriction site. In some aspects, an anchor primer sequence can comprise a MlyI restriction site. In some aspects, an anchor primer sequence can comprise an EcoRV restriction site. In some aspects, an anchor primer sequence can comprise a SbfI restriction site. Endonuclease restriction sites include, but are not limited to, AclI, HindIII, SspI, MluCI, PciI, AgeI, BspMI, BfuAI, SexAI, MluI, BceAI, HpyCH4IV, HpyCH4III, BaeI, BsaXI, AflIII, SpeI, Bsd, BmrI, BglII, AfeI, AluI, StuI, BspDI, ClaI, PI-SceI, NsiI, AseI, SwaI, CspCI, MfeI, Nb.BssSI, BssSaI, BmgBI, PmlI, AleI, EcoP15I, PvuII, AlwNI, BtsIMutI, NdeI, CviAII, FatI, NlaIII, MslI, FspEI, XcmI, BstXI, PflMI, BccI, NcoI, BseYI, FauI, TspMI, XmaI, SmaI, Nt.CviPII, LpnPI, AciI, SacII, BsrBI, HpaII, MspI, ScrFI, StyD4I, BsaJI, Bs1I, BtgI, NciI, AvrII, Mn1I, Nt.BbvCI, Nb.BbvCI, BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Esp3I, Hpy99I, MspA1I, AbaSI, MspJI, SgrAI, BfaI, BspCNI, XhoI, PaeR7I, EarI, AcuI, PstI, BpmI, DdeI, SfcI, AflII, BpuEI, Sm1I, AvaI, BsoBI, MboII, BbsI, XmnI, BsmI, Nb.BsmI, EcoRI, HgaI, ZraI, AatII, Tth111I, PflFI, PshAI, AhdI, DrdI, Eco53kI, SacI, BseRI, MlyI, PleI, Nt.BstNBI, HinfI, EcoRV, Sau3AI, MboI, DpnII, DpnI, BsaBI, TfiI, BsrDI, Nb.BsrDI, BbvI, Nb.BtsI, BtsaI, BstAPI, SfaNI, SphI, SrfI, NmeAIII, NaeI, NgoMIV, BglI, AsiSI, BtgZI, HhaI, HinPlI, BssHII, NotI, Fnu4HI, Cac8I, MwoI, BmtI, NheI, Nt.BspQI, BspQI, SapI, BlpI, TseI, ApeKI, Bsp1286I, AlwI, Nt.AlwI, BamHI, BtsCI, FokI, HaeIII, FseI, SfiI, NarI, PluTI, SfoI, KasI, AscI, EciI, BsmFI, ApaI, PspOMI, Sau96I, NlaIV, KpnI, Acc65I, BsaI, HphI, BstEII, AvaII, BanI, BaeGI, BsaHI, BanII, CviQI, RsaI, BciVI, SalI, Nt.BsmAI, BcoDI, BsmAI, ApaLI, BsgI, AccI, Hpy166II, Tsp45I, HpaI, PmeI, HincII, BsiHKAI, TspRI, ApoI, ApoI-HF, NspI, BsrFaI, BstYI, HaeII, CviKI-1, EcoO109I, PpuMI, I-CeuI, SnaBI, I-SceI, BspHI, BspEI, MmeI, TaqaI, NruI, Hpy188I, Hpy188III, XbaI, BclI, BclI-HF, HpyCH4V, FspI, PI-PspI, MscI, BsrGI, MseI, PacI, PsiI, BstBI, DraI, PspXI, BsaWI, BsaAI or EaeI sites. A restriction site can be a restriction site for offset cutting restriction enzymes, also called Type II S restriction endonuclease. A non-limiting example of a Type II S restriction endonuclease is the enzyme Mly1.

An anchor primer sequence can be directly or indirectly attached to a solid support. Attachments may be non-covalently mediated, such as by biotin and avidin interactions or may be covalent links, such as a range of 'click' chemistries. Attachments may include spacer molecules such as polyethylene glycol (PEG) or triethylene glycol (TEG).

An anchor primer sequence can comprise at least about 1, or at least about 2, or at least about 3, or at least about 4, or at least about 5, or at least about 6, or at least about 7, or at least about 8, or at least about 9, or at least about 10 abasic nucleic acid molecules. The terms "abasic nucleic acid molecule" and "abasic site" are used interchangeably herein. An abasic nucleic acid molecule is a nucleic acid molecule that has neither a purine nor a pyrimidine base. A polynucleotide comprising a basic nucleic acid molecule can be cleaved with DNA glycosylate-lyase endonuclease VIII.

An anchor primer sequence can comprise at least about 1, or at least about 2, or at least about 3, or at least about 4, or at least about 5, or at least about 6, or at least about 7, or at least about 8, or at least about 9, or at least about 10 deoxyuridine nucleic acid molecules. The terms "deoxyuridine nucleic acid molecules" and "deoxyuridine sites" are used interchangeably herein. A deoyuridine site can be transformed into an abasic by treatment with Uracil DNA glycosylase, then the resulting abasic site may be cleaved using DNA glycosylate-lyase endonuclease VIII.

An anchor primer sequence can comprise at least about 1, or at least about 2, or at least about 3, or at least about 4, or at least about 5, or at least about 6, or at least about 7, or at least about 8, or at least about 9, or at least about 10 deoxyinosine nucleic acid molecules. The terms "deoxyinosine nucleic acid molecule" and "deoxyinosine site" are used interchangeably herein. A deoxyinosine site can be cleaved with endonuclease V.

An anchor primer sequence can comprise a targeting nucleic acid sequence that is complementary to a guide RNA. The targeting nucleic acid sequence can then be cleaved by Cas9 and the complementary guide RNA.

In some aspects, anchor primers are designed to allow the specific removal of any additional sequence and/or nucleic acid fragment that has been extended from the end of the anchoring primer sequence. Specific removal of the additional sequence and/or nucleic acid fragment may be accomplished in several ways. In a non-limiting example, a restriction site located between the additional sequence/nucleic acid fragment and the anchor primer sequence can be cleaved with the appropriate restriction endonuclease. In some aspects, the restriction site located between the additional sequence/nucleic acid fragment and the anchor primer sequence can be formed by hybridizing a short reverse complementary oligonucleotide to the anchor primer sequence. In another non-limiting example, an abasic site located between the additional sequence/nucleic acid fragment and the anchor primer sequence can be cleaved using DNA glycosylate-lyase endonuclease VIII. In another non-limiting example, a deoxyuridine site located between the additional sequence/nucleic acid fragment and the anchor primer sequence can be first converted into an abasic site using Uracil DNA glycosylase, and the abasic site then cleaved using DNA glycosylate-lyase endonuclease VIII. In another non-limiting example, a deoxyinsone site between the additional sequence/nucleic acid fragment and the anchor primer sequence can be cleaved using endonuclease V.

FIG. 2 shows four exemplary anchor primer sequences of the present disclosure attached to solid supports. In these non-limiting examples, the solid supports are beads.

FIG. 2A shows an anchor primer sequence for use in a 3' extension geometric synthesis method of the present disclosure. The anchor primer sequence comprises a low-complexity polynucleotide that is attached to the solid support bead at its 5' terminus. The 3' terminus is therefore exposed for ligation and extension of nucleic acid fragments. Hybridized to the anchor primer sequence is a short reverse complementary oligonucleotide. The short reverse complementary oligonucleotide is hybridized such that the resulting double-stranded structure comprises a MlyI restriction site, shown in red font.

FIG. 2B shows an anchor primer sequence for use in a 5' extension geometric synthesis method of the present disclosure. The anchor primer sequence comprises a low-complexity polynucleotide that is attached to the solid support bead at its 3' terminus. The 5' terminus is therefore exposed for ligation and extension of nucleic acid fragments. Hybridized to the anchor primer sequence is a short reverse complementary oligonucleotide. The short reverse complementary oligonucleotide is hybridized such that the resulting double-stranded structure comprises a MlyI restriction site (shown in red font), an EcoRI restriction site (shown in green font), an EcoRV (shown in blue font) and a SbfI site (shown in purple font).

FIG. 2C shows an anchor primer sequence for use in a 3' extension geometric synthesis method of the present disclosure. The anchor primer sequence comprises a low-complexity polynucleotide that is attached to the solid support bead at its 5' terminus. The 3' terminus is therefore exposed for ligation and extension of nucleic acid fragments. The anchor primer sequence comprises a deoxyuridine site (U) at the 3' terminus (shown in red) that can be transformed into an abasic site through the activity of Uracil DNA glycosylase. The resulting abasic site may then be cut using DNA glycosylate-lyase endonuclease VIII.

FIG. 2D shows an anchor primer sequence for use in a 5' extension geometric synthesis method of the present disclosure. The anchor primer sequence comprises a low-complexity polynucleotide that is attached to the solid support bead at its 3' terminus. The 5' terminus is therefore exposed for ligation and extension of nucleic acid fragments. The anchor primer sequence comprises a combination of deoxyadenosine (A) and deoxyinosine (I) at the 5' terminus (shown in red font) that can be cleaved by Endonuclease V.

Anchor primers as described herein can be used in any method of the present disclosure, as described herein.

Solid Supports

In some aspects, the present disclosure provides compositions comprising solid supports. Solid supports can include, but are not limited to, magnetic microscopic beads or non-magnetic microscopic beads. The beads can comprise polyacrylamide, polystyrene, crosslinked agarose, or other similar materials. Solid supports can include, but are not limited to, plastic or glass surfaces, such as the surfaces of wells of multi-well plates. In some aspects, solid supports may be treated to enhance the nucleic acid binding properties or permit specific enzymatic activities. In some aspects, solid supports may be treated to prevent non-specific or un-wanted binding.

In some aspects, a solid support of the present disclosure can comprise a plurality of chambers. The chambers can be arranged in a grid. For example, a solid support of the present disclosure can be a 6, 12, 24, 48, 96, 384 or 1536 well microplate. Chambers can be hold an array of beads with attached anchor primers.

In some aspects, a solid support of the present disclosure can be connected to a microfluidic system for the delivery of reagents.

Solid supports as described herein can be used in any method of the present disclosure, as described herein.

Overlapping Sets of Nucleic Acid Fragments

The present disclosure provides a composition comprising a set of overlapping nucleic acid fragments. A set of overlapping nucleic acid fragments can comprise a plurality of nucleic acid fragments. Each nucleic acid fragment in the plurality of nucleic acid fragments can comprise at least about 2, or at least about 5, or at least about 10, or at least about 20, or at least about 25, or at least about 30, or at least about 35, or at least about 40, or at least about 45, or at least about 50, or at least about 55, or at least about 60, or at least about 65, or at least about 70, or at least about 75, or at least about 80, or at least about 85, or at least about 90, or at least about 95, or at least about 100, or at least about 105, or at least about 110, or at least about 115, or at least about 120, or at least about 125, or at least about 130, or at least about 135, or at least about 140, or at least about 145, or at least about 150 nucleotides. In some aspects, each nucleic acid fragment in the plurality of nucleic acid fragments can comprise at least about 96 nucleotides.

In a set of overlapping nucleic acid fragments, a first nucleic acid fragment can comprise a first region that is complementary to a second nucleic acid fragment, the second nucleic acid fragment can comprise a first region that is complementary to the first nucleic acid fragment and a second region that is complementary to a third nucleic acid fragment, the third nucleic acid fragment can comprise a first region that is complementary to the second nucleic acid fragment and a second region that is complementary to a fourth nucleic acid fragment, and so on and so forth. The regions of a nucleic acid fragment that are complementary to another nucleic acid fragment in a set can be referred to as the overlap regions. The overlap regions can comprise at least about 1 nucleotide, or at least about 2 nucleotides, or at least about 3 nucleotides, or at least about 4 nucleotides, or at least about 5 nucleotides, or at least about 6 nucleotides, or at least about 7 nucleotides, or at least about 8 nucleotides, or at least about 9 nucleotides, or at least about 10 nucleotides, or at least about 11 nucleotides, or at least about 12 nucleotides, or at least about 13 nucleotides, or at least about 14 nucleotides, or at least about 15 nucleotides, or at least about 16 nucleotides, or at least about 17 nucleotides, or at least about 18 nucleotides, or at least about 19 nucleotides, or at least about 20 nucleotides, or at least about 21 nucleotides, or at least about 22 nucleotides, or at least about 23 nucleotides, or at least about 24 nucleotides, or at least about 25 nucleotides, or at least about 26 nucleotides, or at least about 27 nucleotides, or at least about 28 nucleotides, or at least about 29 nucleotides, or at least about 30 nucleotides, or at least about 31 nucleotides, or at least about 32 nucleotides, or at least about 33 nucleotides, or at least about 34 nucleotides, or at least about 35 nucleotides, or at least about 40 nucleotides, or at least about 45 nucleotides, or at least about 50 nucleotides, or at least about 60 nucleotides. In some aspects, the overlap regions can comprise 24 nucleotides.

The regions of a nucleic acid fragment that are not complementary to another nucleic acid fragment can comprise at least about 30 nucleotides, or at least about 31 nucleotide, or at least about 32 nucleotides, or at least about 33 nucleotides, or at least about 34 nucleotides, or at least about 35 nucleotides, or at least about 36 nucleotides, or at least about 37 nucleotides, or at least about 38 nucleotides, or at least about 39 nucleotides, or at least about 40 nucleotides, or at least about 41 nucleotides, or at least about 42 nucleotides, or at least about 43 nucleotides, or at least about 44 nucleotides, or at least about 45 nucleotides, or at least about 46 nucleotides, or at least about 47 nucleotides, or at least about 48 nucleotides, or at least about 49 nucleotides, or at least about 50 nucleotides, or at least about 51 nucleotides, or at least about 52 nucleotides, or at least about 53 nucleotides, or at least about 54 nucleotides, or at least about 55 nucleotides, or at least about 56 nucleotides, or at least about 57 nucleotides, or at least about 58 nucleotides, or at least about 59 nucleotides, or at least about 60 nucleotides, or at least about 61 nucleotides, or at least about 62 nucleotides, or at least about 63 nucleotides, or at least about 64 nucleotides, or at least about 65 nucleotides, or at least about 70 nucleotides, or at least about 75 nucleotides, or at least about 80 nucleotides, or at least about 85 nucleotides.

Overlapping sets of nucleic acid fragments as described herein can be used in any method of the present disclosure, as described herein.

In some aspects, in a set of overlapping nucleic acid fragments, at least one of the nucleic acid fragments can be a chimeric nucleic acid fragment comprising a deoxyribose 5' (DNA) terminus and a ribose 3' (RNA) terminus. In some aspects, at least one of the nucleic acid fragments can be a chimeric nucleic acid fragment comprising a deoxyribose 3' (DNA) terminus and a ribose 5' (RNA) terminus. In some aspects, at least one of the nucleic acid fragments can be a chimeric nucleic acid fragment comprising a deoxyribose 5'

(DNA) terminus and a deoxyribose 3' (DNA) terminus. In some aspects, at least one of the nucleic acid fragments can be a chimeric nucleic acid fragment comprising a ribose 5' (RNA) terminus and a ribose 3' (RNA) terminus.

In some aspects, the nucleic acid fragments in a set of overlapping nucleic acid fragments can be an N-mer of the present disclosure.

Methods of the Present Disclosure

Geometric Synthesis

The present disclosure provides methods of geometric synthesis of nucleic acid sequences. Methods of geometric synthesis include a geometric 3' method (also referred to as the 3' extension geometric synthesis method), a geometric 5' (also referred to as the 5' extension geometric synthesis method) method, a geometric transposase method, a geometric 3', 5' co-synthesis method (also referred to as the 5' extension and 3' extension geometric co-synthesis), a 3' extension parallel synthesis method and a 5' extension parallel synthesis method.

Figure 1:
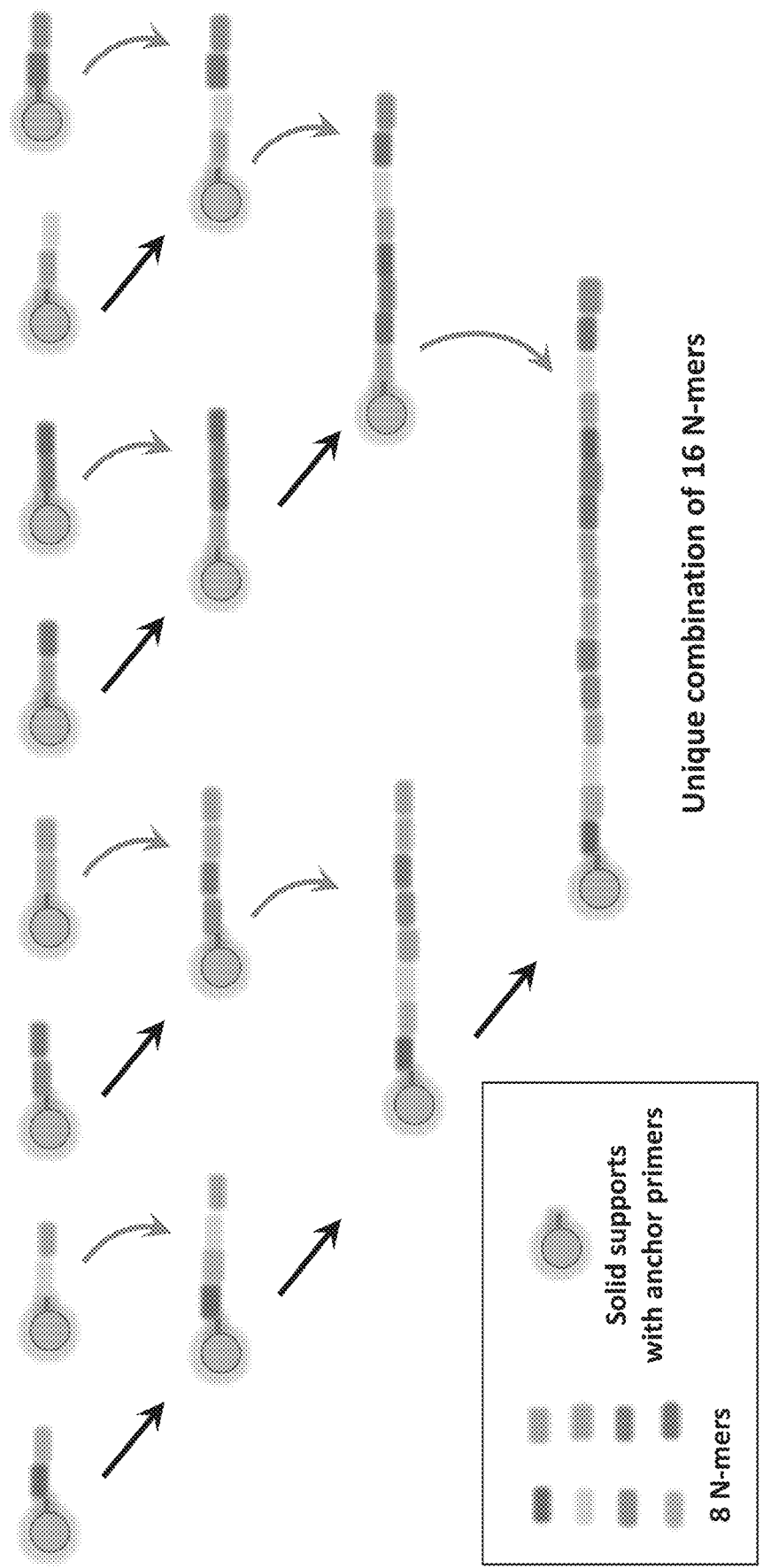
FIG. 1 is a schematic diagram depicting the central idea behind geometric synthesis. In this example eight different N-mers and the solid substrate bound anchor primer sequences are the starting materials. The first row depicts the situation after the first two rounds of ligation, wherein two N-mers have been added to anchor primers. In subsequent steps, such as row two, there are target samples, and donor samples. Target sample remain bound to solid supports and donor samples are released and used to extend corresponding target samples. After several rounds, a single target sample possesses the complete synthesized. Here the complete synthetic strand is comprised of 16 N-mer in a unique configuration.

FIGS. 1 and 15 depict a schematic overview of the geometric synthesis methods of the present disclosure. First a plurality of N-mers as described above is provided. In FIGS. 1 and 15, there are 8 different N-mer species provided. Also provided are anchor primers that are attached to solid supports. In Ligation 1, a single N-mer is ligated onto the anchor primers that are attached to the solid support to create a N-mer$_1$-anchor primer complex. In Ligation 2, a second N-mer is ligated to the exposed end of the first N-mer to extend the first N-mer and create a N-mer$_2$-anchor primer complex. After ligation, a subset of the N-mer$_2$-anchor primer complexes are designated to be donor samples and the other subset of the N-mer$_2$-anchor primer complexes are designated to be target samples. The ligated N-mers are cleaved from the anchor primers in the donor samples, releasing a nucleic acid fragment that comprises two ligated N-mers. In ligation 3, the released nucleic acid fragments are then ligated onto the exposed end of an N-mer in a target sample to extend the target sample N-mer$_2$-anchor primer complex, thereby forming a N-mer$_4$-anchor primer complex. After ligation, a subset of the N-mer$_4$-anchor primer complexes are designated to be donor samples and the other subset of the N-mer$_4$-anchor primer complexes are designated to be target samples. The ligated N-mers are cleaved from the anchor primers in the donor samples, releasing a nucleic acid fragment that comprises four ligated N-mers. In ligation 4, the released nucleic acid fragments are then ligated onto the exposed end of an N-mer in a target sample to extend the target sample N-mer$_4$-anchor primer complex, thereby forming a N-mer$_8$-anchor primer complex. After ligation, a subset of the N-mer$_8$-anchor primer complexes are designated to be donor samples and the other subset of the N-mer$_8$-anchor primer complexes are designated to be target samples. The ligated N-mers are cleaved from the anchor primers in the donor samples, releasing a nucleic acid fragment that comprises eight ligated N-mers. In ligation 5, the released nucleic acid fragments are then ligated onto the exposed end of an N-mer in a target sample to extend the target sample N-mer$_8$-anchor primer complex, thereby forming a N-mer$_{16}$-anchor primer complex.

3' Extension Geometric Synthesis

The present disclosure provides a 3' extension geometric synthesis method. A 3' extension geometric synthesis method is a geometric synthesis as described in FIGS. 1 and 15, wherein the anchor primers are attached to the solid support via their 5' termini, thereby leaving their 3' termini exposed for ligation and extension.

In a 3' extension geometric synthesis method, a plurality of N-mers as described above is provided, wherein the N-mers comprise a —PO$_4$ group at the 3' terminus and the 5' terminus. Also provided are anchor primers that are attached to a solid support via their 5' terminus. Thus, the 3' termini of the anchor primers, which comprise an —OH group, are exposed for ligation and extension.

A 3' extension geometric synthesis method can comprise the steps:

1) ligating an N-mer species onto the exposed 3' terminus of the anchor primers;

2) optionally incubating the ligation products from step (1) with a 3' to 5' specific exonuclease, such as Klenow polymerase, to remove un-ligated anchor primers from the solid supports. A polymerase such as a Klenow polymerase cannot digest nucleic acid molecules comprising a 3' —PO$_4$ group;

3) incubating the samples from step (2) with a phosphatase, such as calf intestinal alkaline phosphatase (CIP) or shrimp alkaline phosphatase (SAP) to remove the 3' —PO$_4$ from the ligated N-mers;

4) ligating a second N-mer to the 3' terminus of an N-mer ligated in step 1;

5) optionally incubating the ligation products from step (4) with a 3' to 5' specific exonuclease, such as Klenow polymerase, to remove un-ligated anchor primers from the solid supports;

6) designating a subset of the samples from step (5) as donor samples and a subset of samples from step (5) as target samples;

7) incubating the target samples from step (6) with a phosphatase such as calf intestinal alkaline phosphatase (CIP) or shrimp alkaline phosphatase (SAP) to remove 3' —PO$_4$ groups;

8) releasing the ligated N-mers in the donor samples from the anchor primer to which they are ligated, wherein releasing preserves both 3' and 5' —PO$_4$ groups;

9) ligating the released ligated N-mers from step (8) to the target samples from step (7); 10) repeating steps 5-9 with the ligation products from step (9).

In a 3' extension geometric synthesis method, step (10) can be repeated until the desired nucleic acid fragment has been synthesized. The desired nucleic acid fragment can then be released from the anchor primer to which it is ligated.

FIGS. 3-8 show a schematic overview of an exemplary synthesis of a nucleic acid molecule using a 3' extension geometric synthesis method of the present disclosure. The nucleic acid to be synthesized comprises a fragment of the *Aequorea victoria* green-fluorescent protein (GFP). FIG. 3A shows the entire coding region of the *A. victoria* GFP. The fragment to be synthesized is depicted in colored font and comprises the sequence:

```
                                              (SEQ ID NO: 1)
TACACACGAATAAAAGATAACAAAGATGAGTAAAGGAGAAGAACTTTTCAC

TGGAGTTGTCCCAATTCTTGTTGAATTAGATGGCGATGTTAATGGGCAAAA

ATTCTCTGTCAGTGGAGAGGGTGAAGGTGATGCAACATACGGAAAACTTAC

CCTTAAATTTATTTGCACTACTGGGAAGCTACCTGTTCCATGGCCAACACT

TGTCAC.
```

The fragment to be synthesized is subdivided into eight N-mers, wherein each N-mer comprises 21 nucleotides. The N-mers are depicted in different colored font in FIG. 3A.

The rest of the A. victoria GFP sequence can also be subdivided into N-mers comprising 21 nucleotides.

For the purposes of explaining this example, each N-mer is assigned an identifier code as shown in Table 1.

TABLE 1

N-mer sequences and identifier codes

| Identifier code | Sequence | SEQ ID NO |
|---|---|---|
| 1aA1 | TACACACGAATAAAAGATAAC | 2 |
| 1aA2 | ACTTTTCACTGGAGTTGTCCC | 3 |
| 1aA3 | CGATGTTAATGGGCAAAAATT | 4 |
| 1aA4 | AGGTGATGCAACATACGGAAA | 5 |
| 1bA1 | AAAGATGAGTAAAGGAGAAGA | 6 |
| 1bA2 | AATTCTTGTTGAATTAGATGG | 7 |
| 1bA3 | CTCTGTCAGTGGAGAGGGTGA | 8 |
| 1bA4 | ACTTACCCTTAAATTTATTTG | 9 |

Figure 4:
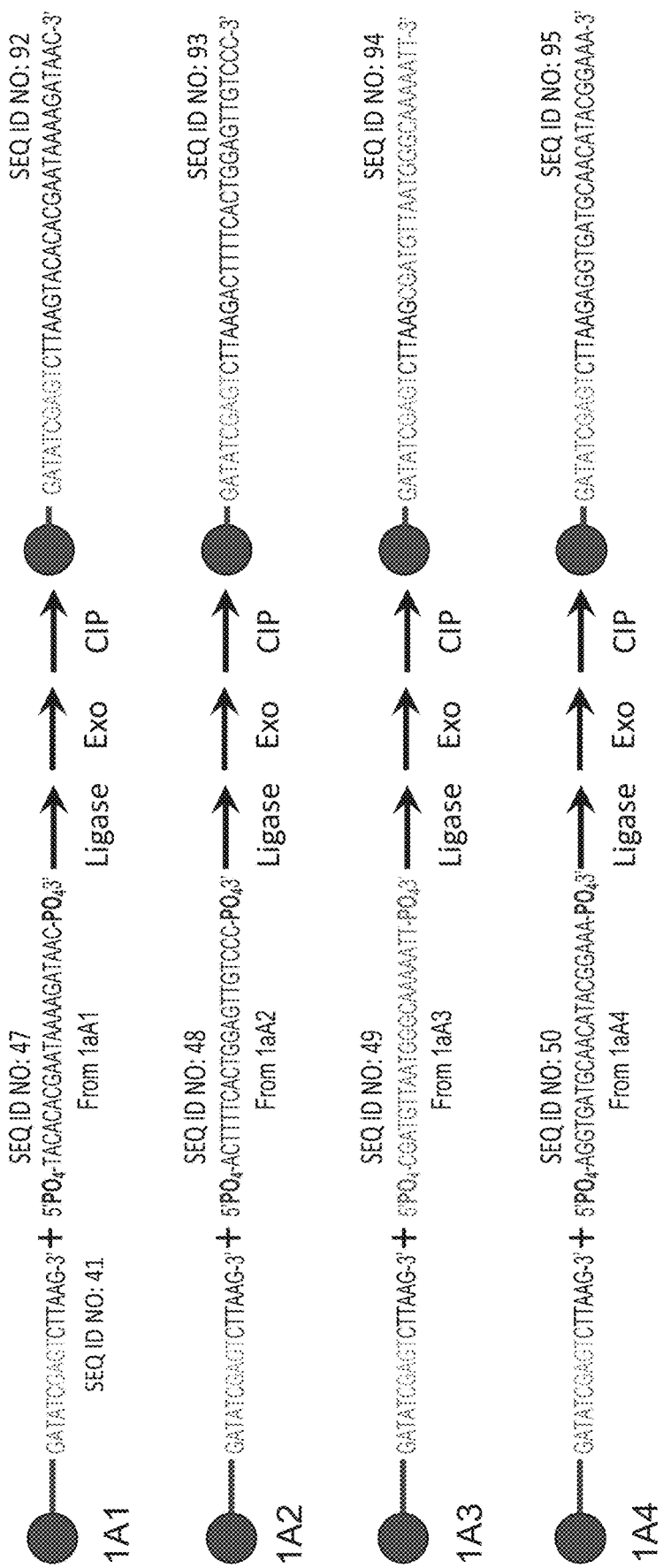
FIG. 4 is a schematic representation of the first ligation step. In this example the wells 1A1, 1A2, 1A3 and 1A4 receive a 21-mer fragment with 3' and 5' —$PO_4$, ligase is added to the reactions. After ligation Klenow polymerase with 3'-5' exonuclease activity is added to remove un-ligated anchor primers. Finally, calf intestinal alkaline phosphatase (CIP) is added to remove 3' —$PO_4$ groups to prepare the NA for the second round of ligation.

The synthesis method continues by providing a plurality of anchor primers attached to solid supports, as shown in FIG. 4. In this example, the solid supports are beads and the anchor primers comprise the sequence GATATCGAGTCT-TAAG (SEQ ID NO: 91).

N-mers 1aA1, 1aA2, 1aA3, and 1aA4 are then provided with a 3' and a 5' —PO₄ group. N-mers 1aA1, 1aA2, 1aA3, and 1aA4 are then ligated onto the exposed 3' end of the anchor primers as shown in FIG. 4. Following ligation, a polymerase with 3'-5' exonuclease activity, such as klenow polymerase, is added to remove any un-ligated anchor primers. Calf intestinal alkaline phosphatase (CIP) is then added to remove the 3' —PO₄ group on each of the ligated fragments. This step of synthesis results in nucleic acid fragments comprising the anchor primer and one of N-mers 1aA1, 1aA2, 1aA3, and 1aA4 attached to a solid bead, as shown in the right panel of FIG. 4.

Figure 5:
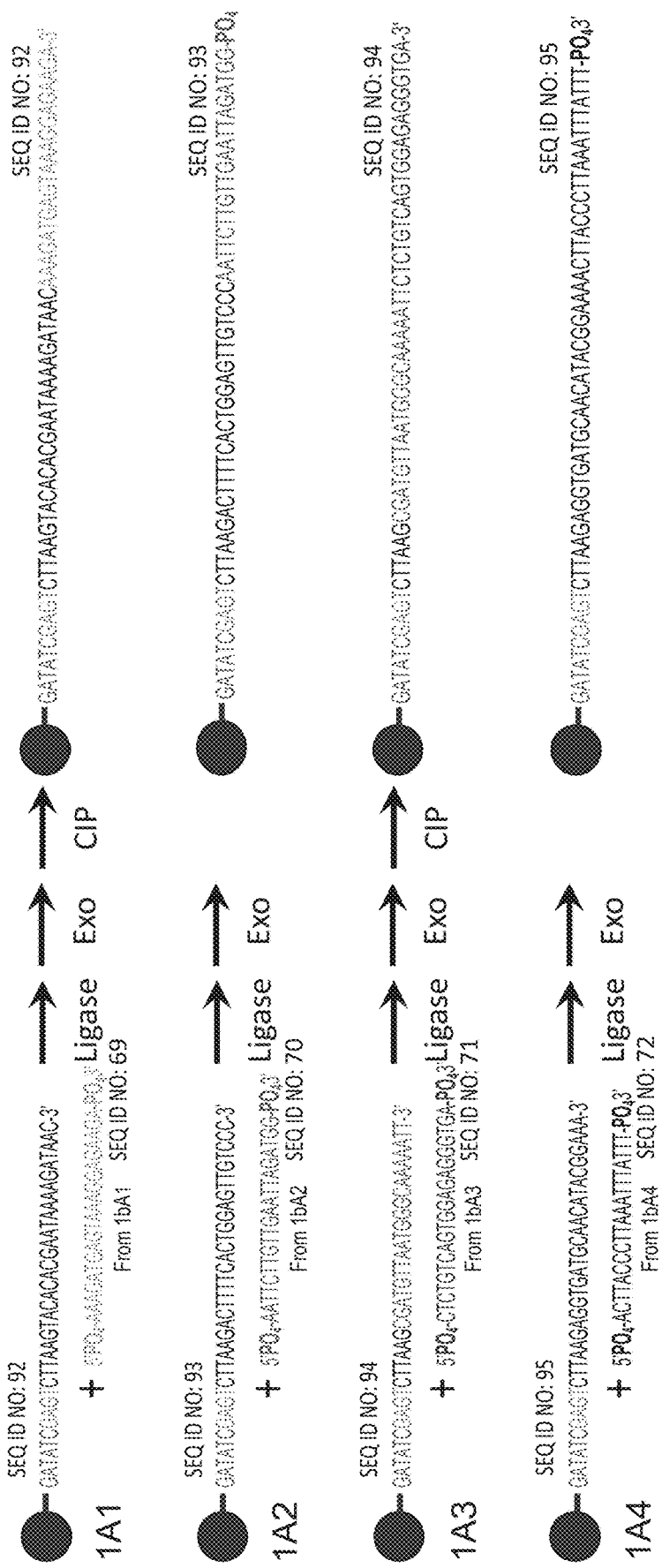
FIG. 5 is a schematic representation of the second ligation step. As with the first ligation step, the wells 1A1, 1A2, 1A3 and 1A4 each receive a 21-mer fragment bearing 3' and 5' —$PO_4$ groups, ligase is added to the reactions. After elongation by ligation, Klenow polymerase with 3'-5' exonuclease activity is added to remove un-ligated anchor primers. Finally, calf intestinal alkaline phosphatase (CIP) is added to 1A1 and 1A3 remove 3' —$PO_4$ groups to prepare the NA in those wells as targets for the next ligation. Wells 1A2 and 1A4 are left bearing 3' —$PO_4$ groups.

The synthesis method continues in FIG. 5. N-mer 1bA1, 1bA2, 1bA3, and 1bA4 are then provided with a 3' and a 5' —PO₄ group. The 5' end of N-mer 1bA1 is ligated onto the 3' end of N-mer 1aA1, the 5' end of N-mer 1bA2 is ligated onto the 3' end of N-mer 1aA2, the 5' end of N-mer 1bA3 is ligated onto the 3' end of N-mer 1aA3, the 5' end of N-mer 1bA4 is ligated onto the 3' end of N-mer 1aA4, as shown in the left panel of FIG. 5. Following ligation, a polymerase with 3'-5' exonuclease activity, such as klenow polymerase, is added to remove any un-ligated anchor primers. For the ligated 1aA1-1bA1 fragment and the ligated 1aA3-1bA3 fragment, Calf intestinal alkaline phosphatase (CIP) is then added to remove the 3' —PO₄ group on each of the ligated fragments. This step of synthesis results in the following nucleic acid fragments ligated to an anchor primer which is attached to a solid bead: a 1aA1-1bA1 fragment (1A1 fragment), a 1aA2-1bA2 fragment (1A2 fragment), a 1aA3-1bA3 fragment (1A3 fragment) and a 1aA4-1bA4 fragment (1A4 fragment). The anchor primer-1aA1-1bA1 fragment and the anchor primer-1aA3-1bA3 fragment do not have a 3' —PO₄ group. The anchor primer-1aA2-1bA2 fragment and the anchor primer-1aA4-1bA4 fragment do have a 3' —PO₄ group. The products of this synthesis step are shown in the right panel of FIG. 5.

Figure 6:
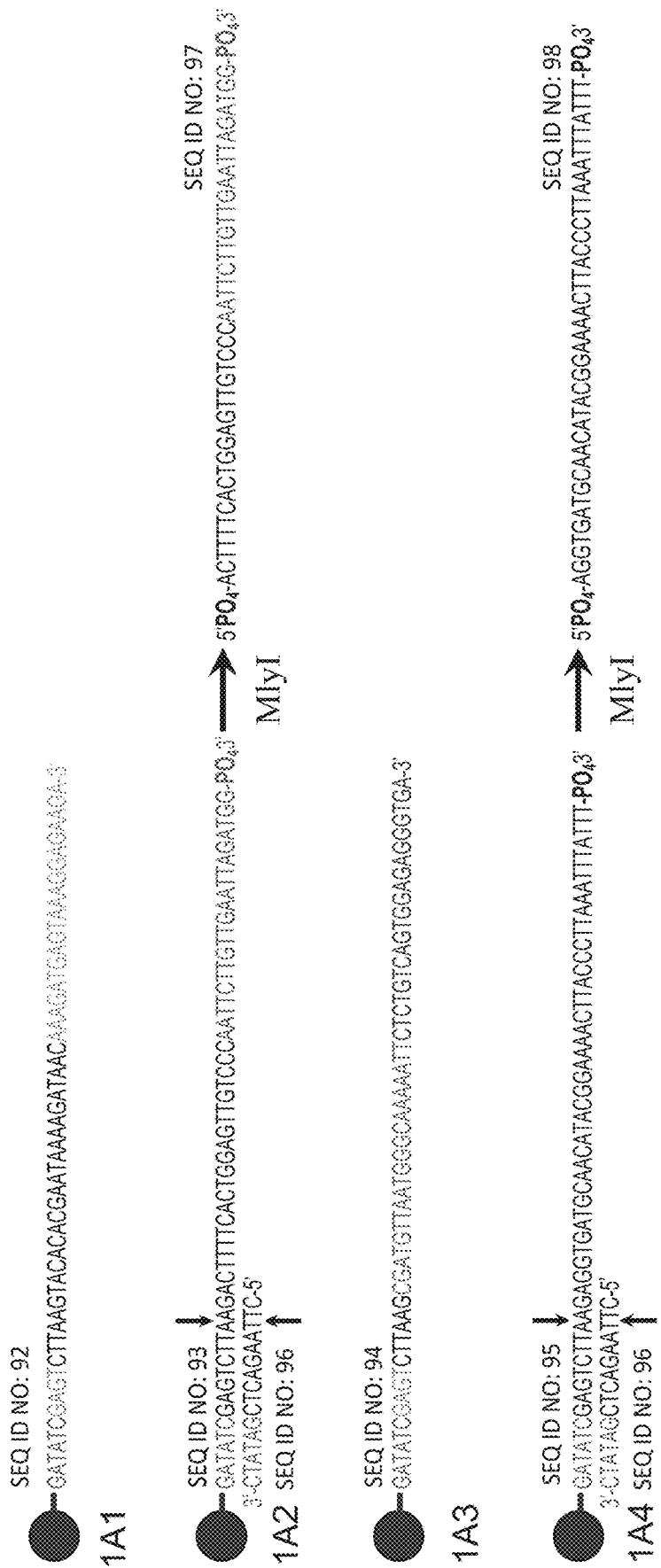
FIG. 6 is a schematic representation of the first release reaction. Donor samples 1A2 and 1A4 are first mixed with short reverse complementing oligo nucleotides, which generate double stranded MlyI sites on partially double stranded DNA. These samples are then digested with MlyI restriction endonuclease, at which point the released single stranded newly synthesized fragment is ready for ligation to the appropriate target sample. In this instance, the released fragment from 1A2 will be ligated to target sample 1A1 and the fragment from 1A4 will be ligated to target sample 1A3.

The synthesis method continues in FIG. 6. The 1A2 sample and the 1A4 samples are to be donor samples in the next synthesis round. Thus, a short reverse complementary oligonucleotide is mixed with the 1A2 sample and the 1A4 sample. The short reverse complementary oligonucleotide comprises the sequence CTATAGCTCAGAATTC (SEQ ID NO: 96) and is complementary to the anchor primer. The short reverse complementary oligonucleotide hybridizes to the anchor primer such that a double-stranded restriction endonuclease site is formed. In this example, the restriction endonuclease site is a MlyI restriction endonuclease site. After hybridization of the short reverse complementary oligonucleotide, the 1A2 sample and the 1A4 sample are incubated with MlyI restriction endonuclease, which cleaves at the MlyI restriction site, resulting in the release of the 1A2 fragment and 1A4 fragment.

Figure 7:
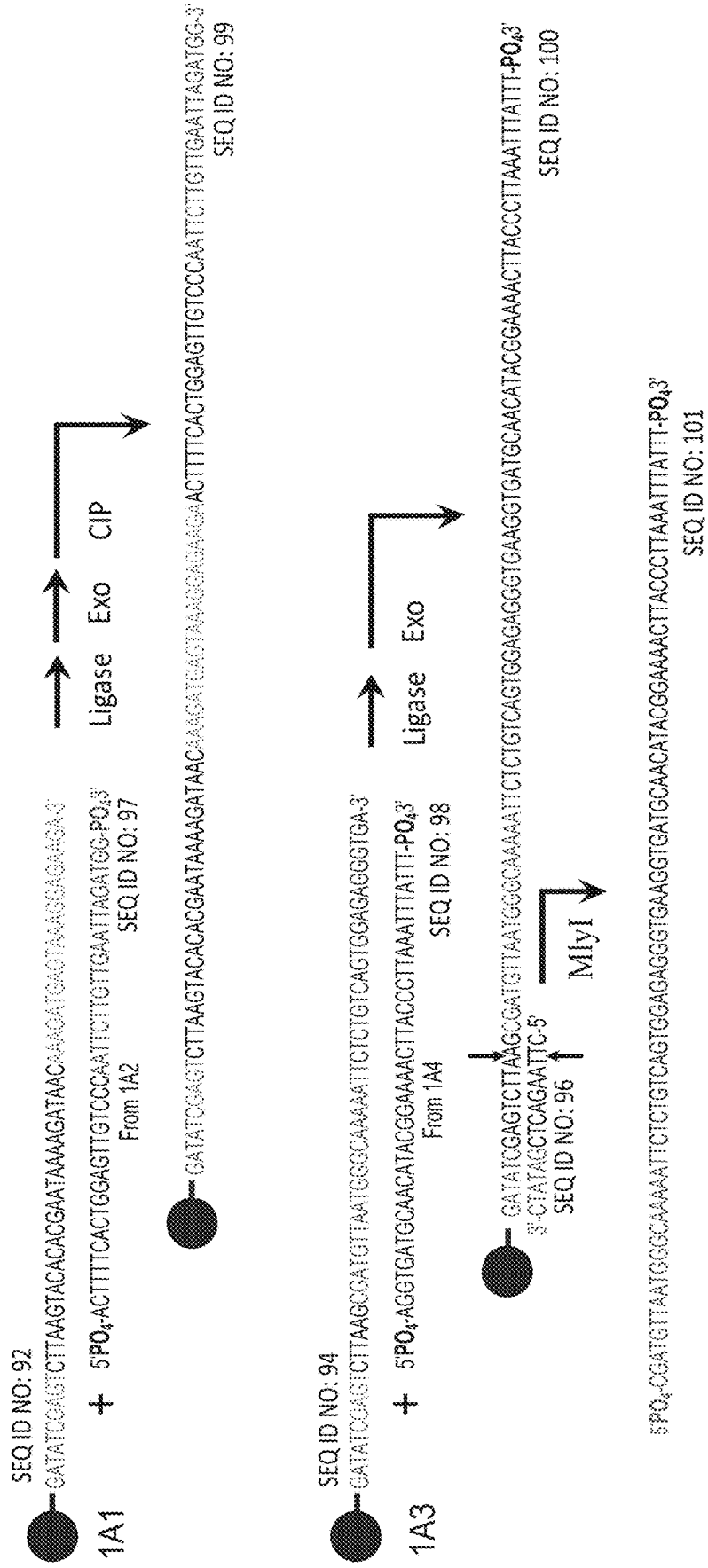
FIG. 7 is a schematic representation of the third ligation, which will combine extend the NA in 1A1 by ligation of the synthesized NA from 1A2, well as extend the NA of 1A3 by with the NA from 1A4. Finally, the product NA from 1A3 is released by cleavage with MlyI.

The synthesis method continues in FIG. 7. The 5' end of the 1A2 fragment is ligated onto the 3' end of the 1A1 fragment that is attached to the solid support to form a 1A1-1A2 fragment and the 5' end of the 1A4 fragment is ligated onto the 3' end of the 1A3 fragment that is attached to the solid support to form a 1A3-1A4 fragment. Following ligation, a polymerase with 3'-5' exonuclease activity, such as klenow polymerase, is added to remove any un-ligated anchor primers. For the ligated 1A1-1A2 fragment, Calf intestinal alkaline phosphatase (CIP) is then added to remove the 3' —PO₄ group on the fragment. The 1A3-1A4 fragment is then incubated with the short reverse complementary oligonucleotide, which hybridizes to the anchor primer to form a double-stranded restriction endonuclease site. In this example, the site is a MlyI site. After hybridization of the short reverse complementary oligonucleotide, the sample is incubated with MlyI restriction endonuclease, which cleaves the MlyI restriction site to release the 1A3-1A4 fragment, as shown in the bottom panel of FIG. 7.

Figure 8:
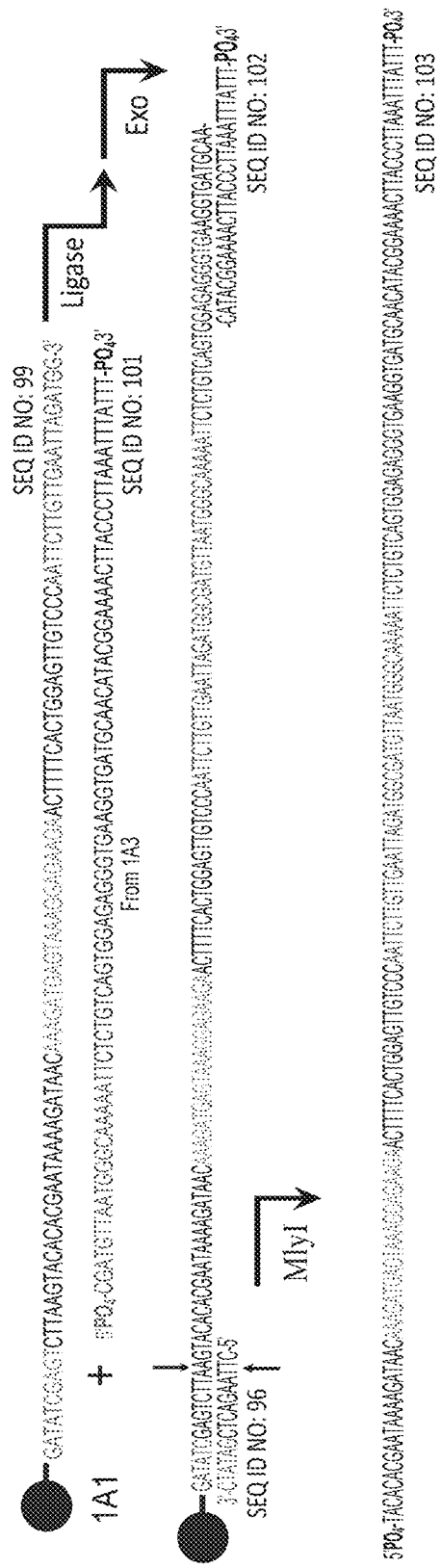
FIG. 8 is a schematic representation of the fourth and final ligation for this example. The NA product of sample 1A3 is ligated to the extended NA of well 1A1. After cleanup, the final product NA is released from solid supports by digestion with MlyI.
Figure 9:
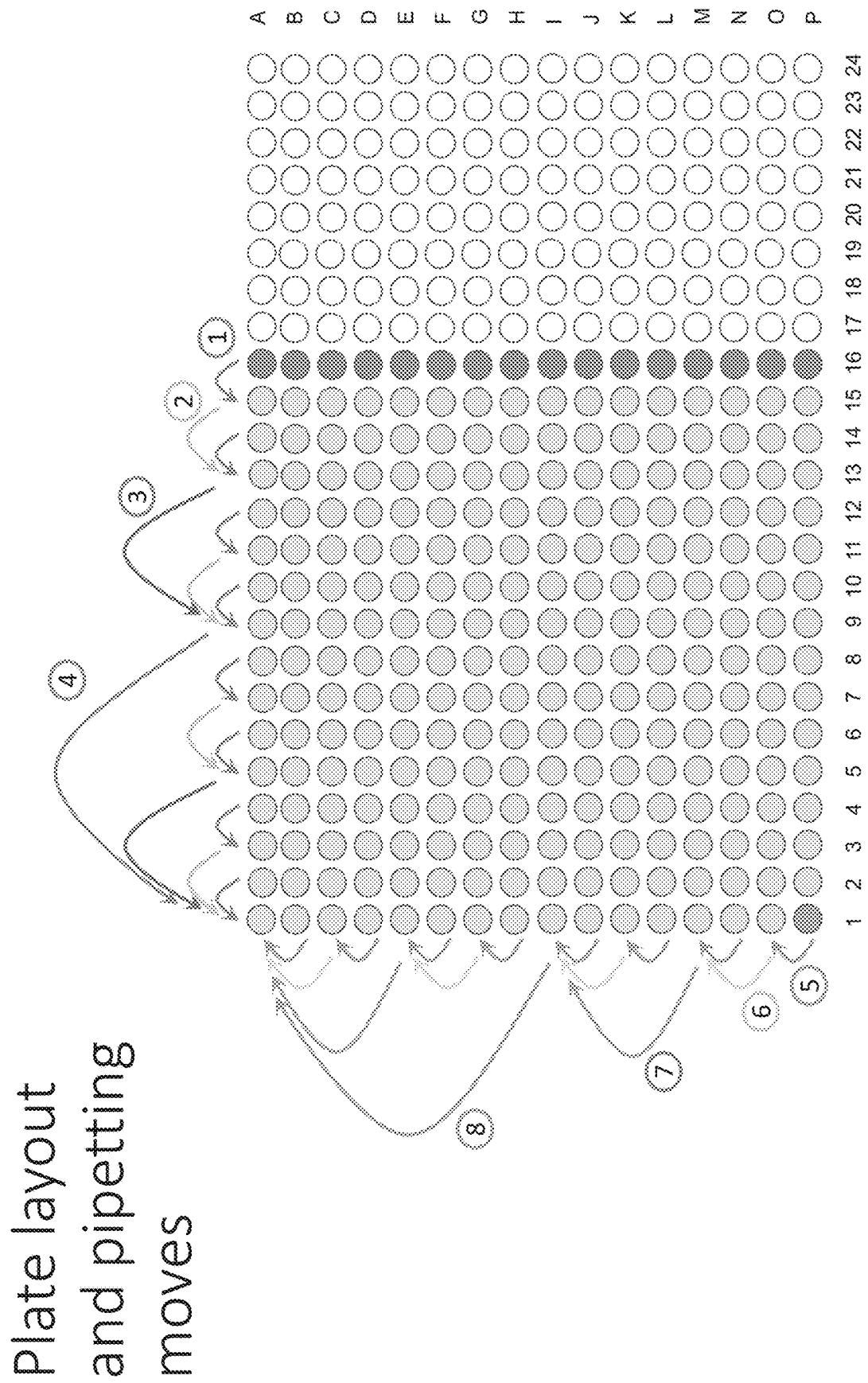
FIG. 9 shows a plate layout and pipetting moves. In this example, a 384 well plate is depicted with 16×16 wells (A1-P16) being used. There are two phases to the transfers.

The synthesis method continues in FIG. 8. The 5' end of the 1A3-1A4 fragment is ligated to the 3' end of the 1A1-1A2 fragment that is attached to the solid support to form a 1A1-1A2-1A3-1A4 fragment. Following ligation, a polymerase with 3'-5' exonuclease activity, such as klenow polymerase, is added to remove any un-ligated anchor primers. The 1A1-1A2-1A3-1A4 fragment is then incubated with short reverse complementary oligonucleotide, which hybridizes to the anchor primer to form a double-stranded restriction endonuclease site. In this example, the site is a MlyI site. After hybridization of the short reverse complementary oligonucleotide, the sample is incubated with MlyI restriction endonuclease, which cleaves the MlyI restriction site to release the 1A1-1A2-1A3-1A4 fragment (the fragment that was to be synthesized), as shown in the bottom panel of FIG. 8.

3' Extension Parallel Synthesis Method

The present disclosure provides a 3' extension parallel synthesis method. In a 3' extension parallel synthesis method, a plurality of 3' extension geometric synthesis reactions, as described above, are performed using N-mers and/or anchor primers that comprise a reversible block on the 3' —OH group. The plurality of reactions can be performed on a solid support comprising chambers that are arranged in a two-dimensional grid. At different stages of synthesis, certain reactions are allowed to proceed by removing the reversible block on the 3' —OH group in a particular chamber within the grid, thereby allowing the user to control what N-mer is incorporated in each step.

In a non-liming example, a two-dimensional grid of reactions may begin with general attachment of 3' reversibly blocked anchor primers. If the incorporation of a specific N-mer, such as ACG, is required, then the region of the two-dimensional grid where the N-mer with the sequence ACG is required is unblocked, allowing the ACG N-mer to be incorporated only there. Such a process ensues for all 64 possible 3-mers suitably blocked at the 3' end. Any possible sequence combination can be manifest at any specific location on the grid.

In a non-limiting example, the reversible block may be removed by exposure to light. Thus, a two-dimensional grid of reactions may begin with general attachment of 3' reversibly blocked anchor primers. If the incorporation of a specific N-mer, such as ACG, is required, then the region of the two-dimensional grid where the N-mer with the sequence ACG is required is exposed to light, removing the reversible block in that region, allowing the ACG N-mer to be incorporated only there.

5' Extension Geometric Synthesis Method

The present disclosure provides a 5' extension geometric synthesis method. A 5' extension geometric synthesis method is a geometric synthesis as described in FIGS. 1 and 15, wherein the anchor primers are attached to the solid support via their 3' termini, thereby leaving their 5' termini exposed for ligation and extension. In some aspects of the 5' extension geometric synthesis method, a plurality of N-mers as described above is provided, wherein the N-mers comprise a —OH group at the 3' terminus and the 5' terminus. Also provided are anchor primers that are attached to a solid support via their 3' terminus. Thus, the 5' termini of the anchor primers, which comprise an —$PO_4$ group, are exposed for ligation and extension.

A 5' extension geometric synthesis method can comprise the steps:

1) ligating an N-mer species onto the exposed 5' terminus of the anchor primers;

2) optionally, incubating the ligation products from step (1) with a 5' to 3' specific exonuclease, such as lambda exonuclease, to remove un-ligated anchor primers from the solid supports. Lambda exonuclease cannot digest nucleic acid molecules comprising a 5' —OH group.

3) optionally incubating the samples from step (2) with polynucleotide kinase (PNK), to produce a —$PO_4$ group at each 5' terminus;

4) ligating a second N-mer to the 5' terminus of an N-mer ligated in step 1;

5) optionally, incubating the ligation products from step (4) with a 5' to 3' specific exonuclease, such as lambda exonuclease, to remove un-ligated anchor primers from the solid supports;

6) designating a subset of the samples from step (5) as donor samples and a subset of samples from step (5) as target samples;

7) optionally incubating the target samples from step (6) with polynucleotide kinase (PNK), to produce a —$PO_4$ group at each 5' terminus;

8) releasing the ligated N-mers in the donor samples from the anchor primer to which they are ligated, wherein releasing preserves both 3' and 5' —OH groups;

9) ligating the released ligated N-mers from step (8) to the target samples from step (7);

10) repeating steps 5-9 with the ligation products from step (9).

In a 5' extension geometric synthesis method, step (10) can be repeated until the desired nucleic acid fragment has been synthesized. The desired nucleic acid fragment can then be released from the anchor primer to which it is ligated.

In some aspects of the 5' extension geometric synthesis method of the present disclosure, a plurality of N-mers as described above is provided, wherein the N-mers comprise an —OH group at the 3' terminus and a —$PO_4$ at the 5' terminus. The —$PO_4$ group can be attached a protecting group.

5' Extension Parallel Synthesis Method

The present disclosure provides a 5' extension parallel synthesis method. In a 5' extension parallel synthesis method, a plurality of 5' extension geometric synthesis reactions, as described above, are performed using N-mers and/or anchor primers that comprise a reversible block on the 5' —$PO_4$ group. The plurality of reactions can be performed on a solid support comprising chambers that are arranged in a two-dimensional grid. At different stages of synthesis, certain reactions are allowed to proceed by removing the reversible block on the 5' —$PO_4$ group in a particular chamber within the grid, thereby allowing the user to control what N-mer is incorporated in each step.

In a non-liming example, a two-dimensional grid of reactions may begin with general attachment of 5' reversibly blocked anchor primers. If the incorporation of a specific N-mer, such as ACG, is required, then the region of the two-dimensional grid where the N-mer with the sequence ACG is required is unblocked, allowing the ACG N-mer to be incorporated only there. Such a process ensues for all 64 possible 3-mers suitably blocked at the 5' end. Any possible sequence combination can be manifest at any specific location on the grid.

In a non-limiting example, the reversible block may be removed by exposure to light. Thus, a two-dimensional grid of reactions may begin with general attachment of 5' reversibly blocked anchor primers. If the incorporation of a specific N-mer, such as ACG, is required, then the region of the two-dimensional grid where the N-mer with the sequence ACG is required is exposed to light, removing the reversible block in that region, allowing the ACG N-mer to be incorporated only there.

Geometric Transposase Method

The present disclosure provides a geometric transposase method. A geometric transposase method comprises the use of a collection of plasmids with reverse oriented left and right terminal repeats derived from a precisely excising transposable element, such as piggyBac, as shown in the bottom panel FIG. 12. Each plasmid in the collection carries a different N-mer (e.g. a 3-, 4-, and 5-mers) that is flanked by reverse oriented left and right terminal repeats. An N-mer flanked by reverse oriented left and right terminal repeats is herein referred to as a transposable N-mer.

In a geometric transposase method, each required transposable N-mer is excised from its plasmid backbone by an appropriate restriction endonuclease (RE) or similar digestion along with the flanking reverse oriented left and right terminal repeats, as shown in the top panel of FIG. 12. A plurality of anchor primers attached to a solid support are then provided.

In some aspects, a geometric transposase method can comprise:

1) ligating a transposable N-mer to an anchor primer attached to a solid support;

2) optionally, cleaning up the reaction from step (1);

3) ligating a second transposable N-mer to a transposable N-mer ligated in step (1);

4) optionally, cleaning up the reaction from step (3);

5) incubating the products of step (4) with a transposase to excise the intervening sequence between the two ligated N-mer sequences;

6) designating a subset of the samples from step (5) as donor samples and a subset of samples from step (5) as target samples;

7) releasing the N-mers in the donor samples from the anchor primer to which they are ligated;

8) ligating the released ligated N-mers from step (8) to the target samples from step (7);

9) cleaning up the reaction from step (8);

10) repeating steps 5-9 with the products of step (9).

FIG. 13 shows a schematic overview of a geometric transposase method of the present disclosure.

In a geometric transposase method, step (10) can be repeated until the desired nucleic acid fragment has been synthesized. The desired nucleic acid fragment can then be released from the anchor primer to which it is ligated.

Geometric 3', 5' Co-Synthesis Method

The present disclosure provides a geometric 3', 5' co-synthesis method. A geometric 3', 5' co-synthesis method comprises the use of a set of overlapping nucleic acid fragments, as described above. The bottom panel of FIG. 10 shows a set of six overlapping nucleic acid fragments.

The top panel of FIG. 11 shows a set of 16 overlapping nucleic acid fragments. A geometric 3', 5' co-synthesis method can comprise:

1) annealing the overlapping set of nucleic acid fragments together;

2) performing polymerase extension reactions to extend the 3' end of each of the annealed nucleic acid fragments;

3) ligating the extended fragments from step (2) together.

FIG. 11 shows a schematic overview of a geometric 3', 5' co-synthesis method.

In a geometric 3', 5' co-synthesis method, the set of overlapping nucleic acid fragments can be generated using any method of the present disclosure, including but not limited to, a geometric transposase method of the present disclosure, a 3' extension geometric synthesis method of the present disclosure, a 5' extension geometric synthesis method or any combination thereof.

5' Modular Linear Synthesis Method

Figure 18:
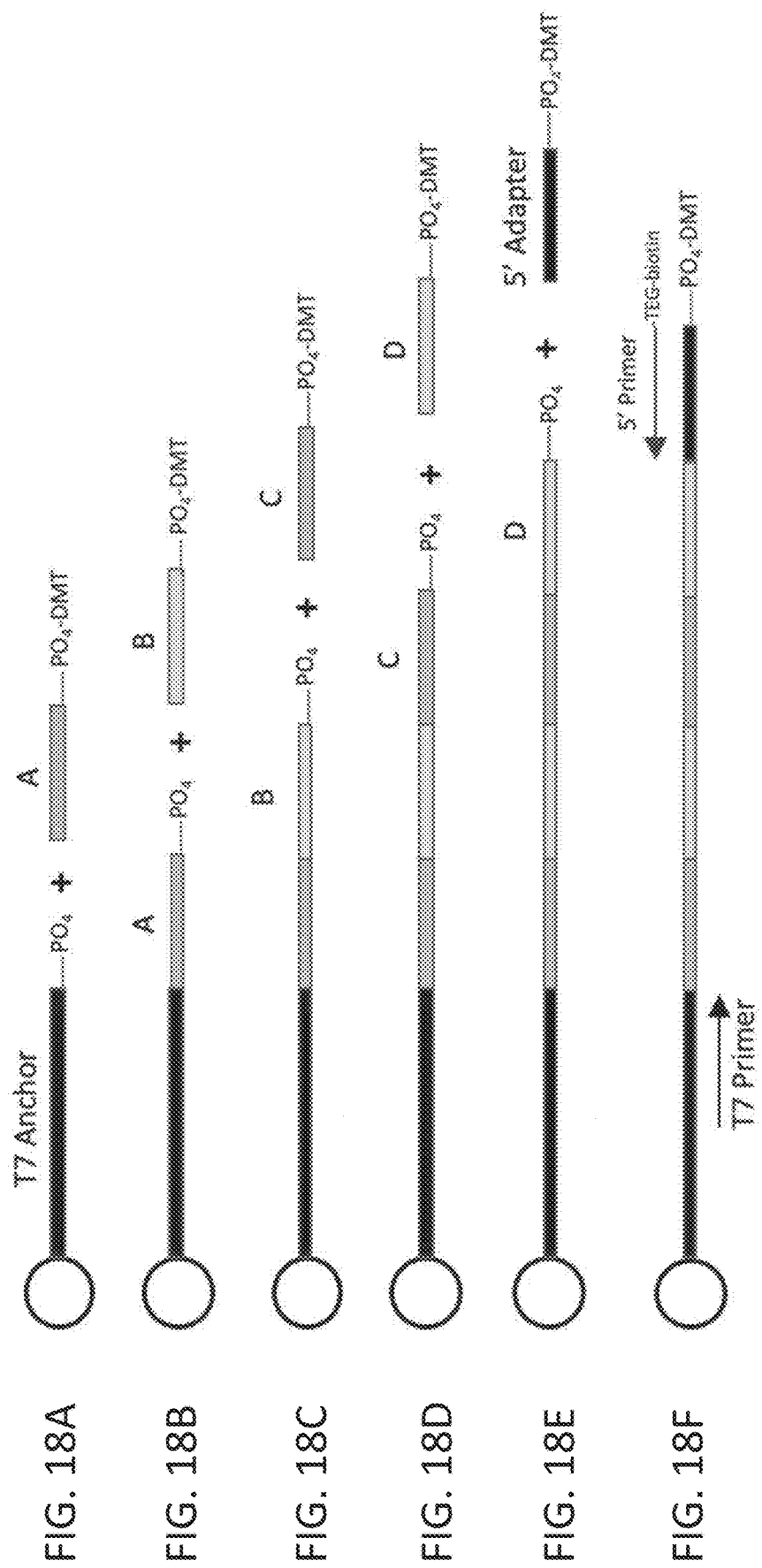

The present disclosure also provides a 5' modular linear synthesis method. FIG. 18 depicts a schematic overview of the 5' modular linear synthesis method of the present disclosure. In a 5' modular linear synthesis method, an anchor primer is first attached to a solid support, either directly or indirectly, via the 3' terminus of the anchor primer. After the anchor primer is attached, the next step of the 5' modular synthesis method is to ligate the 3' terminus of an N-mer of the present disclosure to the 5' terminus of the anchor primer attached to the solid support. This step is shown in panel A of FIG. 18, where an N-mer labeled "A" is ligated onto an anchor primer referred to as a "T7 Anchor". Following the first ligation step, any optional protecting groups on the 5' terminus of the ligated N-mer can be removed prior to the next ligation step.

The method continues with the ligation of the 3' terminus of a second N-mer to the 5' end of the ligated first N-mer. This step is shown in panel B of FIG. 18, where an N-mer labeled "B" is ligated onto the "A" N-mer. Following this second ligation step, any optional protecting groups on the 5' terminus of the newly ligated N-mer can be removed prior to the next ligation step.

The method continues with the ligation of the 3' terminus of a third N-mer to the 5' end of the ligated second N-mer. This step is shown in panel C of FIG. 18, where an N-mer labeled "C" is ligated onto the "B" N-mer. Following this third ligation step, any optional protecting groups on the 5' terminus of the newly ligated N-mer can be removed prior to the next ligation step.

The method continues with the ligation of the 3' terminus of a fourth N-mer to the 5' end of the ligated third N-mer. This step is shown in panel D of FIG. 18, where an N-mer labeled "D" is ligated onto the "C" N-mer.

In some aspects, the ligation steps in the 5' modular linear synthesis method can be repeated as many times as necessary using the appropriate N-mers to generate any full length nucleotide sequence.

3' Modular Linear Synthesis Method

The present disclosure also provides a 3' modular linear synthesis method. In a 3' modular linear synthesis method, an anchor primer is first attached to a solid support, either directly or indirectly, via the 5' terminus of the anchor primer. After the anchor primer is attached, the next step of the 3' modular synthesis method is to ligate the 5' terminus of an N-mer of the present disclosure to the 3' terminus of the anchor primer attached to the solid support. Following the first ligation step, any optional protecting groups on the 3' terminus of the ligated N-mer can be removed prior to the next ligation step.

The method continues with the ligation of the 5' terminus of a second N-mer to the 3' end of the ligated first N-mer. Following this second ligation step, any optional protecting groups on the 3' terminus of the newly ligated N-mer can be removed prior to the next ligation step.

The method continues with the ligation of the 5' terminus of a third N-mer to the 3' end of the ligated second N-mer. Following this third ligation step, any optional protecting groups on the 3' terminus of the newly ligated N-mer can be removed prior to the next ligation step.

The method continues with the ligation of the 5' terminus of a fourth N-mer to the 3' end of the ligated third N-mer.

In some aspects, the ligation steps in the 3' modular linear synthesis method can be repeated as many times as necessary using the appropriate N-mers to generate any full length nucleotide sequence.

General Methods

In all methods of the present disclosure, N-mers and/or anchor primers can comprise a deoxyribose 5' (DNA) terminus and a ribose 3' (RNA) terminus. N-mers and/or anchor primers that comprise deoxyribose 5' (DNA) termini and a ribose 3' (RNA) termini exhibit increased ligation effinices as compared to the ligation of two fragments both 5' and 3' deoxyribose (DNA) termini or both 5' and 3' ribose (RNA) termini.

In all methods of the present disclosure, following any ligation reaction, any ligated N-mers can be adenylated at the 5' terminus. The N-mers can be adenylated using methods known in the art, including, but not limited to, treating the N-mers with Mth RNA ligase.

In all methods of the present disclosure, following any ligation reaction, any ligated N-mers can be phosphorylated at the 5' terminus. The N-mers can be phosphorylated using methods known in the art, including, but not limited to, treating the N-mers with T4 polynucleotide kinase.

In all methods of the present disclosure, un-ligated N-mers and unattached anchor primers can be digested and removed using an exonuclease. In some aspects of 5' extension methods of the present disclosure, a 5' to 3' exonuclease can be used to digest and remove un-ligated N-mers and unattached anchor primers. In some aspects of 3' extension methods of the present disclosure, a 3' to 5' exonuclease can be used to digest and remove un-ligated N-mers In all methods of the present disclosure, prior to any exonuclease digestion reaction, the N-mers and/or ligated N-mers to be digested can be de-adenylated. De-adenylation can be accomplished using methods known in the art, including, but not limited to, treating the N-mers with *S. cerevisiae* 5' deadenylase.

In all methods of the present disclosure, protecting groups located on the 5' or 3' end of an N-mer can be removed using methods known in the art. These methods can include, but are not limited to, acid and base washing steps.

EXAMPLES

Example 1: 5' Extension Geometric Synthesis

The following is an example that uses the 5' extension geometric synthesis method of the present disclosure to generate a sequence template of an RNA aptamer referred to as "Baby Spinach". Baby Spinach enhances the fluorescence of 3,5-difluoro-4-hydroxybenzylidne imidazolinone (DFHBI), a compound that mimics the fluorescent core of fluorescent protenis like green fluorescent proteins (GFP).

First, two distinct reactions were established in which a 3' biotinylated anchor primer comprising single stranded DNA was attached to streptavidin-coated, magnetic beads.

In the first reaction, herein referred to as the "AB reaction", the anchor primer comprised a 5' phosphate group followed by a T7 promoter sequence (CTATAGTGAGTCGTATTA, SEQ ID NO: 10), followed by a DNA sequence spacer, followed by a tetraethylene glycol (TEG) spacer covalently linked to a biotin moiety. This anchor primer, herein referred to as the "AB anchor primer" comprised the sequence CTATAGTGAGTCGTATTACCGTAGTGCTGCGTCGAGTGT (SEQ ID: 11).

In the second reaction, herein referred to as the "CD reaction", the anchor primer comprised a 5' phosphate group linked to a deoxyuracil nucleotide, followed by a DNA sequence spacer, followed by a tetraethylene glycol (TEG) spacer covalently linked to a biotin moiety. This anchor primer, herein referred to as the "CD anchor primer", comprised the sequence dUCCATTGTGAGTCTTATTTCCGTAGTGCTGCGTCGAGTGTC (SEQ ID NO: 12).

In the AB reaction and the CD reaction, each biotinylated anchor primer was attached to the streptavidin-coated, magnetic beads (MyOne Dynal, Invitrogen) by incubating 500 pmols of the anchor primer for each 1 mg of beads used, such that the concentration of anchor primer in the reaction was 1 µM and the concentration of beads was 2 mg/ml. The incubation buffer comprised phosphate-buffered saline (PBS) with 0.01% TWEEN20. The reactions were incubated for 30 minutes at room temperature and vortexed. After incubation, the beads were washed three times with 0.7 ml of wash buffer comprising (20 mM HEPES, 0.01% TWEEN20, pH 8.0). The beads were then suspended in the wash buffer at a concentration of 10 mg/ml and stored at 4° C. until further use.

To encode for the entire Baby Spinach aptamer, four modified chimeric N-mers were designed and generated. Each N-mer comprised a 5' DMT-PO$_4$ group attached to an initial deoxyribonucleotide (dN) and a ribonucleotide (rN) at the 3' end. The DMT-PO$_4$ group provides a block to subsequent ligations after a single oligonucleotide is ligated to the growing chain.

In this example, the Baby Spinach sequence was divided into three 12-mers (Fragments A, B and C) and a 15-mer (Fragment D). The sequences of Fragments A-D are shown in Table 2.

TABLE 2

| Fragment Name | Sequence | SEQ ID NO |
|---|---|---|
| Fragment A | CCGTCCTTCACrC | 13 |
| Fragment B | GAACTACTGGArC | 14 |
| Fragment C | CTCAACAGTAGrC | 15 |
| Fragment D | GGAGCTCACACTCTrA | 16 |

Figure 16:
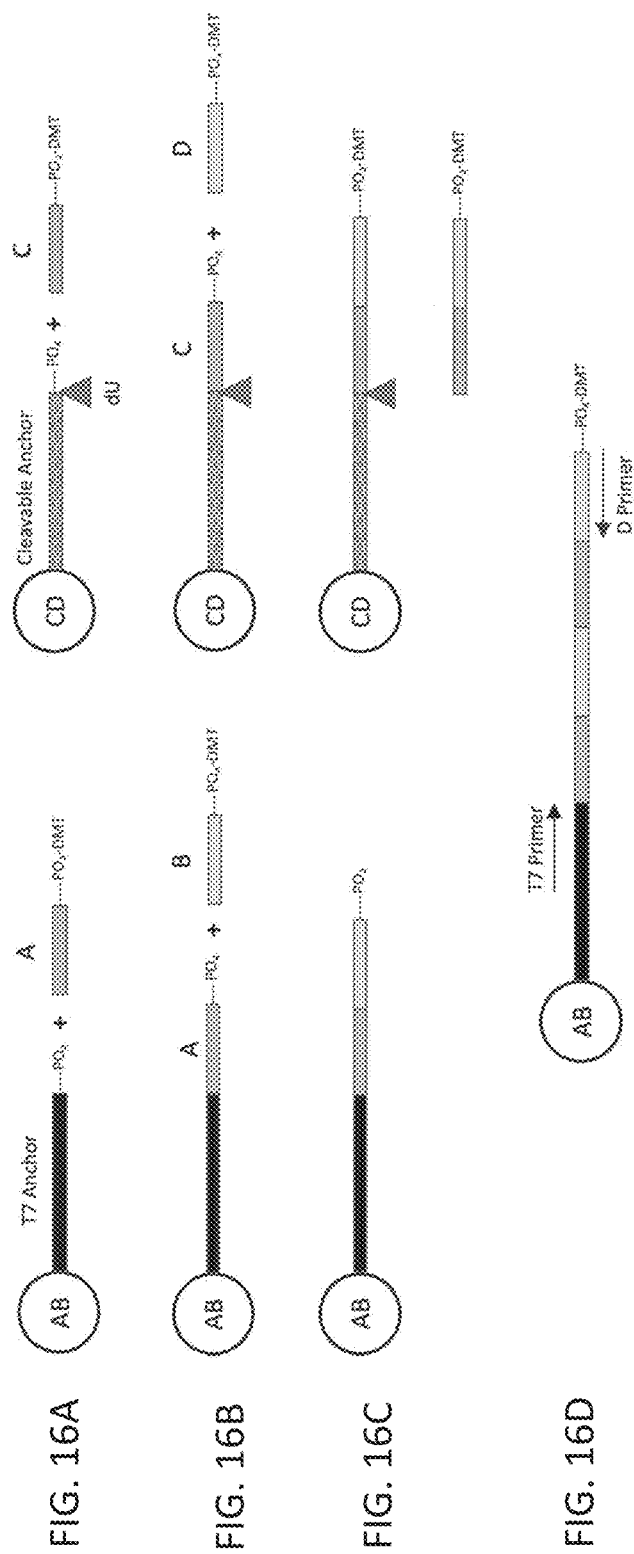

In the first step of geometric synthesis, Fragment A was ligated onto the 5' end of the AB anchor primer attached to the magnetic beads and Fragment C was ligated onto the 5' end of the CD anchor primer attached to magnetic beads, as shown in panel A of FIG. 16. For the ligation reactions, 2.5 µM of anchor primer/beads were incubated with 0.5 µM of the respective fragment (A or C) in the presence of 1.5 units/µl of T4 RNA ligase 1 in a buffer comprising 20 mM HEPES pH 8.0, 50 mM Potassium Acetate, 10 mM Magnesium Acetate, 0.1 mg/ml BSA and 0.01% TWEEN 20. The ligation reactions were incubated at 21° C. for 30 minutes. After the ligation reaction, the beads were washed using a magnetic separator by washing three times with 0.7 ml of a buffer comprising 20 mM HEPES pH 8.0 and 0.01% TWEEN 20, followed by a wash with 0.7 ml of 0.01% TWEEN 20.

Following the first ligation, the 5' PO$_4$ group of each ligated Fragment A and Fragment C were deprotected via an acid/base wash to allow for a second round of ligation. To deprotect the 5' PO$_4$ group, the beads were washed once with the ligation buffer, then once with 0.01% TWEEN 20, and then finally once briefly with acid buffer 3% dichloroacetic acid (DCA) in H$_2$O. After these washes, the beads were then incubated in acid buffer 3% dichloroacetic acid (DCA) in H$_2$O for 30 minutes with constant stirring. The beads were then washed with basic buffer comprising 1:9 Carbonate:Bicarbonate (~pH 9.0) and 0.01% TWEEN 20 and then incubated with the same buffer for 10 minutes with constant stirring. Finally, the beads were washed once with 0.01% TWEEN 20 and then washed twice with the ligation buffer.

After deprotection, a second round of ligation was performed wherein Fragment B was ligated to the 5' end of the ligated Fragment A (linked to the AB anchor primer and beads) to form a ligated Fragment AB and Fragment D was ligated to the 5' end of ligated Fragment C (linked to the CD anchor primer and beads) to form a ligated Fragment CD, as shown panel B of FIG. 16. The ligation reaction conditions were the same as for the first ligation described above.

Following ligation, the 5' PO$_4$ group on ligated Fragment AB was deprotected using the same acid/base wash described above, as show in panel C of FIG. 16. Furthermore, the CD beads, now linked to the CD anchor primer ligated to Fragment CD, were treated with uracil-N-deglycosylase (UNG) to remove the uracil base, leaving an abasic nucleotide. The beads were then treated with either Endo IV or APE-1, which are endonucleases capable of cutting at a single stranded abasic site, thereby releasing the Fragment CD from the anchor primer and beads, as shown in panel C of FIG. 16.

The untethered fragment CD was then ligated onto 5' end of the fragment AB (linked to the AB anchor primer and beads) using the ligation conditions described above to generate the complete sequence template for Baby Spinach, as shown in panel D of FIG. 16.

The Baby Spinach template was then amplified via polymerase chain reaction (PCR) using a primer complementary to the T7 promoter sequence in the AB anchor primer and a primer complementary to a portion of Fragment D, as shown in panel D of FIG. 16.

FIG. 17 shows polyacrylamide gel analysis of the 5' extension geometric synthesis of the Baby Spinach sequence template described above. Contents of each lane of the gel are described in Table 3

TABLE 3

Lane descriptions

| Lane # | Description |
| --- | --- |
| 1 | 100 bp marker |
| 2 | PCR of positive control, full length Baby Spinach construct |
| 3 | AB anchor primers (AB beads) |
| 4 | AB beads after ligation of Fragment A onto anchor primer (1$^{st}$ ligation) |
| 5 | AB beads after ligation of Fragment B onto Fragment A (2$^{nd}$ ligation) |
| 6 | CD anchor primers (CD beads) |
| 7 | CD beads after ligation of Fragment C onto anchor primer and Fragment D onto Fragment C (1$^{st}$ and 2$^{nd}$ ligations) |
| 8 | Sample of lane 7 after treatment with UDG and cleavage with Endo IV |
| 9 | Sample of lane 8 after ligation of released Fragment CD onto Fragment AB (3$^{rd}$ ligation) |
| 10 | PCR amplification of lane 9 |
| 11 | Sample of lane 7 after treatment with UDG and cleavage with APE-1 |
| 12 | Sample of lane 11 after Ligation of Released fragment CD onto Fragment AB (3$^{rd}$ ligation) |
| 13 | PCR amplification of lane 12 |

Example 2: 5' Modular Linear Synthesis

The following is an example that uses the 5' modular linear synthesis method of the present disclosure to generate sequence template of an RNA aptamer referred to as "Baby Spinach". Baby Spinach enhances the fluorescence of DFHBI. In this example, ligation and deprotection reactions are performed under the same conditions as described in Example 1 of the instant specification.

First, a biotinylated anchor primer comprising a T7 promoter sequence and a 5' PO$_4$ group were attached to streptavidin-coated, magnetic beads, using the anchor primer attachment method described in Example 1.

For this example, the same four Baby Spinach fragments (Fragments A-D) as described in Example 1 were used as N-mers in the modular linear synthesis reaction. In a first ligation reaction, Fragment A was ligated to the 5' end of the anchor primer linked to the magnetic beads, as shown in panel A of FIG. 18. The 5' PO$_4$ group of the ligated Fragment A was then deprotected.

Following deprotection, a second ligation reaction was performed wherein Fragment B was ligated to the 5' end of the ligated Fragment A (linked to the anchor primer and beads) to form a ligated Fragment AB, as shown in the panel B of FIG. 18. The 5' PO$_4$ group of the ligated Fragment AB was then deprotected.

Following deprotection, a third ligation reaction was performed wherein Fragment C was ligated to the 5' end of the ligated Fragment AB (linked to the anchor primer and beads) to form a ligated Fragment ABC, as shown in the panel C of FIG. 18. The 5' PO$_4$ group of the ligated Fragment ABC was then deprotected.

Following deprotection, a fourth ligation reaction was performed wherein Fragment D was ligated to the 5' end of the ligated Fragment ABC (linked to the anchor primer and beads) to form a ligated Fragment ABCD, as shown in the panel D of FIG. 18. Ligated Fragment ABCD corresponds to the full length Baby Spinach template sequence. The 5' PO$_4$ group of the ligated Fragment ABCD was then deprotected.

Following deprotection, a fifth ligation reaction was performed wherein a 5' adapter oligonucleotide was ligated to the 5' end of the ligated Fragment ABCD, as shown in Panel E of FIG. 18. The 5' adapter oligonucleotide comprised a 5' DMT-PO$_4$ group.

Following the fifth ligation reaction, the ligated Fragment ABCD was amplified via PCR using a primer complementary to the T7 promoter sequence located in the anchor primer and a primer complementary to the 5' adapter oligonucleotide, as shown in Panel F of FIG. 18. The primer complementary to the 5' adapter oligonucleotide also comprised a 5' TEG and biotin moiety. The PCR reaction was purified using streptavidin beads.

Following PCR purification, the amplified full length Baby Spinach template was used to synthesize the Baby Spinach RNA aptamer using RNA polymerase I. The synthesized aptamer and a control aptamer (synthesized from a DNA oligo synthesized using current methods in the art) were then incubated with 20 µM DFHBI. As shown in FIG. 19, both the synthesized aptamer and the control aptamer enhanced the fluorescence of DFHBI, showing the methods of the present disclosure can be used to effectively synthesize polynucleotide molecules that can be used in a variety of different applications.

FIG. 20 shows polyacrylamide gel analysis of the 5' modular linear synthesis method of the Baby Spinach sequence template described above. Contents of each lane of the gel are described in Table 4

TABLE 4

Lane descriptions

| Lane # | Description |
| --- | --- |
| 1 | 100 bp marker |
| 2 | Anchor primer |
| 3 | Full length control Baby Spinach construct |
| 4 | Beads after ligation of Fragment A onto anchor primer (1$^{st}$ ligation) |
| 5 | Beads after ligation of Fragment B onto Fragment A (2$^{nd}$ ligation) |
| 6 | Beads after ligation of Fragment C onto Fragment AB (3$^{rd}$ ligation) |
| 7 | Beads after ligation of Fragment D onto Fragment ABC (4$^{th}$ ligation) |
| 8 | Beads after ligation of 5' adapter oligonucleotide onto Fragment ABCD (5$^{th}$ ligation) |
| 9 | PCR amplification of lane 8 |
| 10 | Biotin cleanup of lane 9 |
| 11 | Transcription of lane 10 to make Baby Spinach RNA aptamer |

Example 3: 5' Modular Linear Synthesis with 5' Adenylation

The following is an example that uses the 5' modular linear synthesis method of the present disclosure in combination with 5' adenylation to generate a sequence template of an RNA aptamer referred to as "Baby Spinach".

First, a biotinylated anchor primer comprising a 5' PO$_4$ group, a DNA spacer sequence and a TEG spacer covalently linked to a biotin moiety was attached to streptavidin-coated, magnetic beads, using the anchor primer attachment method described in Example 1. This anchor primer comprised the sequence CTATAGTGAGTCGTAT-TACCGTAGTGCTGCGTCGAGTGT (SEQ ID: 11).

To encode for the entire Baby Spinach aptamer, four modified chimeric N-mers were designed and generated. Each N-mer comprised a 5' PO$_4$ group attached to an initial deoxyribonucleotide (dN) and a ribonucleotide (rN) at the 3' end.

In this example, the Baby Spinach sequence was divided into three 12-mers (Fragments A, B and C) and a 15-mer (Fragment D). The sequences of Fragments A-D are shown in Table 2.

The 5' modular linear synthesis reaction using these Fragments was performed as described in Example 2, with the exception that after each ligation step, no deprotecting step was performed. Instead, before the first ligation step and after each ligation step thereafter, the sample is treated with Mth RNA ligase, which adenylates the 5' end of the ligated fragments attached to the beads via their 5' PO$_4$ group. The adenylated 5' end is then primed for the next ligation.

FIG. 21 shows polyacrylamide gel analysis of the 5' modular linear synthesis method with 5' adenylation of the Baby Spinach sequence template described above. Contents of each lane of the gel are described in Table 5.

TABLE 5

Lane descriptions

| Lane # | Description |
| --- | --- |
| 1 | 100 bp marker |
| 2 | Anchor primer |
| 3 | After 4$^{th}$ ligation step (Fragment ABCD attached to beads) |

This example shows that the methods of the present disclosure can be controlled by 5' adenylation of the growing 5' ends.

Example 4: 5' Modular Linear Synthesis with 5' Phosphorylation

The following is an example that uses the 5' modular linear synthesis method of the present disclosure in combination with 5' phosphorylation to generate a sequence template of an RNA aptamer referred to as "Baby Spinach".

First, a biotinylated anchor primer comprising a 5' PO$_4$ group, a DNA spacer sequence and a TEG spacer covalently linked to a biotin moiety was attached to streptavidin-coated, magnetic beads, using the anchor primer attachment method described in Example 1. This anchor primer comprised the sequence TGGAATTCTCGGGTGC-CAAGGATGTTTTTTTTTT (SEQ ID: 17).

To encode for the entire Baby Spinach aptamer, four modified chimeric N-mers were designed and generated. Each N-mer comprised a 5' initial deoxyribonucleotide (dN) and a ribonucleotide (rN) at the 3' end.

In this example, the Baby Spinach sequence was divided into three 12-mers (Fragments A, B and C) and a 15-mer (Fragment D). The sequences of Fragments A-D are shown in Table 2.

The 5' modular linear synthesis reaction using these fragments was performed as described in Example 2, with the exception that after each ligation step, no deprotecting step was performed. Instead, after each ligation step, the sample is treated with T4 polynucleotide Kinase to phosphorylate the growing 5' end, thereby facilitating the next ligation step.

FIG. 22 shows polyacrylamide gel analysis of the 5' modular linear synthesis method with 5' phosphorylation of the Baby Spinach sequence template described above. Contents of each lane of the gel are described in Table 6.

TABLE 6

Lane descriptions

| Lane # | Description |
| --- | --- |
| 1 | 100 bp marker |
| 2 | Anchor primer |
| 3 | After 1$^{st}$ ligation step (Fragment A attached to beads) |
| 4 | After 2$^{st}$ ligation step (Fragment AB attached to beads) |
| 5 | After 3$^{st}$ ligation step (Fragment ABC attached to beads) |
| 6 | After 4$^{st}$ ligation step (Fragment ABCD attached to beads) |

This example shows that the methods of the present disclosure can be controlled by 5' phosphorylation of the growing 5' ends.

Example 5: 3' Extension Geometric Synthesis

The following is an example that uses the 3' extension geometric synthesis method of the present disclosure to generate a synthetic oligonucleotide.

First, a biotinylated anchor primer comprising a 5' Biotin moiety group linked to a TEG spacer, followed by a DNA spacer sequence, followed by a terminal 3' ribonucleotide (rN) was attached to streptavidin-coated, magnetic beads, using the anchor primer attachment method described in Example 1. This anchor primer comprised the sequence TTTTTTTTTTGTAGTGCTGCGTGCTCTTCrA (SEQ ID: 18).

For subsequent ligation reactions, an oligonucleotide fragment, herein referred to as "Substrate A" was used. Substrate A comprised a 5' PO$_4$ group, followed by a ribonucleotide sequence, followed by a 3' PO$_4$ group. The ribonucleotide sequence of Substrate A comprised the sequence: rGrGrUrGrArArGrGrArCrGrG (SEQ ID NO: 19).

In a first ligation reaction, substrate A was ligated onto the 3' end of the anchor primer attached to the magnetic beads using the ligation reaction conditions described in Example 1. In a subsequent second ligation reaction, another substrate A was ligated onto the 3' end of the substrate A ligated to the anchor primers, creating an "AA fragment". After this ligation reaction, the magnetic beads were split into two pools: pool 1 and pool 2.

Pool 1 was incubated with a single stranded DNA oligonucleotide herein referred to as a short reverse complementary oligonucleotide, comprising the nucleotide sequence: GAAGAGCACGCAGCACTAC (SEQ ID NO: 20). The short reverse complementary oligonucleotide comprises a sequence such that the short reverse complementary oligonucleotide hybridizes to the anchor primer to create a double-stranded DNA molecule that is cleavable by the Nt.BspQI nicking endonuclease. After incubation with and hybridization of the short reverse complementary oligonucleotide, the Pool 1 sample was treated with Nt.BspQI, thereby releasing ligated A fragments and ligated AA fragments.

Pool 2 was incubated with Shrimp Alkaline Phosphatase (rSAP) to remove the 3' PO$_4$ groups to prepare for subsequent ligation.

The released, ligated A and ligated AA fragments were then incubated with the rSAP-treated pool 2 and a ligation reaction performed to ligate the released fragments to the AA fragments attached to the anchor primers. The result is the synthesis of complete AAAA fragments as well as several lower molecular weight products.

FIG. 23 shows polyacrylamide gel analysis of the 3' extension geometric synthesis method described above. Contents of each lane of the gel are described in Table 7.

TABLE 7

Lane descriptions

| Lane # | Description |
|---|---|
| 1 | 100 bp marker |
| 2 | Anchor primer |
| 3 | After 1$^{st}$ ligation step (Fragment A attached to beads) |
| 4 | After 2$^{nd}$ ligation step (Fragment AA attached to beads) |
| 5 | After incubation with short reverse complementary oligonucleotide and Nt.BspQI (released |
| 6 | After 3$^{rd}$ ligation step |

This example demonstrates that the 3' extension geometric synthesis method of the present disclosure can be used to synthesize oligonucleotides

Example 6: Ligation of Chimeric N-Mers and Removal of Un-Ligated Contaminants The following is an example that demonstrates that a variety of N-mers comprising RNA-DNA chimeras as well as N-mers comprising only RNA can be ligated to a 5' phosphorylated DNA anchor primer, which has been attached to magnetic beads at the 3' end of the anchor primer.

First, a biotinylated anchor primer comprising a 5' PO$_4$ group, followed by a DNA spacer sequence, followed by a TEG spacer linked to a biotin moiety was attached to streptavidin-coated, magnetic beads, using the anchor primer attachment method described in Example 1. This anchor primer comprised the sequence TGGAAT-TCTCGGGTGCCAAGGATGTTTTTTTTTTT (SEQ ID: 17).

In this experiment, a set of six different N-mers were tested. The sequences of the N-mers are shown in Table 8. Chimera 1, Chimera 2 and Chimera 3 comprised a combination of deoxynucletodies (no prefix) and ribonucleotides (rC, rG, rA or rU).

TABLE 8

N-mer sequences

| N-mer | Sequence | SEQ ID NO |
|---|---|---|
| Chimera 1 | CCrG | — |
| Chimera 2 | TCrC | — |
| Chimera 3 | CCGTCCTTCACrC | 21 |
| RNA 12-mer | rGrArGrUrGrUrGrArGrCrUrC | 22 |
| RNA 6-mer | rCrArGrCrUrU | — |
| RNA 3-mer | rCrUrG | — |

A separate ligation reaction for each of the six different N-mers was performed using the ligation reaction conditions described in Example 1 to ligate the 3' end of each N-mer to the exposed 5' end of the anchor primer attached to the magnetic beads. FIG. 24 shows polyacrylamide gel analysis of these ligation reactions. Contents of each lane of the gel are described in Table 9. FIG. 24 shows that all of the N-mers tested can be ligated to the anchor primers bound to the magnetic beads.

TABLE 9

Lane descriptions

| Lane # | Description |
|---|---|
| 1 | 100 bp marker |
| 2 | Anchor primer |
| 3 | Anchor primer + Ligase |
| 4 | Chimera 1 ligation reaction |
| 5 | Chimera 2 ligation reaction |
| 6 | Chimera 3 ligation reaction |
| 7 | RNA 12-mer ligation reaction |
| 8 | RNA 6-mer ligation reaction |
| 9 | RNA 3-mer ligation reaction |

For cleaner products, it might be advantageous to remove un-ligated nucleic acids after each ligation reaction. This can be accomplished, for example, by the use of 5' to 3' exonucleases (in the case of 5' extension) or 3' to 5' exonucleases (for 3' extension). To this end, XRN-1, a S. cerevisiae exonuclease which is dependent on the presence of a 5' PO$_4$ group, was tested to determine if the enzyme can remove the un-ligated nucleic acids in the reactions described above. XRN-1 is capable of digesting both RNA and DNA and capable of digesting single stranded nucleic acids.

As treatment with ligase leaves some 5' ends adenylated, after each ligation step the sample was treated with S. cerevisiae 5' deadenylase, which removes the adenyl cap and leaves a monophosphate at the 5' ends, making them more susceptible to XRN-1 digestion. The samples from lanes 3-6 from FIG. 24 were first treated with S. cerevisiae 5' deadenylase, then with XRN-1, and the result was analyzed using polyacrylamide gel analysis as shown in FIG. 25. Contents of each lane of the gel are described in Table 10. These results demonstrate that exonuclease digestion can be used to effectively enriched for the desired ligation products in the methods of the present disclosure.

TABLE 10

Lane descriptions

| Lane # | Description |
|---|---|
| 1 | 100 bp marker |
| 2 | Anchor primer |
| 3 | Anchor primer + Ligase after XRN-1 digestion |
| 4 | Chimera 1 ligation reaction after XRN-1 digestion |
| 5 | Chimera 2 ligation reaction after XRN-1 digestion |
| 6 | Chimera 3 ligation reaction after XRN-1 digestion |

Example 7: Ligation of DNA to RNA Terminal Nucleotides

The following is an example that demonstrates that DNA-to-RNA ligations have a higher efficiency than DNA-to-DNA ligations when using T4 RNA ligase I. More specifically, the most efficient combination is a 3' ribonucleotide and a 5' deoxyribonucleotide, regardless of whether the 3' ribonucleotide is part of a chimeric molecule (a combination of DNA and RNA) or an RNA molecule.

In a first set of experiments, four different N-mers were used to test the efficiency of ligation. The sequence of the N-mers are shown in Table 11. The 5' PO$_4$ Donor N-mer further comprised a 5' PO$_4$ group and a 3' TEG linker attached to a biotin moiety. The Chimera N-mer further comprised a 5' biotin moiety linked to an initial deoxyribonucleotide (T) and a terminal 3' ribonucleotide (rG).

TABLE 11

N-mer sequences

| N-mer | Sequence | SEQ ID NO |
|---|---|---|
| 5' PO4 Donor N-mer | TACACGACGCTCTCTGAAGACACTCGATCCCTACACGACGCCGT CCGTTCTACCTCTTT | 23 |
| DNA N-mer | GACACATGAAAGCTTGAATTCACGGCATATGAGTCCATGG | 24 |
| Chimera N-mer | TTTTTTTTTCTTCCGATCTGAGTCCAGCrG | 25 |
| RNA N-mer | rGrUrUrCrArGrArGrUrUrCrUrArCrArGrUrCrCrGrArCrGrArUrC | 26 |

In a first ligation reaction, the 5' PO$_4$ Donor N-mer was ligated to the DNA N-mer. In a second ligation reaction, the 5' PO$_4$ Donor N-mer was ligated to the Chimera N-mer. In a third ligation reaction, 5' PO$_4$ Donor N-mer was ligated to the RNA N-mer. The results of these reactions were analyzed using polyacrylamide gel analysis as shown in FIG. 26. Contents of each lane of the gel are described in Table 12.

TABLE 12

Lane descriptions

| Lane # | Description |
|---|---|
| 1 | 100 bp marker |
| 2 | 5' PO$_4$ Donor N-mer |
| 3 | DNA N-mer, Chimera N-mer and RNA N-mer (no ligation) |
| 4 | 5' PO$_4$ Donor N-mer + DNA N-mer ligation |
| 5 | 5' PO$_4$ Donor N-mer + Chimera N-mer ligation |
| 6 | 5' PO$_4$ Donor N-mer + RNA N-mer ligation |

FIG. 26 shows that where there is a 3' OH group on a ribonucleotide and a 5' PO$_4$ group on a deoxynucleotide there is a much greater conversion to product, indicating higher ligation efficiency. A nucleic acid with 3' ribonucleotide, either pure RNA or a chimera with a terminal 3' ribonucleotide, has a greater efficiency of ligation.

In a second set of experiments, a set of 11 different N-mers was used. The sequences of the 11 different N-mers are shown in Table 13.

The 5' PO$_4$ Internal Fluor A, 5' PO$_4$ Internal Fluor C, 5' PO$_4$ Internal Fluor G and 5' PO$_4$ Internal Fluor T N-mers comprised an internal fluorescein-labeled nucleotide (a base-labelled thymine; Fluor-T), a 5' PO$_4$ group and a 3' TEG linker attached to a biotin moiety.

The 5' Cy5 Deoxy C, 5' Cy5 Deoxy G and 5' Cy5 Deoxy T N-mers (herein referred to collectively as the 5' Cy5 Deoxy N-mers) comprised a 5' Cy5 fluorescent label.

The 5' Cy5 Ribo A N-mer, Cy5 Ribo C N-mer, Cy5 Ribo G N-mer and Cy5 Ribo T N-mer (herein referred to collectively as the 5' Cy5 Ribo N-mers) comprised a 5' Cy5 fluorescent label and a terminal 3' ribonucleotide (rA, rC, rG or rT).

TABLE 13

N-mer sequences

| N-mer | Sequence | SEQ ID NO |
|---|---|---|
| 5' PO4 Internal Fluor A N-mer | AAGTAGCGAACTACTGGACCCG-Fluor-T-CCTTCACC | 27 |
| 5' PO4 Internal Fluor C N-mer | CAGTAGCGAACTACTGGACCCG-Fluor-T-CCTTCACC | 28 |
| 5' PO4 Internal Fluor G N-mer | GAGTAGCGAACTACTGGACCCG-Fluor-T-CCTTCACC | 29 |
| 5' PO4 Internal Fluor T N-mer | TAGTAGCGAACTACTGGACCCG-Fluor-T-CCTTCACC | 30 |
| 5' Cy5 Deoxy C N-mer | ACTAGTTACGGAGCTCAC | 31 |
| 5' Cy5 Deoxy G N-mer | TGAATGAAATGGTGAAGG | 32 |
| 5' Cy5 Deoxy T N-mer | CGCTTTAGGTTAAGACT | 33 |
| 5' Cy5 Ribo A N-mer | GGAGCTCACACTCTACTCArA | 34 |
| 5' Cy5 Ribo C N-mer | GGAGCTCACACTCTACTCArC | 35 |
| 5' Cy5 Ribo G N-mer | GGAGCTCACACTCTACTCArG | 36 |
| 5' Cy5 Ribo T N-mer | GGAGCTCACACTCTACTCArT | 37 |

First, the 5' PO$_4$ Internal Fluor A, 5' PO$_4$ Internal Fluor C, 5' PO$_4$ Internal Fluor G and 5' PO$_4$ Internal Fluor T N-mers were attached to separate streptavidin magnetic beads using the bead attachment method described in example 1. This yielded 4 different populations of beads.

The population of beads attached to 5' PO$_4$ Internal Fluor C N-mers was separately incubated with each of the Cy5 Deoxy N-mers and the Cy5 Ribo N-mers and subsequent ligation reactions were performed. The ligation yield of each reaction was monitored using flow cytometry. As a calibration, levels of relative fluorescence of Cy5 on one labeled N-mer versus Fluorescein on another N-mer were first determined at several ratios of Fluorescein to Cy5.

FIG. 27 shows that when the 3' terminal base and the 5' terminal base that are being ligated are both DNA, the ligation yield (efficiency) is significantly lower than when the 3' terminal base is a ribonucleotide and the 5' base is a deoxyribonucleotide.

To test for potential sequence bias (i.e. are there preferred terminal nucleotides that increase the ligation efficiency), each of the 4 different population of beads were then separately incubated with each of the Cy5 Ribo N-mers and a ligation reaction was performed. FIG. 28 that there is little or no bias among the four different ribonucleotides in terms of ligation yield (efficiency), indicating little to no sequence bias in ligation.

Example 8: Attaching Anchor Primers to a Solid Support Using Click Chemistry

The following is an example that demonstrates that oligonucleotides, such as anchor primers, can be attached to a bead using click chemistry (see e.g. Hao, J., Huang, L. L., Zhang, R., Wang, H. Z. & Xie, H. Y. A mild and reliable method to label enveloped virus with quantum dots by copper-free click chemistry. *Anal Chem* 84, 8364-8370, 2012) and used in the synthesis methods of the present disclosure.

In this example, an anchor primer comprising a 5' PO$_4$ group, followed by a DNA spacer sequence, followed by a 3' Dibenzylcyclooctyne (DBCO) group was used. The DNA spacer sequence comprised the nucleotide sequence:

(SEQ ID NO: 38)
CCATGGACTCATATGCCGTGAATTCAAGCTTTCATGTGTCTTCATAGT
CCGTCGTGTA.

The anchor primer was first attached via its 3' terminus to azide coated magnetic beads using click chemistry. After attachment of the anchor primer, the 3' terminus of an RNA N-mer (rArGrUrUrCrUrGrCrArGrUrCrUrGrCrArGrA-rArA, SEQ ID NO: 39) was ligated to the exposed 5' terminus of the anchor primer.

For comparison, an anchor primer comprising a 5' PO$_4$ group, followed by a 5' terminal ribonucleotide (rU), followed by a DNA spacer sequence (CCATGGACTCATATGCCGTGAA, SEQ ID NO: X), followed by a TEG linker attached to a biotin moiety, was attached to streptavidin coated beads and ligated to the same RNA N-mer.

FIG. 29 shows polyacrylamide gel analysis of the two ligation reactions described above. Contents of each lane are described in Table 14.

TABLE 14

| Lane descriptions | |
|---|---|
| Lane # | Description |
| 1 | 100 bp marker |
| 2 | RNA N-mer |
| 3 | Biotinylated anchor primer on streptavidin beads |
| 4 | RNA N-mer ligated onto biotinylated anchor on beads |
| 5 | DBCO anchor primer on azide ebads |
| 6 | RNA N-mer ligated onto DBCO anchor primer on beads |

FIG. 29 shows that both the click-attached anchor primer and the biotin attached anchor primer are suitable for ligation of the RNA N-mer. Thus, both click-attached anchor primers and biotin attached anchor primers can be used in the methods of the present disclosure.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER ASPECTS

While particular aspects of the present disclosure have been illustrated and described, various other changes and modifications can be made without departing from the spirit and scope of the present disclosure. The scope of the appended claims includes all such changes and modifications that are within the scope of the present disclosure.

Any of the above aspects can be combined with any other aspect.

What is claimed is:

1. A method comprising:
   a) contacting at least one first plurality of solid supports and at least one first plurality of anchor primers, under conditions that allow for the attachment of a 3' terminus of at least one anchor primer of the at least one first plurality of anchor primers to at least one solid support of the at least one first plurality of solid supports to produce at least one first anchor primer-substrate complex, wherein the anchor primers in the first plurality of anchor primers comprise at least one deoxyuridine at the 5' terminus;
   b) contacting the at least one first anchor primer-substrate complex and at least one first plurality of N-mers under conditions that append a 3' terminus of at least one N-mer of the at least one first plurality of N-mers to a 5' terminus of the at least one first anchor primer-substrate to produce at least one first extended anchor primer-substrate complex;
   c) contacting the at least one first extended anchor primer-substrate complex and at least one second plurality of N-mers under conditions that append a 3' terminus of at least one N-Mer of the at least one second plurality of N-mers to a 5' terminus of the at least one first extended anchor primer-substrate complex to produce at least one first donor complex;
   d) contacting at least one second plurality of solid supports and at least one second plurality of anchor primers, under conditions that allow for the attachment of a 3' terminus of at least one anchor primer of the at least one second plurality of anchor primers to at least one solid support of the at least one second plurality of solid supports to produce at least one second anchor primer-substrate complex;
   e) contacting the at least one second anchor primer-substrate complex and at least one third plurality of N-mers under conditions that append a 3' terminus of at least one N-mer of the at least one third plurality of N-mers to a 5' terminus of the at least one second anchor primer-substrate to produce at least one second extended anchor primer-substrate complex;
   f) contacting the at least one second extended anchor primer-substrate complex and at least one fourth plurality of N-mers under conditions that append a 3' terminus of at least one N-mer of the at least one fourth plurality of N-mers to a 5' terminus of the at least one second extended anchor primer-substrate complex to produce at least one first target complex;
   g) releasing at least one composition comprising the at least one N-mer of the at least one first plurality of N-mers and the at least one N-mer of the at least one second plurality of N-mers from the at least one first donor complex to produce at least one released intermediate complex by contacting the at least one first donor complex with a combination of uracil DNA glycosylase and at least one of DNA glycosylate-lyase, endonuclease VIII, Endo IV and APE-1; and
   h) contacting the at least one first target complex and the at least one released intermediate complex under conditions that append a 3' terminus of the at least one released intermediate complex to a 5' terminus of the at least one target complex to produce at least one first extended target complex,
   wherein the anchor primers of the first and second pluralities of anchor primers comprise deoxyribose 5' (DNA) terminus, and
   wherein the N-mers of the first, second, third and fourth pluralities of N-mers are chimeric N-mers comprising a deoxyribose 5' (DNA) terminus and a ribose 3' (RNA) terminus.

2. The method of claim 1, wherein appending comprises enzymatic ligation under conditions that allow for ligase activity.

3. The method of claim 2, wherein the enzymatic ligation comprises T4 RNA ligase activity.

4. The method of claim 1, further comprising, after the production of the at least one first anchor primer-substrate complex or the at least one second anchor primer-substrate complex, removing at least one unattached anchor primer.

5. The method of claim 4, wherein removing the at least one unattached anchor primer comprises contacting the at least one unattached anchor primer with an exonuclease, wherein the exonuclease comprises a 5' to 3' specific exonuclease, wherein the 5' to 3' specific exonuclease cannot digest nucleic acid molecules comprising a 5'-OH group.

6. The method of claim 1, further comprising, after production of the at least one first extended anchor primer-substrate complex, the at least one first donor complex, the at least one second extended anchor primer-substrate complex, the at least one first target complex or the at least one first extended target complex, removing at least one un-appended N-mer.

7. The method of claim 6, wherein removing the at least one un-appended N-mer comprises contacting the at least one un-appended N-mer with an exonuclease, wherein the exonuclease comprises a 5' to 3' specific exonuclease, wherein the 5' to 3' specific exonuclease cannot digest nucleic acid molecules comprising a 5'-OH group.

8. The method of claim 1, wherein the at least one first plurality of N-mers, the at least one second plurality of N-mers, the at least one third plurality of N-mers, the at least one fourth plurality of N-mers or any combination thereof comprise(s) at least one N-mer comprising an OH group at the 3' terminus and the 5' terminus of the N-mer.

9. The method of claim 8, further comprising, after production of the at least one first extended anchor primer-substrate complex and before contacting the at least one first extended anchor primer-substrate complex with at least one second plurality of N-mers, appending a $PO_4$ group to the 5' end of at least one N-mer of the at least one first plurality of N-mers.

10. The method of claim 8, further comprising, after producing the at least one second extended anchor primer-substrate complex and before contacting the at least one second extended anchor primer-substrate complex and at least one fourth plurality of N-mers, appending a $PO_4$ group to the 5' end of at least one N-mer of the at least one third plurality of N-mers.

11. The method of claim 8, further comprising, prior to contacting the at least one first target complex and the at least one released intermediate complex, appending a $PO_4$ group to the 5' end of at least one N-mer of the at least one fourth plurality of N-mers.

12. The method of claim 1, wherein the at least one first plurality of N-mers, the at least one second plurality of N-mers, the at least one third plurality of N-mers, the at least one fourth plurality of N-mers or any combination thereof comprise(s) at least one N-mer comprising an OH group at the 3' terminus and a $PO_4$ group at the 5' terminus of the N-mer.

13. The method of claim 12, wherein the $PO_4$ group is operably-linked to a protecting group.

14. The method of claim 13, further comprising, after production of the at least one first extended anchor primer-substrate complex and before the production of the at least one first donor complex, removing the protecting group from the at least one first extended anchor primer-substrate complex.

15. The method of claim 13, further comprising, after production of the at least one second extended anchor primer-substrate complex and before the production of the at least one first target complex, removing the protecting group from the at least one second extended anchor primer-substrate complex.

16. The method of claim 13, further comprising, before production of the at least one first extended target complex, removing the protecting group from the at least one first target complex.

17. The method of claim 12, further comprising, after production of the at least one first extended anchor primer-substrate complex and before the production of the at least one first donor complex, adenylating the 5' terminus of the at least one first extended anchor primer-substrate complex.

18. The method of claim 12, further comprising, after production of the at least one second extended anchor primer-substrate complex and before the production of the at least one first target complex, adenylating the 5' terminus of the at least one second extended anchor primer-substrate complex.

19. The method of claim 12, further comprising, before production of the at least one first extended target complex, adenylating the 5' terminus of the at least one first target complex.

* * * * *